(12) United States Patent
Pfahl et al.

(10) Patent No.: US 6,765,013 B2
(45) Date of Patent: Jul. 20, 2004

(54) THIAZOLIDINEDIONE DERIVATIVES FOR THE TREATMENT OF DIABETES AND OTHER DISEASES

(75) Inventors: Magnus Pfahl, Solana Beach, CA (US); Catherine Tachdjian, San Diego, CA (US); Hussien A. Al-Shamma, Encinitas, CA (US); Andrea Fanjul, San Diego, CA (US); David P. M. Pleynet, San Diego, CA (US); Lyle W. Spruce, Chula Vista, CA (US)

(73) Assignee: Incyte San Diego, Wilmington, DE (US)

( * ) Notice: Subject to any disclaimer, the term of this patent is extended or adjusted under 35 U.S.C. 154(b) by 0 days.

(21) Appl. No.: 10/334,932

(22) Filed: Dec. 31, 2002

(65) Prior Publication Data

US 2003/0153606 A1 Aug. 14, 2003

Related U.S. Application Data

(63) Continuation of application No. 09/652,810, filed on Aug. 31, 2000, now Pat. No. 6,515,003.
(60) Provisional application No. 60/151,670, filed on Aug. 31, 1999.

(51) Int. Cl.$^7$ ..................... A61K 31/425; C07D 277/04
(52) U.S. Cl. ....................................... 514/369; 548/183
(58) Field of Search ........................... 514/369; 548/183

(56) References Cited

U.S. PATENT DOCUMENTS

| | | | |
|---|---|---|---|
| 4,051,842 | A | 10/1977 | Hazel et al. |
| 4,140,122 | A | 2/1979 | Kuhl et al. |
| 4,383,529 | A | 5/1983 | Webster |
| 4,668,506 | A | 5/1987 | Bawa |
| 4,713,244 | A | 12/1987 | Bawa et al. |
| 4,788,063 | A | 11/1988 | Fisher et al. |
| 4,931,279 | A | 6/1990 | Bawa et al. |
| 4,971,996 | A | 11/1990 | Shiraishi |
| 5,223,522 | A | 6/1993 | Clark et al. |
| 5,330,998 | A | 7/1994 | Clark et al. |
| 5,512,689 | A | 4/1996 | Quallich |
| 5,523,314 | A | 6/1996 | Bue-Valleskey et al. |
| 5,650,444 | A | 7/1997 | Cagglano et al. |
| 5,691,376 | A | 11/1997 | Cagiano et al. |
| 5,780,676 | A | 7/1998 | Boehm et al. |
| 6,127,415 | A | 10/2000 | Pfahl et al. |
| 6,262,044 | B1 | 7/2001 | M.o slashed.ller et al. |
| 6,515,003 | B1 | 2/2003 | Pfahl et al. |

FOREIGN PATENT DOCUMENTS

| | | |
|---|---|---|
| EP | 0 212 617 | 3/1987 |
| EP | 0 304 493 | 3/1989 |
| EP | 0 343 643 | 11/1989 |
| EP | 1 048 659 | 11/1998 |
| EP | 1 142 885 | 10/2001 |
| JP | 55 038359 | 3/1980 |
| WO | WO 93/21146 | 10/1993 |
| WO | WO 94/12880 | 6/1994 |
| WO | WO 97/00249 | 1/1997 |
| WO | WO 97/03682 | 2/1997 |
| WO | WO 97/27191 | 7/1997 |
| WO | W0 99/09965 | 3/1999 |
| WO | WO 99/24415 | 5/1999 |
| WO | WO 99/58127 | 11/1999 |
| WO | WO 00/10573 | 3/2000 |
| WO | WO 00/18748 | 4/2000 |
| WO | WO 00/32598 | 6/2000 |
| WO | WO 00/066167 | 11/2000 |
| WO | WO 01/16122 | 3/2001 |
| WO | WO 01/16123 | 3/2001 |
| WO | WO 01/36402 | 5/2001 |
| WO | WO 02/071827 | 9/2002 |
| WO | WO 02/072009 | 9/2002 |
| WO | WO 02/072543 | 9/2002 |

OTHER PUBLICATIONS

Beilstein Registry No. 29–30, 1975, Compound Registry No. 1120438.
Beilstein Registry No. 52, 1978, Compound Registry No. 4939128.
Bradisher et al., "Aromatic Cyclodehydration XXIV. Cyclization of Derivatives of (2–biphenylly)pyruvic Acid," J. Org. Chem., 15(2) 374–376 (1950).
Cantello et al., "A Versatile Route to 2–Arylmethyl–1, 2–oxadiazolidine–3,5–diones via Regiospecific Alkyl–ation of 1,2,4–Oxadiazolidine–3,5–dione," Synlett, 263–264 (1997).
Charpentier et al., "Synthesis, Structure—Affinity Relationships, and Biological Activities of Ligands Binding to Retinoic Acid Receptor Subtypes," J. Med. Chem. 38:4993–5006 (1995).
Darses et al., "Palladium–Catalyzed Cross–Coupling Reactions of Arenediazonium Tetrafluoroborates with Aryl– and Alkenylboronic Acids," Bull. Soc. Chem. Fr., 133:1095–1102 (1996).
Ebisawa et al., "Novel Thiazolidinedione Derivatives with Retinoid Synergistic Activity," Biol. Pharma. Bull., 21(5):547–549 (1998).

(List continued on next page.)

Primary Examiner—Deborah C. Lambkin
(74) Attorney, Agent, or Firm—Needle & Rosenberg, P.C.

(57) ABSTRACT

The present invention relates to certain substituted heterocycles of Formula (I) which are useful in the treatment of diseases related to lipid and carbohydrate metabolism, such as type 2 diabetes, adipocyte differentiation, uncontrolled proliferation, such as lymphoma, Hodgkin's Disease, leukemia, breast cancer, prostate cancer or cancers in general; and inflammation, such as osteoarthritis, rheumatoid arthritis, Crohn's Disease or Inflammatory Bowel Disease.

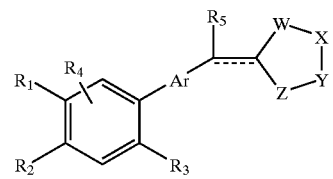

32 Claims, 11 Drawing Sheets-

OTHER PUBLICATIONS

Firooznia et al., "Enantioselective Synthesis of 4–Substituted Phenylalanines By Cross–Coupling Reactions," *Tetrahedron Letters*, 40:213–216 (1999).

Harris et al., "Localization of a Pioglitazone Response Element in the Adipocyte Fatty Acid–Binding Protein Gene," *Mol. Pharmacol.* 45:439–445 (1994).

Indolese, "Suzuki–Type Coupling of Chloroarenes with Arylboronic Acids Catalysed by Nickel Complexes," *Tetrahedron Letters*, 38:3513–3516 (1997).

Ishiyama et al., "Synthesis of Arylboronates via the Palladium(0)–Catalyzed Cross–Coupling Reaction of Tetra(alkoxo)diborons with Aryl Triflates," *Tetrahedron Letters*, 38:3447–3450 (1997).

Ishiyama et al., "Palladium(0)–Catalyzed Cross–Coupling Reaction of Alkoxydiboron with Haloarenes: A Direct Procedure for Arylboronic Esters," *J. Org. Chem.*, 60:7508–7510 (1995).

Littke et al., "A Convenient and General Method for Pd–Catalyzed Suzuki Cross–Couplings of Aryl Chlorides and Arylboronic Acids," *Angew. Chem. Int. Ed.*, 37:3387–3388 (1998).

Manickam et al., "New Parts for a Construction Set of Bifunctional Oligo(het)arylene Building Blocks for Modular Chemistry," *Synthesis*, 3:442–446 (2000).

Miyaura et al., "Palladium–Catalyzed Corss–Coupling Reactions of Organoboron Compounds," *Chem. Rev.*, 95:2457–2483 (1995).

Schandendorf et al., "Retinoic Acid Receptor–γ Selective Retinoids Exert Antiproliferative Effects on Human Melanoma Cell Growth In Vitro," *International Journal of Oncology* 5:1325–1331 (1994).

Stanforth, "Catalytic Cross–Coupling Reactions in Biaryl Synthesis," *Tetrahedron*, 54:263–303 (1998).

Suzuki, "New Synthetic Transformations Via Organoboron Compounds," *Pure & Applied Chem.*, 66:213–222 (1994).

Teboul et al., "Thiazolidinediones and Fatty Acids Convert Myogenic Cells Into Adipose–like Cells," *J. Biol. Chem.* 270:28183–28187 (1995).

Tietze et al., "The Knoevenagel Reaction," *Comprehensive Organic Synthesis*, 2:341–394 (1991).

Watanabe et al., "Synthesis of Sterically Hindered Biaryls via the Palladium–Catalyzed Cross–Coupling Reaction of Arylboronic Acids or Their Esters With Haloarenes," *Synlett.* 207–210 (1992).

Willson et al., "The Structure–Activity Relationship Between Peroxisome Proliferator–Activated Receptor (Agonism and the Antihyperglycemic Activity of Thiazolidinediones," *J. Med. Chem.*, 39:665–668 (1996).

Zask et al., "Synthesis of 3–Mercapto–2(5H)–Furanones via Reaction of Dilithio–2,4–thiazolidinedione With ∀–Halo Ketones," *Tetrahedron Letters*, 34 (17):2719–2722 (1993).

Alley et al., "Feasibility of Drug Screening with Panels of Human Tumor Cell Lines Using a Microculture Tetrazolium Assay," *Cancer Re.*, 48:589–601 (1988).

Amin et al., "Nitric Oxide Synthase and Cyclooxygenases: Distribution, Regulation, and Intervention in Arthritis," *Nitric pin. Rheumatol*, 11(3):202–209 (1999).

Aranyos et al., "Novel Electron–Rich Bulky Phospine Ligands Facilitate the Palladium–Catalyzed Preparation of Diaryl Ethers," *J. Am. Chem. Soc.*, 121:4369–4378 (1999).

Baraldi et al., "Exhaled Nitric Oxide Concentrations During Treatment of Wheezing Exacerbation in Infants and Young Children," *Am. J. Respir. Crit. Care Med.*, 159 (4 Pt. 1):1284–1288 (1999).

Black, "Simple Synthesis of 1–Azaadamantan–4–one," *Synthesis*, 829–830 (1981).

Blondet et al., "Convenient Synthesis of 6–Methyl, 8–Methyl and 6,8–Dimethyl Derivatives of 5–Hydroxy–1,2,3,4–Tetrahydro–2–Quinolinone," *Organic Preparation and Procedures Int.*, 25(2):223–228 (1993).

Bredt et al., "Isolation of Nitric Oxide Synthetase, a Calmodulin–Requiring Enzyme," *Proc. Natl. Acad. Sci.*, 87:682–685 (1990).

Brennan et al., "Inhibitory Effect of TNF Antibodies on Synovial Cell Interleukin–1 Production in Rheumatoid Arthritis," *Lancet*, 2:244–247 (1989).

Cantello et al., "The Synthesis of BRL 49653—A Novel and Potent Antihyperglycaemic Agent," *Bioorganic & Medicinal Chemistry Letters*, 4:1181–1184 (1994).

Chan et al., "New N– and O–Arylations with Phenyloboronic Acids and Curpric Acetate," *Tetrahedron Letters*, 39:2933–2936 (1998).

Chang et al., "The Upjohn Colony of Kka$^y$ Mice: A Model for Obese Type II Diabetes," *Elsevier Science Publishers B.V., Biomedical Division, Diabetes*, pp. 466–470 (1986).

Choi et al., "Similarity of Colorectal Cancer in Crohn's Disease and Ulcerative Colitis: Implications for Carcinogenesis and Prevention," *Gut*, 35:950–954 (1994).

Cobb et al., "N–(2–Benzolphenyl)–L–tyrosine PPAR$_y$ Agonists. 3. Structure–Activity Relationship and Optimization of the N–Aryl Substituent," *J. Med. Chem.*, 41:5055–5069 (1998).

Coleman "Diabetes–Obesity Syndromes in Mice," *Diabetes*, 31(1):1–6 (Apr. 1982).

Dawson et al., "Conformational Effects on Retinoid Receptor Selectivity. 2. Effects of Retinoid Bridging Group on Retinoid X Receptor Activity and Selectivity," *J. Med. Chemistry*, 38:3368–3383 (1995).

Dawson et al., "The Synthetic Chemistry of Retinoids," *Biology, Chemistry, and Medicine*, 2$^{nd}$ Edition, Raven Press, Ltd., New York (1994).

Evans et al., "Synthesis of Diaryl Ethers through the Copper–Promoted Arylation of Phenols with Arylboronic Acids. An Expedient Synthesis of Thyroxine," *Tetrahedron Letters*, 39:2937–2940 (1998).

Farahat et al., "Cytokine Epression in Synovial Membranes of Patients with Rheumatoid Arthritis and Osteoarthritis," *Ann. Rheum. Dis.*, 52:870–875 (1993).

Ferrell, "Tripping the Switch Fantastic: How A Protein Kinase Cascade Can Convert Graded Inputs into Switch Like Outputs," *TIBS*, 21:460–466 (1996).

Förstermann et al., "Induced RAW 264.7 Macrophages Express Soluble and Particulate Nitric Oxide Synthase: Inhibition By Transforming Growth Factor–," *Eur. J. Pharm.*, 225:161–165 (1992).

Fukuto et al., "Inhibition of Constitutive and Inducible Nitric Oxide Synthase: Potential Selective Inhibition," *Annu. Rev. Pharmacol. Toxicol.* 35:165–194 (1995).

Gahtan et al., "Inflammatory Pathogenesis in Alzheimer's Disease: Biological Mechanisms and Cognitive Sequeli," *Neurosci. Biobehav*, 23:615–633 (1999).

Glauser et al., "Pathogenesis and Potential Strategies for Prevention and Treatment of Septic Shock: An Update," *Clin. Infect Dis.* 18 (Suppl. 2):S205–216 (1994).

Gown, et al., "Human Atherosclerosis—II. Immunocytochemical Analysis of the Cellular Composition of Human Atherosclerotic Lesions," *Am. J. Pathol.*, 125(1):191–207 (1986).

Gray et al., "Practical Methylation of Aryl Halides by Suzuki–Miyaura Coupling," *Tetrahedron Letters*, 41:6237–6240 (2000).

Haddach et al., "A New Method for the Synthesis of Ketones: The Palladium–Catalyzed Corss–Coupling of Acid Chlorides with Arylboronic Acids," *Tetrahedron Letters*, 40:3109–3112 (1999).

Hudlicky, "Oxidations in Organic Chemistry," *ACS Monograph*, 186:114–127 (1990).

Hudlicky, "Oxidations in Organic Chemistry," *ACS Monograph*, 186:133–149 (1990).

Ishiyama et al., "Palladium–Catalyzed Carbonylative Cross Coupling Reaction of Arylboronic Acids with Aryl Electrophiles: Synthesis of Biaryl Ketones," *J. Org. Chem.*, 63:4726–4731 (1998).

Ishiyama et al. "Synthesis of Unsymmetrical Biaryl Ketones via Palladium–Catalyzed Carbonylative Cross–Coupling Reaction of Arylboronic Acids with Iodoarenes," *Tetrahedron Letters*, 34:7595–7598 (1993).

Jung et al., "New Efficient Method for the Total Synthesis of (S,S)–Isodityrosine from Natural Amino Acids," *J. Org. Chem.*, 64:2976–2977 (1999).

Kamidawa et al., "Palladium–Catalyzed Amination of Aryl Bromides Utilizing Arene–Chromium Complexes as Ligands," *J. Org. Chem.*, 63:8407–8410 (1998).

Kawai et al., "Enhancement of Rat Urinary Bladder Tumorigenesis by Lipopolysaccharide–induced inflammation," *Cancer Res.*, 53:5172–5175 (1993).

Kriegler et al., "A Novel Form of TNF/Cachectin is a Cell Surface Cytotoxic Transmembrane Protein: Ramifications for the Complex Physiology of TNF," *Cell*, 53:45–53 (1988).

Kyriakis et al., "Sounding the Alarm: Protein Kinase Cascades Activated by Stress and Inflammation," *J. Biol. Chem.*, 271:24313–24316 (1996).

Louie et al., "Palladium–Catalyzed Amination of Aryl Triflates and Importance of Triflate Addition Rate," *J. Org. Chem.*, 62:1268–1273 (1997).

McCann et al., "The Nitric Oxide Hypothesis of Aging," *Exp. Gerontol*, 33(7–8):813–826 (1998).

McCann, "The Nitric Oxide Hypothesis of Brain Aging," *Exp. Gerontol*, 32:431–440 (1997).

Molina et al., "The Role of Nitric Oxide in Neurodegeneration—Potential for Pharmacological Intervention," *Drugs & Aging*, 12(4):251–259 (1998).

Moroz et al., "The Ullmann Ether Condensation," *Russ. Chem. Rev.*, 43:679–689 (1974).

Oliff, "The Role of Tumor Necrosis Factor (Cachectin) in Cachexia," *Cell*, 54:141–142 (1988).

Oram, "Molecular Basic of Cholesterol Homeostasis: Lessons from Tangier Disease and ABCA1," *Trends in Molecular Medicines*, 8(4):168–173 (2002).

Paradisi, "Arene Substitution via Nucleophilic Addition to Electron Deficient Arenes," *Comprehensive Organic Synthesis*, 4:423–450 (1991).

Petrov et al., "The Arbuzov Rearrangement with Participation of Halogenoacetylenes as a Method of Synthesis of Ethynylphosphonates and other Organo–phosphorus Compounds," *Russ. Chem. Rev.*, 52:1030–1035 (1983).

Pohlman et al., "An Endothelial Cell Surface Factor(s) Induced in Vitro By Lipopolysaccharide, Interleukin I, and Tumor Necrosis Factor– Increases Neutrophil Adherence By A CDw18–Dependent Mechanism," *J. Immunol*, 136:4548–4553 (1986).

Pollock et al., "Purification and Characterization of Particulate Endothelium–derived Relaxing Factor Synthase from Cultured and Native Bovine Aortic Endothelial Cells," *Proc. Nat. Acad. Sci.*, 88:10480–10484 (1991).

Pujol–Borrell et al., "HLA Class II Induction In Human Islet Cells By Interferon– Plus Tumour Necrosis Factor or Lymphotoxin," *Nature*, 326:304–306 (1987).

Rosin et al., "Inflammation, Chromosomal Instability, and Cancer: The Schistosorniasis Model" *Cancer Res.*, 54 (7 Suppl):1929s–1933s (1994).

Ross "Atherosclerosis—An Inflammatory Disease," *New England Journal of Medicine*, 340(2):115–126 (Jan. 1999).

Rust et al. "Tangier disease is caused by mutations in the gene encoding ATP–binding cassette transporter 1," *Nature Genetics*, 22:352–355 (Aug. 1999).

Sanders, "Asthma, Viruses, and Nitric Oxide," *Proc. Soc. Exp. Biol. Med.*, 220(3):123–132 (1999).

Serfaty–Lacrosniere et al., "Homozygous Tangier disease and cardiovascular disease," *Atherosclerosis*, 107:85–98 (1994).

Shao et al., "p53 Independent $G_0/G_1$ Arrest and Apoptosis Induced by a Novel Retinoid in Human Breast Cancer Cells," *Oncogene*, 11:493–504 (1995).

Smith et al., "The Active Form of Tumor Necrosis Factor Is A Trimer," *J. Biol. Chem.*, 262:6951–6954 (1987).

Sparrow et al., "A Potent Synthetic LXR Agonist is More Effective than Cholesterol Loading at Inducing ABCA1 mRNA and Stimulating Cholesterol Efflux," *Journal of Biological Chemistry*, 277(12):10021–10027 (2002).

Spruce et al., "Heteroarotinoids. Synthesis, Characterization, and Biological Activity in Terms of An Assessment of these Systems to Inhibit the Induction of Ornithine Decarboxylase Activity and to Induce Terminal Differentiation of HL–60 Cells," *J. Med. Chem.*, 30:1474–1482 (1987).

Stirling et al., "Increase In Exhaled Nitric Oxide Levels in patients With Difficult Asthma and Correlation With Symptoms and Disease Severity Despite Treatment With Oral and Inhaled Corticosteroids," *Thorax*, 53(12):1030–1034 (1998).

Strieter et al., "Endothelial Cell Gene Expression of a Neutrophil Chemotactic Factor by TNF–, LPS, and IL–1," *Science*, 243:1467–1469 (1989).

Thompson et al., "Effect of carcinogen dose and age at administration on induction of mammary carcinogenesis by 1–methyl–1–nitrosourea," *Carginogenesis*, 13(9):1535–1539 (1992).

Thorns et al., "nNOS Expressing Neurons in the Entorhinal Cortex and Hippocampus Are Affected in Patients With Alzheimer's Disease," *Exp. Neurol*, 150:14–20 (1998).

Tracey et al., "Anti–Cachectin/TNF Monoclonal Antibodies Prevent Septic Shock During Lethal Bacteraemia," *Nature*, 330:662–664 (1987).

Tracey et al., "Tumor Necrosis Factor: A Pleiotropic Cytokine and Therapuetic Target," *Ann. Rev. Med.*, 45:491–503 (1994).

Uysal et al. "Protection From Obesity–induced Insulin Resistance in Mice Lacking TNF– Function," *Nature*, 389:610–614 (1997).

Wadsworth, "Synthetic Applications of Phosphoryl–Stabilized Anions," *Organic Reactions*, 25:73–253 (1977).

Walter et al., "The High Density Lipoprotein—and Apolipoprotein A–1–Induced Mobilization of Cellular Cholesterol is Impaired in Fibroblasts from Tangier Disease Subjects," *Biochemical and Biophysical Research Communications*, 205(1):850–856 (1994).

Weiberth et al., "Copper(I)–Activated Addition of Grignard Reagents to Nitriles. Synthesis of Ketimines, Ketones, and Amines," *J. Org. Chem.*, 52:3901–3904 (1987).

Wolfe et al., "Scope and Limitations of the Pd/BINAP–Catalyzed Amination of Aryl Bromides," *J. Org. Chem.*, 65:1144–1157 (2000).

Wolfe et al., "Simple, Efficient Catalyst System for the Palladium–Catalyzed Amination of Aryl Chlorides, Bromides and Triflates," *J. Org. Chem.*, 65:1158–1174 (2000).

Yun et al., "Neurobiology of Nitric Oxide," *Crit. Rev. Neurobiol.*, 10:291–316 (1996).

Zask et al., "Synthesis and Antihyperglycemic Activity of Novel 5–(naphthalenylsufonyl)–2,4–thiazolidinediones," *J.Med.Chem.*, 33:1418–1423 (1990).

THIAZOLIDINEDIONE DERIVATIVES FOR THE TREATMENT OF DIABETES AND OTHER DISEASES

This application is a continuation application claiming priority to U.S. patent application Ser. No. 09/652,810, filed Aug. 31, 2000, now U.S. Pat. No. 6,515,003 which status is now allowed, which claimed priority to U.S. provisional application Serial No. 60/151,670, filed Aug. 31, 1999, the priority of which is also claimed hereby. The disclosure of both parent applications are hereby incorporated herein in their entirety by this reference.

BACKGROUND OF THE INVENTION

Type 2 diabetes, also referred to as non-insulin dependent diabetes mellitus (NIDDM), afflicts between 80 and 90% of all diabetic patients in developed countries. In the United States alone, approximately 15 million people, and more than 100 million worldwide, are affected. Because this disorder is a late onset disease and occurs often in overweight persons it can be expected that the number of patients suffering from this disease will increase further. Patients suffering from type 2 diabetes usually still produce insulin but become increasingly resistant to their own insulin and to insulin therapy. A promising new class of drugs has been recently introduced that resensitizes patients to their own insulin (insulin sensitizers), thereby reducing blood glucose and triglyceride levels, and thus abolishing, or at least reducing, the requirement for exogenous insulin. Troglitazone (Resulin™) and rosiglitazone (Avandia™) belong to the thiazolidinediones (TZD) class of chemicals, and are the first representatives of this class of chemicals approved for the treatment of type 2 diabetes in the United States and several other countries. These compounds, however, have side effects including rare but severe liver toxicities (i.e., troglitazone) and they can increase body weight in humans. Such side effects are of major concern for patients who might require treatment for a decade or longer. Therefore, new and better drugs for the treatment of type 2 diabetes and related disorders are needed. New heterocyclic derivatives that are useful, for example, to modulate metabolism (such as, for example, lipid metabolism and carbohydrate metabolism) or adipocyte differentiation, and especially to treat type 2 diabetes and other diseases are disclosed.

SUMMARY OF THE INVENTION

The present invention relates to certain substituted heterocycles which are useful in the treatment of diseases related to lipid metabolism and adipocyte differentiation, such as type 2 diabetes; uncontrolled proliferation, such as lymphoma, Hodgkin's Disease, leukemia, breast cancer, prostate cancer, or cancers in general; and inflammation, such as osteoarthritis, rheumatoid arthritis, Crohn's Disease, or Inflammatory Bowel Disease.

Some disclosed embodiments of the invention relate to compounds of the Formula (I):

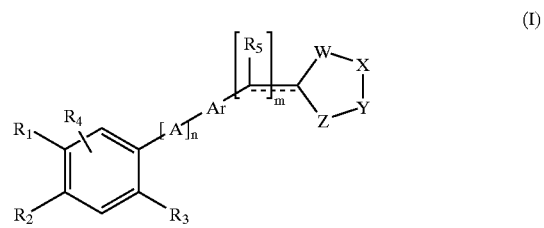

wherein:

n and m are independently 0 or 1;

$R_1$ and $R_2$ are 1) independently or together hydrogen, alkyl, substituted alkyl, haloalkyl, alkenyl, substituted alkenyl, alkynyl, substituted alkynyl, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide or haloalkoxy; or 2) R1 and R2 together with the aromatic ring bonded thereto form a cycloalkyl, substituted cycloalkyl, cycloalkenyl or substituted cycloalkenyl residue that may optionally comprise 1 or 2 heteroatoms selected from O, S, NH or N-alkyl;

$R_3$ and $R_4$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

A is —$CR_6R_7$— where $R_6$ and $R_7$ are independently or together hydrogen, alkyl, substituted alkyl, alkoxy, substituted alkoxy or haloalkoxy; or $R_6$ and $R_7$ together form a cycloalkyl residue that may optionally comprise 1 or 2 heteroatoms selected from O, S, NH and N-alkyl;

Ar is Formula (II), (III), (IV) or (V):

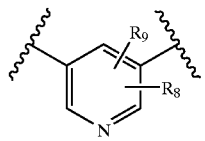
(V)

where
R$_8$, R$_9$ and R$_{10}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

R$_5$ is hydrogen, halogen, hydroxy, alkyl or substituted alkyl;

— represents a bond present or absent; and

W, X, Y and Z are independently or together —C(O)—, —C(S)—, —S—, —O— or —NH-residues that together form a 2,4-thiazolidinedione, 2-thioxo-4-thiazolidinedione, isoxazolidinedione, 2,4-imidazolidinedione or 2-thioxo-4-imidazolidinedione residue; or a pharmaceutically acceptable salt thereof.

Other embodiments of the invention provide methods of synthesizing the compounds of the invention.

In another aspect, this invention relates to the use of the compounds disclosed herein for modulating lipid metabolism, carbohydrate metabolism, lipid and carbohydrate metabolism, or adipocyte differentiation; they are also useful for treating diseases of uncontrolled cellular proliferation; and the treatment inflammatory diseases.

This invention also relates to a method for modulating lipid metabolism, carbohydrate metabolism, lipid and carbohydrate metabolism or adipocyte differentiation comprising administering to a mammal, preferably a human, diagnosed as needing such modulation, such as for the treatment of type 2 diabetes. The invention also provides for a method of treatment of a disease of uncontrolled cellular proliferation comprising administering to a mammal diagnosed as having a disease of uncontrolled cellular proliferation and a method of treating an inflammatory disease comprising administering to a mammal diagnosed as having an inflammatory disease.

In another aspect, this invention relates to a pharmaceutical composition comprising a compound disclosed herein in admixture with one or more pharmaceutically acceptable excipients.

DETAILED DESCRIPTION

Figure 1A:
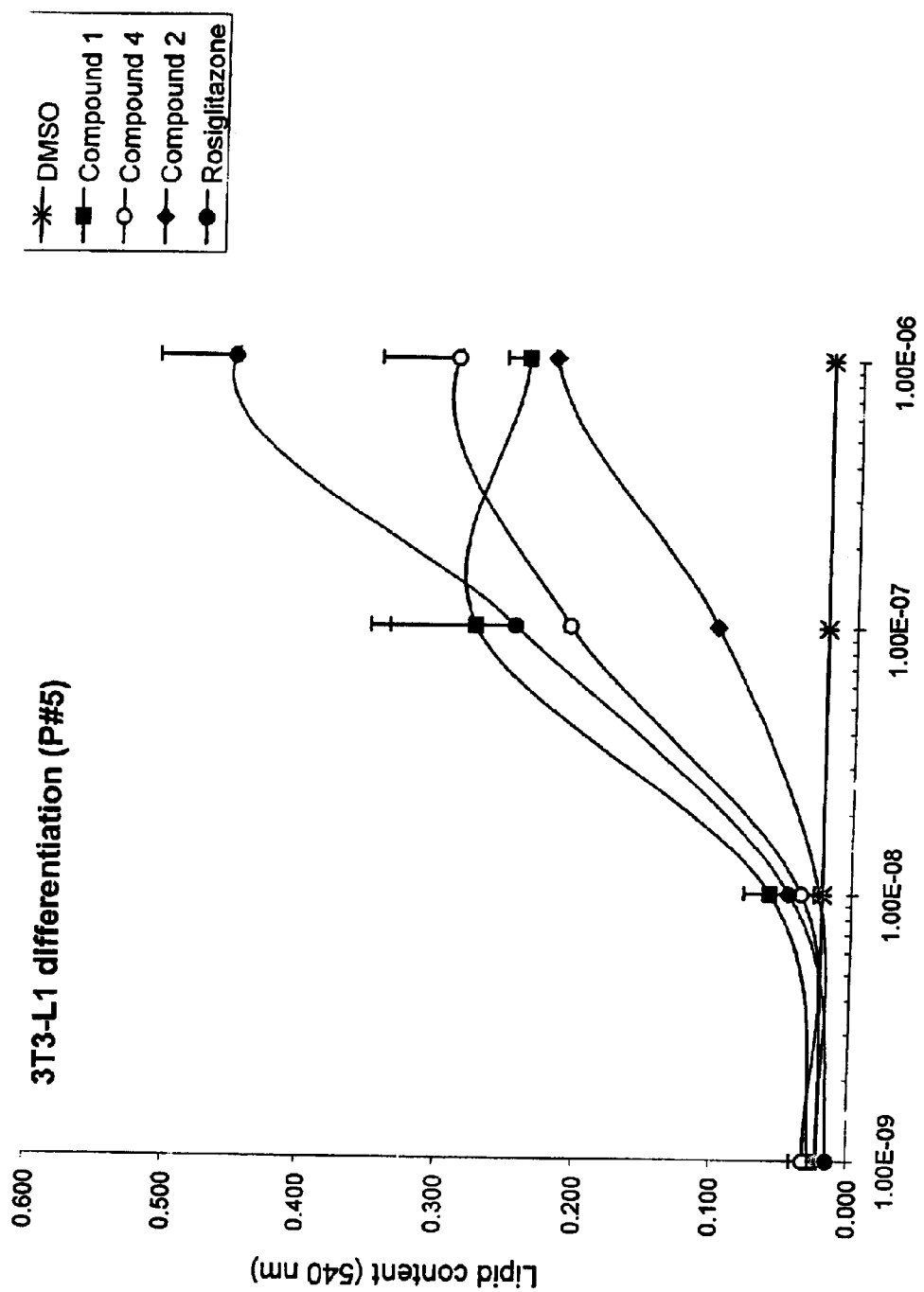
FIG. 1a shows the differentiation inducing activity of the compounds of the present invention in the absence of insulin.

The present invention provides compounds that are useful, for example, to modulate lipid metabolism or adipocyte differentiation, and especially for the treatment of diabetes, such as type 2 diabetes, and other diseases. Compounds disclosed herein are characterized by relatively low molecular weight and may be used to treat diseases in representative animal models such as those of type 2 diabetes. In addition, compounds of the invention have demonstrated oral bioavailability as exhibited by their high blood levels after oral dosing, either alone or in the presence of an excipient. Oral bioavailability allows oral dosing for use in chronic diseases, with the advantage of self-administration and decreased cost over other means of administration. The compounds described herein may be used effectively to prevent, alleviate or otherwise treat type 2 diabetes and/or other disease states in mammals, including humans.

Definitions

In the specification and Formulae described herein the following terms are hereby defined.

The term "alkyl" denotes a radical containing 1 to 12 carbons, such as methyl, ethyl, n-propyl, iso-propyl, n-butyl, sec-butyl, t-butyl, amyl, t-amyl, n-pentyl and the like.

The term "alkenyl" denotes a radical containing 1 to 12 carbons such as vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "alkynyl" denotes a radical containing 1 to 12 carbons, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "substituted alkyl" denotes a radical containing 1 to 12 carbons of the above definitions that are substituted with one or more groups, but preferably one, two or three groups, selected from hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they may be the same or different.

The term "substituted alkenyl" denotes a radical containing 1 to 12 carbons of the above definitions that are substituted with one or more groups, but preferably one, two or three groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they may be the same or different.

The term "substituted alkynyl" denotes a radical containing 1 to 8 carbons of the above definitions that are substituted with one or more groups, but preferably one or two groups, selected from halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy.

The term "cycloalkyl" denotes a radical containing 3 to 8 carbons, such as cyclopropyl, cyclobutyl, cyclopentyl, cyclopenyl, cyclohexyl, cycloheptyl and the like. The term "substituted cycloalkyl" denotes a cycloalkyl as defined above that is further substituted with one or more groups selected from halogen, alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkyl is substituted with more than one group, they may be the same or different.

The term "cycloalkenyl" denotes a radical containing 3 to 8 carbons, such as cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl and the like. The term "substituted cycloalkenyl" denotes a cycloalkenyl as defined above further substituted with one or more groups selected from halogen, alkyl, hydroxyl, alkoxy, substituted alkoxy, haloalkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkenyl is substituted with more than one group, they may be the same or different.

The term "alkoxy" as used herein denotes a radical alkyl, defined above, attached directly to an oxygen such as methoxy, ethoxy, n-propoxy, iso-propoxy, n-butoxy, t-butoxy, iso-butoxy and the like.

The term "substituted alkoxy" denotes a radical alkoxy of the above definition that is substituted with one or more groups, but preferably one or two groups, selected from hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they may be the same or different.

The term "mono-substituted amino" denotes an amino substituted with one group selected from alkyl, substituted alkyl or arylalkyl wherein the terms have the same definitions found throughout.

The term "di-substituted amino" denotes an amino substituted with two radicals that may be same or different selected from aryl, substituted aryl, alkyl, substituted alkyl or arylalkyl wherein the terms have the same definitions found throughout. Some examples include dimethylamino, methylethylamino, diethylamino and the like.

The term "haloalkyl" denotes a radical alkyl, defined above, substituted with one or more halogens, preferably fluorine, such as a trifluoromethyl, pentafluoroethyl and the like.

The term "haloalkoxy" denotes a haloalkyl, as defined above, that is directly attached to an oxygen to form trifluoromethoxy, pentafluoroethoxy and the like.

The term "acyl" denotes a radical containing 1 to 8 carbons such as formyl, acetyl, propionyl, butanoyl, iso-butanoyl, pentanoyl, hexanoyl, heptanoyl, benzoyl and the like.

The term "acyloxy" denotes a radical containing 1 to 8 carbons of an acyl group defined above directly attached to an oxygen such as acetyloxy, propionyloxy, butanoyloxy, iso-butanoyloxy, benzoyloxy and the like.

The term "aryl" denotes an aromatic ring radical containing 6 to 10 carbons that includes phenyl and naphthyl. The term "substituted aryl" denotes an aromatic radical as defined above that is substituted with one or more selected from hydroxyl, cycloalkyl, aryl, substituted aryl, heteroaryl, heterocyclic ring, substituted heterocyclic ring, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, alkylthio, alkoxy, substituted alkoxy or haloalkoxy, wherein the terms are defined herein.

The term "halo" or "halogen" refers to a fluoro, chloro, bromo or iodo group.

The term "thioalkyl" denotes a sulfide radical containing 1 to 8 carbons, linear or branched. Examples include methyl sulfide, ethyl sulfide, isopropyl sulfide and the like.

The term "thiohaloalkyl" denotes a thioalkyl radical substituted with one or more halogens. Examples include trifluoromethylthio, 1,1-difluoroethylthio, 2,2,2-trifluoroethylthio and the like.

The term "carboalkoxy" refers to an alkyl ester of a carboxylic acid, wherein alkyl has the same definition as found above. Examples include carbomethoxy, carboethoxy, carboisopropoxy and the like.

The term "alkylcarboxamide" denotes a single alkyl group attached to the amine of an amide, wherein alkyl has the same definition as found above. Examples include N-methylcarboxamide, N-ethylcarboxamide, N-(iso-propyl)carboxamide and the like. The term "substituted alkylcarboxamide" denotes a single "substituted alkyl" group, as defined above, attached to the amine of an amide.

The term "dialkylcarboxamide" denotes two alkyl or arylalkyl groups that are the same or different attached to the amine of an amide, wherein alkyl has the same definition as found above. Examples of a dialkylcarboxamide include N,N-dimethylcarboxamide, N-methyl-N-ethylcarboxamide and the like. The term substituted "dialkylcarboxamide" denotes two alkyl groups attached to the amine of an amide, where one or both groups is a "substituted alkyl", as defined above. It is understood that these groups may be the same or different. Examples include N,N-dibenzylcarboxamide, N-benzyl-N-methylcarboxamide and the like.

The term "alkylamide" denotes an acyl radical attached to an amine or monoalkylamine, wherein the term acyl has the same definition as found above. Examples of "alkylamide" include acetamido, propionamido and the like.

The term "arylalkyl" defines an alkylene, such as —CH$_2$— for example, which is substituted with an aryl group that may be substituted or unsubsiituted as defined above. Examples of an "arylalkyl" include benzyl, phenethylene and the like.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH2CH2O— repeat units in the polyester, regardless of whether ethylene glycol is used to prepare the polyester. Similarly, a 2,4-thiazolidinedione residue in a chemical compound refers to one or more -2,4-thiazolidinedione moieties of the compound, regardless of whether the residue was obtained by reacting 2,4-thiazolidinedione to obtain the compound.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Compositions

Some disclosed embodiments of the invention relate to the Formula (I):

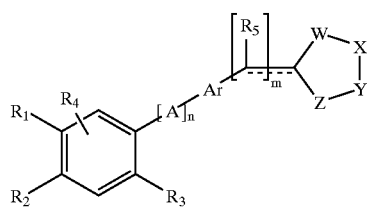

(I)

wherein:

n and m are independently 0 or 1;

$R_1$ and $R_2$ are independently or together hydrogen, alkyl, substituted alkyl, haloalkyl, alkenyl, substituted alkenyl, alkynyl, substituted alkynyl, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide or haloalkoxy; or $R_1$ and $R_2$ together with the aromatic ring form a cycloalkyl, substituted cycloalkyl, cycloalkenyl or substituted cycloalkenyl optionally comprising 1 or 2 heteroatoms selected from O, S, NH and N-alkyl;

$R_3$ and $R_4$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

A is —$CR_6R_7$— where $R_6$ and $R_7$ are independently or together hydrogen, alkyl, substituted alkyl, alkoxy, substituted alkoxy or haloalkoxy; or $R_6$ and $R_7$ together form a cycloalkyl comprising 1 or 2 heteroatoms selected from O, S, NH and N-alkyl;

Ar is Formula (II), (III), (IV) or (V):

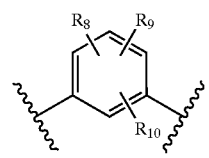

(II)

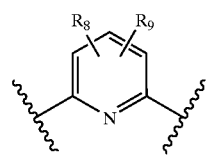

(III)

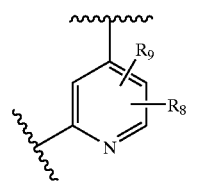

(IV)

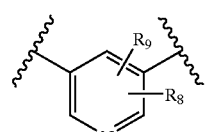

(V)

where $R_8$, $R_9$ and $R_{10}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

$R_5$ is hydrogen, halogen, hydroxy, alkyl or substituted alkyl;

— represents a bond present or absent; and

W, X, Y and Z are independently or together —C(O)—, —C(S)—, —S—, —O— or —NH—, preferably such that they form a 2,4-thiazolidinedione, 2-thioxo-4-thiazolidinedione, isoxazolidinedione, 2,4-imidazolidinedione or 2-thioxo-4-imidazolidinedione residue. These residues can be illustrated by the following Formulae:

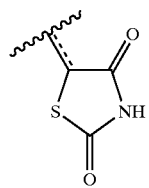
2,4-thiazolidinedione

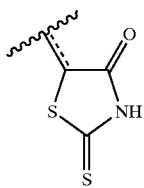
2-thioxo-4-thiazolidinedione

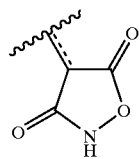

isoxazolidinedione

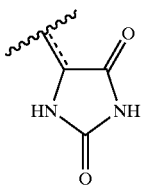

2,4-imidazolidinedione

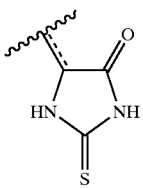

2-thioxo-4-imidazolidinedione

Any compound disclosed herein may optionally be formulated as a pharmaceutically acceptable salt.

In some embodiments W, X, Y and Z are independently or together —C(O)—, —C(S)—, —S—, —O—, or —NH— to form a 2,4-thiazolidinedione, 2-thioxo-4-thiazolidinedione, 2,4-imidazolidinedione or 2-thioxo-4-imidazolidinedione residue.

In some embodiments n is 0; $R_1$ and $R_2$ are independently or together alkyl, substituted alkyl or hydroxyl; or $R_1$ and $R_2$ together with the aromatic ring bonded thereto form a substituted cycloalkyl optionally comprising 1 or 2 heteroatoms selected from O, NH or N-alkyl;

In another embodiment $R_3$ and $R_4$ are independently or together halogen, alkyl, substituted alkyl, haloalkyl, alkoxy, substituted alkoxy, amino, mono-substituted amino, di-substituted amino or haloalkoxy.

In one embodiment $R_5$ is hydrogen, alkyl or substituted alkyl. In another embodiment, $R_5$ is hydrogen.

In another embodiment Ar is Formula (VI), (VII) or (VIII):

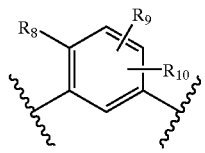

(VI)

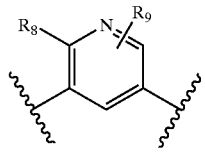

(VII)

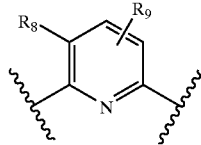

(VIII)

wherein:
$R_8$ is alkyl, substituted alkyl, alkenyl, haloalkyl, hydroxy, acyloxy, halogen, alkoxy, substituted alkoxy, amino, mono-substituted amino, di-substituted amino, alkylamide or haloalkoxy; and $R_9$ and $R_{10}$ are independent or together hydrogen, halogen, alkyl, substituted alkyl, haloalkyl, alkenyl, substituted alkenyl, alkoxy, hydroxyl, amino, mono-substituted amino, di-substituted amino, alkylamide or haloalkoxy.

In some embodiments — represents a bond present and the compound is a benzylidene compound having the structural Formula:

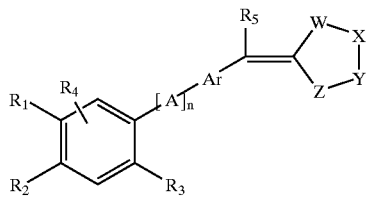

In some embodiments — represents a bond absent and the compound is a benzyl compound having the structural Formula:

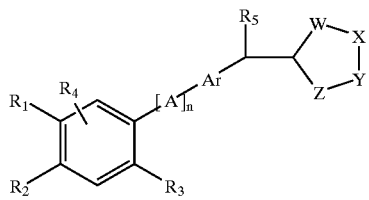

In another embodiment of the invention $R_1$ and $R_2$ together with the aromatic ring bonded thereto form a substituted cycloalkyl.

In still another embodiment $R_3$ is methyl, ethyl, trifluoromethyl, methoxy or dimethylamino; and $R_4$ is hydrogen.

In another embodiment $R_1$ and $R_2$ together with the aromatic ring bonded thereto form a substituted cycloalkyl; $R_3$ is methyl, ethyl, trifluoromethyl, methoxy or dimethylamino; and $R_4$ is hydrogen, to form a polycyclic residue. Preferred polycyclic residues may be selected from:

1) 3,5,5,8,8-pentamethyl-5,6,7,8-tetrahydro-2-naphthyl:

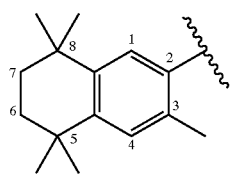

2) 3-ethyl-5,5,8,8-tetramethyl-5,6,7,8-tetrahydro-2-naphytHyl:

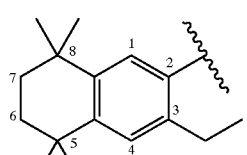

3) 3-trifluoromethyl-5,5,8,8-tetramethyl-5,6,7,8-tetrahydro-2-naphthyl:

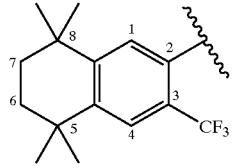

-continued 4) 3-methoxy-5,5,8,8-tetramethyl-5,6,7,8-tetrahydro-2-naphthyl:

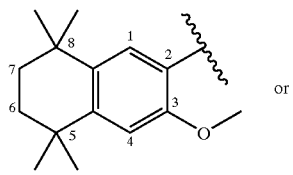 or 5) 3-dimethylamino-5,5,8,8-tetramethyl-5,6,7,8-tetrahydro-2-naphthyl:

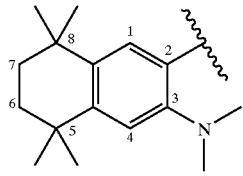

In some embodiments, $R_1$ and $R_2$ together with the aromatic ring of Formula I form a substituted cycloalkyl residue having the 5,5,8,8-tetramethyl-5,6,7,8-tetrahydro-2-naphthyl radical:

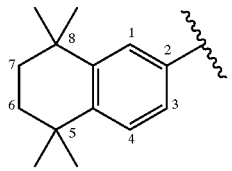

in another embodiment, $R_1$ and $R_2$ together with the aromatic ring of Formula I form a substituted cycloalkyl optionally comprising 1 or 2 nitrogen heteroatoms, to give a 1-isopropyl-7-methyl-1,2,3,4-tetrahydro-6-quinolinyl radical;

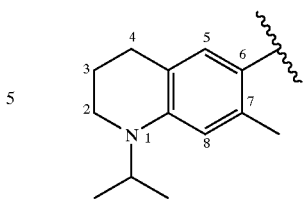

or a 1,4-diisopropyl-6-methyl-1,2,3,4-tetrahydro-7-quinoxalinyl radical:

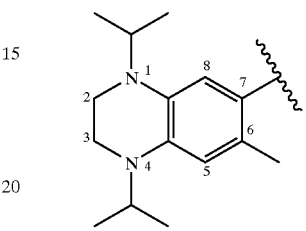

In still another embodiment of the invention wherein the A group is present (i.e. n is 1), $R_1$ and $R_2$ together with the aromatic ring form a cycloalkyl or substituted cycloalkyl optionally comprising 1 or 2 nitrogen heteroatoms; $R_3$ is halogen, alkyl, substituted alkyl, haloalkyl, alkoxy, substituted alkoxy, haloalkoxy, amino, mono-substituted amino or di-substituted amino; $R_6$ and $R_7$ together form a cycloalkyl optionally comprising 1 or 2 oxygen heteroatoms, and W, X, Y and Z are independently or together —C(O)—, —C(S)—, —S— or —NH— to form a 2,4-thiazolidinedione, 2-thioxo-4-thiazolidinedione, 2-thioxo-4-imidazolidinedione or 2,4-imidazolidinedione residue.

This invention also relates to a pharmaceutical formulation comprising one or more compounds disclosed herein in an admixture with a pharmaceutically acceptable excipient.

Compounds disclosed herein may exist in various tautomeric forms. For example, 2,4-thiazolidinedione-containing compounds disclosed herein may exist in the form of tautomers (Xa), (Xb) and (Xc).

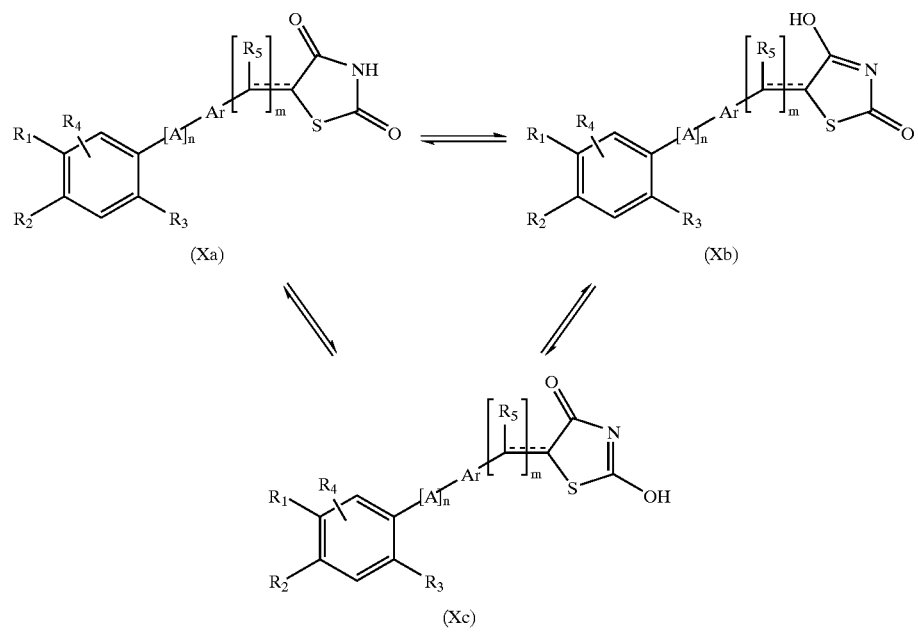

It is understood by those of skill in the art that tautomers may also exist with 2-thioxo-4-thiazolidinedione, 2,4-imidazolidinedione, 2-thioxo-4-imidazolidinedione and isoxazolidinedione containing compounds disclosed herein. For convenience, all of the tautomers may be presented herein by a single formula, but it is understood that all tautomers are within the scope of the invention.

When — is present both E and Z configurations are within the scope of the invention. For example, 2,4-thiazolidinedione and 2-thioxo-4-thiazolidinedione of Formula (I) may have the following structures respectively:

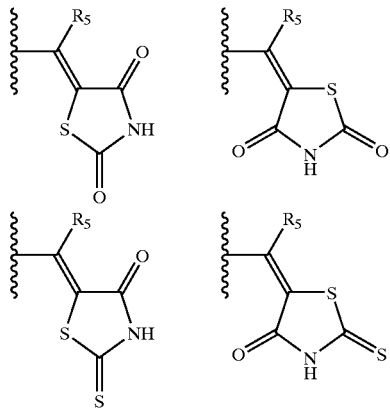

The compounds disclosed herein may also include salts of the compounds, such as salts with cations. Cations with which the compounds of the invention may form pharmaceutically acceptable salts include alkali metals, such as sodium or potassium; alkaline earth metals, such as calcium; and trivalent metals, such as aluminum. The only constraint with respect to the selection of the cation is that it should not unacceptably increase the toxicity. Due to the tautomerism described above for the compounds, mono-, di- or tri-salts may be possible depending on the corresponding; alkali metal. Also, one or more compounds disclosed herein may include salts formed by reaction of a nitrogen contained within the compound, such as an amine, aniline, substituted aniline, pyridyl and the like, with an acid, such as HCl, carboxylic acid and the like. Therefore, all possible salt forms in relationship to the tautomers and a salt formed from the reaction between a nitrogen and acid are within the scope of the invention.

The present invention provides, but is not limited to, the specific compounds set forth in the Examples as well as those set forth below, and a pharmaceutically acceptable salt thereof:
where
n is 0, and — is absent or present:
  3-(3,5,5,8,8-Pentamethyl-5,6,7,8-tetrahydro-2-naphthyl)-4-methoxybenzylidene-2,4-thiazolidinedione,
  3-(3,5,5,8,8-Pentamethyl-5,6,7,8-tetrahydro-2-naphthyl)-2-fluoro-4-methoxybenzylidene)-2,4-thiazolidinedione,
  5-(3,5,5,8,8-Pentamethyl-5,6,7,8-tetrahydro-2-naphthyl)-6-methoxy-3-pyridylidene-2,4-thiazolidinedione,
  6-(3,5,5,8,8-Pentamethyl-5,6,7,8-tetrahydro-2-naphthyl)-5-methoxy-2-pyridylidene-2,4-thiazolidinedione,
  3-(3,5,5,8,8-Pentamethyl-5,6,7,8-tetrahydro-2-naphthyl)-4-methoxybenzylidene-2-thioxo-4-thiazolidinedione,
  3-(3,5,5,8,8-Pentamethyl-5,6,7,8-tetrahydro-2-naphthyl)-4-methoxy-6-hydroxybenzylidene-2,4-thiazolidinedione,
  3-(3,5,5,8,8-Pentamethyl-5,6,7,8-tetrahydro-2-naphthyl)-4,6-dimethoxybenzylidene-2,4-thiazolidinedione,
  3-(3,5,5,8,8-Pentamethyl-5,6,7,8-tetrahydro-2-naphthyl)-4,6-dihydroxybenzylidene-2,4-thiazolidinedione,
  3-(1,4-Diisopropyl-6-methyl-1,2,3,4-tetrahydro-7-quinoxalinyl)-4-methoxybenzylidene-2,4-thiazolidinedione,
  3-(5,5,8,8-Tetramethyl-5,6,7,8-tetrahydro-2-naphthyl)-2,4-dimethoxybenzylidene-2,4-thiazolidinedione,
  3-(5,5,8,8-Tetramethyl-5,6,7,8-tetrahydro-2-naphthyl)-4-methoxybenzylidene-2,4-thiazolidinedione,
  3-(1-Isopropyl-7-methyl-1,2,3,4-tetrahydro-6-quinolinyl)-4-methoxybenzylidene-2,4-thiazolidinedione,
  3-(3,5,5,8,8-Pentamethyl-5,6,7,8-tetrahydro-2-naphthyl)-4,5-dimethoxybenzylidene-2,4-thiazolidinedione,
  3-(3,5,5,8,8-Pentamethyl-5,6,7,8-tetrahydro-2-naphthyl)-4-hydroxybenzylidene-2,4-thiazolidinedione,
  3-(3,5,5,8,8-Pentamethyl-5,6,7,8-tetrahydro-2-naphthyl)-4-methoxy-5-fluorobenzylidene-2,4-thiazolidinedione,
  3-(3,5,5,8,8-Pentamethyl-5,6,7,8-tetrahydro-2-naphthyl)-4-methoxy-2,5-difluorobenzylidene-2,4-thiazolidinedione,
  3-(3,5-Di-t-butyl-4-hydroxyphenyl)-3-methoxybenzylidene-2,4-thiazolidinedione,
  3-(3,5,5,8,8-Pentamethyl-5,6,7,8-tetrahydro-2-naphthyl)-2-fluoro-4-methoxybenzylidene-2-thioxo-4-thiazolidinedione,
  5-(3,5,5,8,8-Pentamethyl-5,6,7,8-tetrahydro-2-naphthyl)-6-methoxy-3-pyridylidene-2-thioxo-4-thiazolidinedione,
  6-(3,5,5,8,8-Pentamethyl-5,6,7,8-tetrahydro-2-naphthyl)-5-methoxy-2-pyridylidene-2-thioxo-4-thiazolidinedione,
  3-(3,5,5,8,8-Pentamethyl-5,6,7,8-tetrahydro-2-naphthyl)-4-methoxy-6-hydroxybenzylidene-2-thioxo-4-thiazolidinedione,
  3-(3,5,5,8,8-Pentamethyl-5,6,7,8-tetrahydro-2-naphthyl)-4,6-dimethoxybenzylidene-2-thioxo-4-thiazolidinedione,
  3-(3,5,5,8,8-Pentamethyl-5,6,7,8-tetrahydro-2-naphthyl)-4,6-dihydroxybenzylidene-2-thioxo-4-thiazolidinedione,
  3-(1,4-Diisopropyl-6-methyl-1,2,3,4-tetrahydro-7-quinoxalinyl)-4-methoxybenzylidene-2-thioxo-4-thiazolidinedione,
  3-(5,5,8,8-Tetramethyl-5,6,7,8-tetrahydro-2-naphthyl)-2,4-dimethoxybenzylidene-2-thioxo-4-thiazolidinedione,
  3-(5,5,8,8-Tetramethyl-5,6,7,8-tetrahydro-2-naphthyl)-4-methoxybenzylidene-2-thioxo-4-thiazolidinedione,
  3-(1-Isopropyl-7-methyl-1,2,3,4-tetrahydro-6-quinolinyl)-4-methoxybenzylidene-2-thioxo-4-thiazolidinedione,
  3-(3,5,5,8,8-Pentamethyl-5,6,7,8-tetrahydro-2-naphthyl)-4,5-dimethoxybenzylidene-2-thioxo-4-thiazolidinedione,
  3-(3,5,5,8,8-Pentamethyl-5,6,7,8-tetrahydro-2-naphthyl)-4-hydroxybenzylidene-2-thioxo-4-thiazolidinedione, 3-(3,5,5,8,8-Pentamethyl-5,6,7,8-tetrahydro-2-naphthyl)-4-methoxy-5-fluorobenzylidene-2-thioxo-4-thiazolidinedione, 3-(3,5,5,8,8-Pentamethyl-5,6,7,8-tetrahydro-2-naphthyl)4-methoxy-2,5-difluorobenzylidene-2-thioxo-4-thiazolidinedione, 3-[(3,5,5,8,8-Pentamethyl-5,6,7,8-tetrahydro-2-naphthyl)-4-methoxybenzyl]-2,4-thiazolidinedione, 3-[(3,5,5,8,8-Pentamethyl-5,6,7,8-tetrahydro-2-naphthyl)-4-trifluoromethoxybenzyl]-2,4-thiazolidinedione, 3-[(3,5,5,8,8-Pentamethyl-5,6,7,8-tetrahydro-2-naphthyl)-4-dimethylaminobenzyl]-2,4-thiazolidinedione, 3-[(3,5,5,8,8-Pentamethyl-5,6,7,8-tetrahydro-2-naphthyl)-2-fluoro-4-methoxybenzyl)]-2,4-thiazolidinedione, 5-[(3,5,5,8,8-Pentamethyl-5,6,7,8-tetrahydro-2-naphthyl)-6-methoxy-3-pyridylmethylene]-2,4-thiazolidinedione, 6-[(3,5,5,8,8-Pentamethyl-5,6,7,8-tetrahydro-2-naphthyl)-5-methoxy-2-pyridylmethylene]-2,4-thiazolidinedione, 3-[(3,5,5,8,8-Pentamethyl-5,6,7,8-tetrahydro-2-naphthyl)-4-methoxybenzyl]-2-thioxo-4-thiazolidinedione, 3-(3,5,5,8,8-Pentamethyl-5,6,7,8-tetrahydro-2-naphthyl)-4-methoxy-6-hydroxybenzyl-2,4-thiazolidinedione, 3-(3,5,5,8,8-Pentamethyl-5,6,7,8-tetrahydro-2-naphthyl)-4,6-dimethoxybenzyl-2,4-thiazolidinedione, 3-(3,5,5,8,8-Pentamethyl-5,6,7,8-tetrahydro-2-naphthyl)-4,6-dihydroxybenzyl-2,4-thiazolidinedione, 3-(1,4-Diisopropyl-6-methyl-1,2,3,4-tetrahydro-7-quinoxalinyl)-4-methoxybenzyl-2,4-thiazolidinedione, 3-(5,5,8,8-Tetramethyl-5,6,7,8-tetrahydro-2-naphthyl)-2,4-dimethoxybenzyl-2,4-thiazolidinedione, 3-(5,5,8,8-Tetramethyl-5,6,7,8-tetrahydro-2-naphthyl)-4-methoxybenzyl-2,4-thiazolidinedione, 3-(1-Isopropyl-7-methyl-1,2,3,4-tetrahydro-6-quinolinyl)-4-methoxybenzyl-2,4-thiazolidinedione, 3-(3,5,5,8,8-Pentamethyl-5,6,7,8-tetrahydro-2-naphthyl)-4,5-dimethoxybenzyl-2,4-thiazolidinedione, 3-(3,5,5,8,8-Pentamethyl-5,6,7,8-tetrahydro-2-naphthyl)-4-hydroxybenzyl-2,4-thiazolidinedione, 3-(3,5,5,8,8-Pentamethyl-5,6,7,8-tetrahydro-2-naphthyl)-4-methoxy-5-fluorobenzyl-2,4-thiazolidinedione, 3-(3,5,5,8,8-Pentamethyl-5,6,7,8-tetrahydro-2-naphthyl)-4-methoxy-2,5-difluorobenzyl-2,4-thiazolidinedione, 3-(3,5,5,8,8-Pentamethyl-5,6,7,8-tetrahydro-2-naphthyl)-2-fluoro-4-methoxybenzyl-2-thioxo-4-thiazolidinedione, 5-(3,5,5,8,8-Pentamethyl-5,6,7,8-tetrahydro-2-naphthyl)-6-methoxy-3-pyridylmethylene-2-thioxo-4-thiazolidinedione, k 6-(3,5,5,8,8-Pentamethyl-5,6,7,8-tetrahydro-2-naphthyl)-5-methoxy-2-pyridylmethylene-2-thioxo-4-thiazolidinedione, 3-(3,5,5,8,8-Pentamethyl-5,6,7,8-tetrahydro-2-naphthyl)-4-methoxy-6-hydroxybenzyl-2-thioxo-4-thiazolidinedione, 3-(3,5,5,8,8-Pentamethyl-5,6,7,8-tetrahydro-2-naphthyl)-4,6-dimethoxybenzyl-2-thioxo-4-thiazolidinedione, 3-(3,5,5,8,8-Pentamethyl-5,6,7,8-tetrahydro-2-naphthyl)-4,6-dihydroxybenzyl-2-thioxo-4-thiazolidinedione, 3-(1,4-Diisopropyl-6-methyl-1,2,3,4-tetrahydro-7-quinoxalinyl)-4-methoxybenzyl-2-thioxo-4-thiazolidinedione, 3-(5,5,8,8-Tetramethyl-5,6,7,8-tetrahydro-2-naphthyl)-2,4-dimethoxybenzyl-2-thioxo-4-thiazolidinedione, 3-(5,5,8,8-Tetramethyl-5,6,7,8-tetrahydro-2-naphthyl)-4-methoxybenzyl-2-thioxo-4-thiazolidinedione, 3-(1-Isopropyl-7-methyl-1,2,3,4-tetrahydro-6-quinolinyl)-4-methoxybenzyl-2-thioxo-4-thiazolidinedione, 3-(3,5,5,8,8-Pentamethyl-5,6,7,8-tetrahydro-2-naphthyl)-4,5-dimethoxybenzyl-2-thioxo-4-thiazolidinedione, 3-(3,5,5,8,8-Pentamethyl-5,6,7,8-tetrahydro-2-naphthyl)-4-hydroxybenzyl-2-thioxo-4-thiazolidinedione, 3-(3,5,5,8,8-Pentamethyl-5,6,7,8-tetrahydro-2-naphthyl)-4-methoxy-5-fluorobenzyl-2-thioxo-4-thiazolidinedione, 3-(3,5,5,8,8-Pentamethyl-5,6,7,8-tetrahydro-2-naphthyl)-4-methoxy-2,5-difluorobenzyl-2-thioxo-4-thiazolidinedione, 3-(3,5,5,8,8-Pentamethyl-5,6,7,8-tetrahydro-2-naphthyl)-4-methoxybenzylidene-2-thioxo-4-imidazolidinedione, 3-(3,5,5,8,8-Pentamethyl-5,6,7,8-tetrahydro-2-naphthyl)-2-fluoro-4-methoxybenzylidene-2-thioxo-4-imidazolidinedione, 3-(3,5,5,8,8-Pentamethyl-5,6,7,8-tetrahydro-2-naphthyl)-2-fluoro-4-methoxybenzylidene-2-thioxo-4-imidazolidinedione, 6-(3,5,5,8,8-Pentamethyl-5,6,7,8-tetrahydro-2-naphthyl)-5-methoxy-2-pyridylidene-2-thioxo-4-imidazolidinedione, 3-(3,5,5,8,8-Pentamethyl-5,6,7,8-tetrahydro-2-naphthyl)-4-methoxy-6-hydroxybenzylidene-2-thioxo-4-imidazolidinedione, 3-(3,5,5,8,8-Pentamethyl-5,6,7,8-tetrahydro-2-naphthyl)-4,6-dimethoxybenzylidene-2-thioxo-4-imidazolidinedione, 3-(3,5,5,8,8-Pentamethyl-5,6,7,8-tetrahydro-2-naphthyl)-4,6-dihydroxybenzylidene-2-thioxo-4-imidazolidinedione, 3-(1,4-Diisopropyl-6-methyl-1,2,3,4-tetrahydro-7-quinoxalinyl)-4-methoxybenzylidene-2-thioxo-4-imidazolidinedione, 3-(5,5,8,8-Tetramethyl-5,6,7,8-tetrahydro-2-naphthyl)-2,4-dimethoxybenzylidene-2-thioxo-4-imidazolidinedione, 3-(5,5,8,8-Tetramethyl-5,6,7,8-tetrahydro-2-naphthyl)-4-methoxybenzylidene-2-thioxo-4-imidazolidinedione, 3-(1-Isopropyl-7-methyl-1,2,3,4-tetrahydro-6-quinolinyl)-4-methoxybenzylidene-2-thioxo-4-imidazolidinedione, 3-(3,5,5,8,8-Pentamethyl-5,6,7,8-tetrahydro-2-naphthyl)-4,5-dimethoxybenzylidene-2-thioxo-4-imidazolidinedione, 3-(3,5,5,8,8-Pentamethyl-5,6,7,8-tetrahydro-2-naphthyl)-4-hydroxybenzylidene-2-thioxo-4-imidazolidinedione, 3-(3,5,5,8,8-Pentamethyl-5,6,7,8-tetrahydro-2-naphthyl)-4-methoxy-5-fluorobenzylidene-2-thioxo-4-imidazolidinedione, 3-(3,5,5,8,8-Pentamethyl-5,6,7,8-tetrahydro-2-naphthyl)-4-methoxy-2,5-difluorobenzylidene-2-thioxo-4-imidazolidinedione, 3-(3,5,5,8,8-Pentamethyl-5,6,7,8-tetrahydro-2-naphthyl)-4-methoxybenzylidene-2,4-imidazolidinedione, 3-(3,5,5,8,8-Pentamethyl-5,6,7,8-tetrahydro-2-naphthyl)-2-fluoro-4-methoxybenzylidene-2,4-imidazolidinedione, 5-(3,5,5,8,8-Pentamethyl-5,6,7,8-tetrahydro-2-naphthyl)-6-methoxy-3-pyridylidene-2,4-imidazolidinedione, 6-(3,5,5,8,8-Pentamethyl-5,6,7,8-tetrahydro-2-naphthyl)-5-methoxy-2-pyridylidene-2,4-imidazolidinedione, 3-(3,5,5,8,8-Pentamethyl-5,6,7,8-tetrahydro-2-naphthyl)-4-methoxy-6-hydroxybenzylidene-2,4-imidazolidinedione, 3-(3,5,5,8,8-Pentamethyl-5,6,7,8-tetrahydro-2-naphthyl)-4,6-dimethoxybenzylidene-2,4-imidazolidinedione, 3-(3,5,5,8,8-Pentamethyl-5,6,7,8-tetrahydro-2-naphthyl)-4,6-dihydroxybenzylidene-2,4-imidazolidinedione, 3-(1,4-Diisopropyl-6-methyl-1,2,3,4-tetrahydro-7-quinoxalinyl)-4-methoxybenzylidene-2,4-imidazolidinedione, 3-(5,5,8,8-Tetramethyl-5,6,7,8-tetrahydro-2-naphthyl)-2,4-dimethoxybenzylidene-2,4-imidazolidinedione, 3-(5,5,8,8-Tetramethyl-5,6,7,8-tetrahydro-2-naphthyl)-4-methoxybenzylidene-2,4-imidazolidinedione, 3-(1-Isopropyl-7-methyl-1,2,34-tetrahydro-6-quinolinyl)-4-methoxybenzylidene-2,4-imidazolidinedione, 3-(3,5,5,8,8-Pentamethyl-5,6,7,8-tetrahydro-2-naphthyl)-4,5-dimethoxybenzylidene-2,4-imidazolidinedione, 3-(3,5,5,8,8-Pentamethyl-5,6,7,8-tetrahydro-2-naphthyl)-4-hydroxybenzylidene-2,4-imidazolidinedione, 3-(3,5,5,8,8-Pentamethyl-5,6,7,8-tetrahydro-2-naphthyl)-4-methoxy-5-fluorobenzylidene-2,4-imidazolidinedione, 3-(3,5,5,8,8-Pentamethyl-5,6,7,8-tetrahydro-2-naphthyl)-4-methoxy-2,5-difluorobenzylidene-2,4-imidazolidinedione, 3-[(3,5,5,8,8-Pentamethyl-5,6,7,8-tetrahydro-2-naphthyl)-4-methoxybenzyl]-2-thioxo-4-imidazolidinedione, 3-[(3,5,5,8,8-Pentamethyl-5,6,7,8-tetrahydro-2-naphthyl)-2-fluoro-4-methoxybenzyl)]-2-thioxo-4-imidazolidinedione, 5-[(3,5,5,8,8-Pentamethyl-5,6,7,8-tetrahydro-2-naphthyl)-6-methoxy-3-pyridylmethylene]-2-thioxo-4-imidazolidinedione, 6-[(3,5,5,8,8-Pentamethyl-5,6,7,8-tetrahydro-2-naphthyl)-5-methoxy-2-pyridylmethylene]-2-thioxo-4-imidazolidinedione, 3-(3,5,5,8,8-Pentamethyl-5,6,7,8-tetrahydro-2-naphthyl)-4-methoxy-6-hydroxybenzyl-2-thioxo-4-imidazolidinedione, 3-(3,5,5,8,8-Pentamethyl-5,6,7,8-tetrahydro-2-naphthyl)-4,6-dimethoxybenzyl-2-thioxo-4-imidazolidinedione, 3-(3,5,5,8,8-Pentamethyl-5,6,7,8-tetrahydro-2-naphthyl)-4,6-dihydroxybenzyl-2-thioxo-4-imidazolidinedione, 3-(1,4-Diisopropyl-6-methyl-1,2,3,4-tetrahydro-7-quinoxalinyl)-4-methoxybenzyl-2-thioxo-4-imidazolidinedione, 3-(5,5,8,8-Tetramethyl-5,6,7,8-tetrahydro-2-naphthyl)-2,4-dimethoxybenzyl-2-thioxo-4-imidazolidinedione, 3-(5,5,8,8-Tetramethyl-5,6,7,8-tetrahydro-2-naphthyl)-4-methoxybenzyl-2-thioxo-4-imidazolidinedione, 3-(1-Isopropyl-7-methyl-1,2,3,4-tetrahydro-6-quinolinyl)-4-methoxybenzyl-2-thioxo-4-imidazolidinedione, 3-(3,5,5,8,8-Pentamethyl-5,6,7,8-tetrahydro-2-naphthyl)-4,5-dimethoxybenzyl-2-thioxo-4-imidazolidinedione, 3-(3,5,5,8,8-Pentamethyl-5,6,7,8-tetrahydro-2-naphthyl)-4-hydroxybenzyl-2-thioxo-4-imidazolidinedione, 3-(3,5,5,8,8-Pentamethyl-5,6,7,8-tetrahydro-2-naphthyl)-4-methoxy-5-fluorobenzyl-2-thioxo-4-imidazolidinedione, 3-(3,5,5,8,8-Pentamethyl-5,6,7,8-tetrahydro-2-naphthyl)-4-methoxy-2,5-difluorobenzyl-2-thioxo-4-imidazolidinedione, 3-[(3,5,5,8,8-Pentamethyl-5,6,7,8-tetrahydro-2-naphthyl)-4-methoxybenzyl]-2,4-imidazolidinedione, 3-[(3,5,5,8,8-Pentamethyl-5,6,7,8-tetrahydro-2-naphthyl)-2-fluoro-4-methoxybenzyl)]-2,4-imidazolidinedione, 5-[(3,5,5,8,8-Pentamethyl-5,6,7,8-tetrahydro-2-naphthyl)-6-methoxy-3-pyridylmethylene]-2,4-imidazolidinedione, 6-[(3,5,5,8,8-Pentamethyl-5,6,7,8-tetrahydro-2-naphthyl)-5-methoxy-2-pyridylmethylene]-2,4-imidazolidinedione, 3-(3,5,5,8,8-Pentamethyl-5,6,7,8-tetrahydro-2-naphthyl)-4-methoxy-6-hydroxybenzyl-2,4-imidazolidinedione, 3-(3,5,5,8,8-Pentamethyl-5,6,7,8-tetrahydro-2-naphthyl)-4,6-dimethoxybenzyl-2,4-imidazolidinedione, 3-(3,5,5,8,8-Pentamethyl-5,6,7,8-tetrahydro-2-naphthyl)-4,6-dihydroxybenzyl-2,4-imidazolidinedione, 3-(1,4-Diisopropyl-6-methyl-1,2,3,4-tetrahydro-7-quinoxalinyl)-4-methoxybenzyl-2,4-imidazolidinedione, 3-(5,5,8,8-Tetramethyl-5,6,7,8-tetrahydro-2-naphthyl)-2,4-dimethoxybenzyl-2,4-imidazolidinedione, 3-(5,5,8,8-Tetramethyl-5,6,7,8-tetrahydro-2-naphthyl)-4-methoxybenzyl-2,4-imidazolidinedione, 3-(1-Isopropyl-7-methyl-1,2,3,4-tetrahydro-6-quinolinyl)-4-methoxybenzyl-2,4-imidazolidinedione, 3-(3,5,5,8,8-Pentamethyl-5,6,7,8-tetrahydro-2-naphthyl)-4,5-dimethoxybenzyl-2,4-imidazolidinedione, 3-(3,5,5,8,8-Pentamethyl-5,6,7,8-tetrahydro-2-naphthyl)-4-hydroxybenzyl-2,4-imidazolidinedione, 3-(3,5,5,8,8-Pentamethyl-5,6,7,8-tetrahydro-2-naphthyl)-4-methoxy-5-fluorobenzyl-2,4-imidazolidinedione, 3-(3,5,5,8,8-Pentamethyl-5,6,7,8-tetrahydro-2-naphthyl)-4-methoxy-2,5-difluorobenzyl-2,4-imidazolidinedione, 3-(3,5,5,8,8-Pentamethyl-5,6,7,8-tetrahydro-2-naphthyl)-4-trifluoromethoxybenzylidene-2,4-thiazolidinedione,
3-(3,5,5,8,8-Pentamethyl-5,6,7,8-tetrahydro-2-naphthyl)-4-dimethylaminobenzylidene-2,4-thiazolidinedione,
3-(3,5,5,8,8-Pentamethyl-5,6,7,8-tetrahydro-2-naphthyl)-4-chlorobenzylidene-2,4-thiazolidinedione,
3-(3,5,5,8,8-Pentamethyl-5,6,7,8-tetrahydro-2-naphthyl)-4-methylbenzylidene-2,4-thiazolidinedione,
3-(3,5,5,8,8-Pentamethyl-5,6,7,8-tetrahydro-2-naphthyl)-4-ethylbenzylidene-2,4-thiazolidinedione,
3-(3,5,5,8,8-Pentamethyl-5,6,7,8-tetrahydro-2-naphthyl)-4-trifluoromethylbenzylidene-2,4-thiazolidinedione,
3-(3,5,5,8,8-Pentamethyl-5,6,7,8-tetrahydro-2-naphthyl)-4-ethoxybenzylidene-2,4-thiazolidinedione,
3-(3,5,5,8,8-Pentamethyl-5,6,7,8-tetrahydro-2-naphthyl)-4-ethoxy-2-fluorobenzylidene-2,4-thiazolidinedione,
3-(3,5,5,8,8-Pentamethyl-5,6,7,8-tetrahydro-2-naphthyl)-4-isopropoxybenzylidene-2,4-thiazolidinedione,
3-(3,5,5,8,8-Pentamethyl-5,6,7,8-tetrahydro-2-naphthyl)-4-aminobenzylidene-2,4-thiazolidinedione,
3-(3,5,5,8,8-Pentamethyl-5,6,7,8-tetrahydro-2-naphthyl)-4-acetamidobenzylidene-2,4-thiazolidinedione,
3-(3,5,5,8,8-Pentamethyl-5,6,7,8-tetrahydro-2-naphthyl)-4-ethoxy-2,5-difluorobenzylidene-2,4-thiazolidinedione,
3-(3-Methoxy-5,5,8,8-tetramethyl-5,6,7,8-tetrahydro-2-naphthyl)-4-trifluoromethoxybenzylidene-2,4-thiazolidinedione,
3-(3-Dimethylamino-5,5,8,8-tetramethyl-5,6,7,8-tetrahydro-2-naphthyl)-4-trifluoromethoxybenzylidene-2,4-thiazolidinedione,
3-(3-Trifluoromethyl-5,5,8,8-tetramethyl-5,6,7,8-tetrahydro-2-naphthyl)-4-methoxybenzylidene-2,4-thiazolidinedione,
3-(3-Trifluoromethyl-5,5,8,8-tetramethyl-5,6,7,8-tetrahydro-2-naphthyl)-4-methylbenzylidene-2,4-thiazolidinedione,
3-(3-Trifluoromethyl-5,5,8,8-tetramethyl-5,6,7,8-tetrahydro-2-naphthyl)-4-ethylbenzylidene-2,4-thiazolidinedione,
3-(3-Trifluoromethyl-5,5,8,8-tetramethyl-5,6,7,8-tetrahydro-2-naphthyl)-4-trifluoromethoxybenzylidene-2,4-thiazolidinedione,
3-(3-Dimethylamino-5,5,8,8-tetramethyl-5,6,7,8-tetrahydro-2-naphthyl)-4-dimethylaminobenzylidene-2,4-thiazolidinedione,
3-(3-Trifluoromethyl-5,5,8,8-tetramethyl-5,6,7,8-tetrahydro-2-naphthyl)-4-chlorobenzylidene-2,4-thiazolidinedione,
3-(3,5,5,8,8-Pentamethyl-5,6,7,8-tetrahydro-2-naphthyl)-4-methylamino-5-bromobenzylidene-2,4-thiazolidinedione,
3-(3,5,5,8,8-Pentamethyl-5,6,7,8-tetrahydro-2-naphthyl)-4-acetoxybenzylidene-2,4-thiazolidinedione,
3-(3,5,5,8,8-Pentamethyl-5,6,7,8-tetrahydro-2-naphthyl)-2-fluoro-4-hydroxybenzylidene-2,4-thiazolidinedione,
3-(3,5,5,8,8-Pentamethyl-5,6,7,8-tetrahydro-2-naphthyl)-4-(1-propen-3-yl)-benzylidene-2,4-thiazolidinedione,
3-(3,5,5,8,8-Pentamethyl-5,6,7,8-tetrahydro-2-naphthyl)-4-hydroxy-5-fluorobenzylidene-2,4-thiazolidinedione,
3-(3,5,5,8,8-Pentamethyl-5,6,7,8-tetrahydro-2-naphthyl)-4-hydroxy-2,5-difluorobenzylidene-2,4-thiazolidinedione,
3-(3,5,5,8,8-Pentamethyl-5,6,7,8-tetrahydro-2-naphthyl)-4-methoxy-2,6-difluorobenzylidene-2,4-thiazolidinedione,
3-(3,5,5,8,8-Pentamethyl-5,6,7,8-tetrahydro-2-naphthyl)-4-methoxy-5,6-difluorobenzylidene-2,4-thiazolidinedione,
3-(3-Trifluoromethyl-5,5,8,8-tetramethyl-5,6,7,8-tetrahydro-2-naphthyl)-4-dimethylaminobenzylidene-2,4-thiazolidinedione, and
3-(3-Ethyl-5,5,8,8-tetramethyl-5,6,7,8-tetrahydro-2-naphthyl)-4-trifluoromethoxybenzylidene-2,4-thiazolidinedione.

The structures for these compounds are shown below:

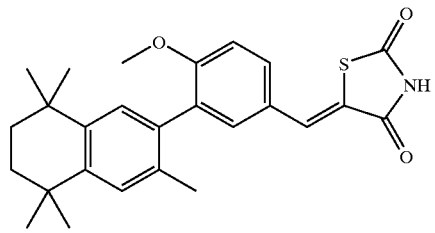

3-(3,5,5,8,8-Pentamethyl-5,6,7,8-tetrahydro-2-naphthyl)-4-methoxybenzylidene-2,4-thiazolidinedione

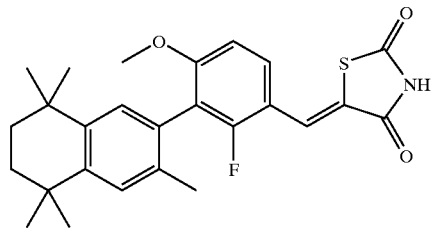

3-(3,5,5,8,8-Pentamethyl-5,6,7,8-tetrahydro-2-naphthyl)-2-fluoro-4-methoxybenzylidene-2,4-thiazolidinedione

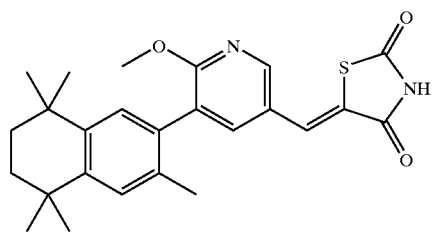

5-(3,5,5,8,8-Pentamethyl-5,6,7,8-tetrahydro-2-naphthyl)-6-methoxy-3-pyridylidene-2,4-thiazolidinedione

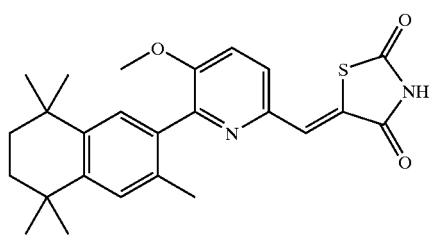

6-(3,5,5,8,8-Pentamethyl-5,6,7,8-tetrahydro-2-naphthyl)-5-methoxy-2-pyridylidene-2,4-thiazolidinedione

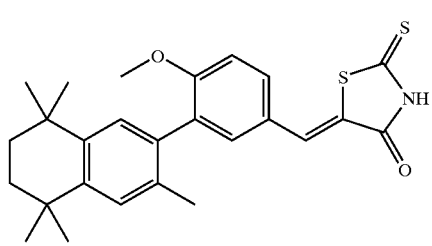

3-(3,5,5,8,8-Pentamethyl-5,6,7,8-tetrahydro-2-naphthyl)-4-methoxybenzylidene-2-thioxo-4-thiazolinedione

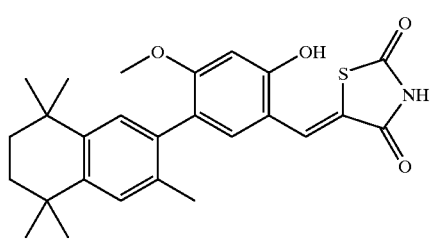

3-(3,5,5,8,8-Pentamethyl-5,6,7,8-tetrahydro-2-naphthyl)-4-methoxy-6-hydroxybenzylidene-2,4-thiazolidinedione

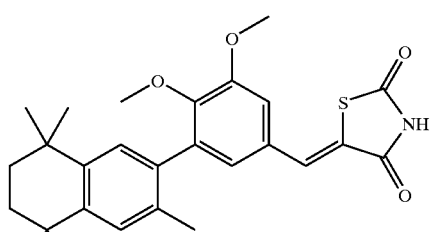

3-(3,5,5,8,8-Pentamethyl-5,6,7,8-tetrahydro-2-naphthyl)-4,5-dimethoxybenzylidene-2,4-thiazolidinedione

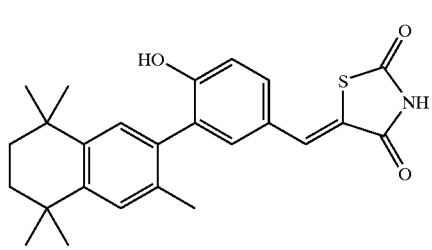

3-(3,5,5,8,8-Pentamethyl-5,6,7,8-tetrahydro-2-naphthyl)-4-hydroxybenzylidene-2,4-thiazolidinedione

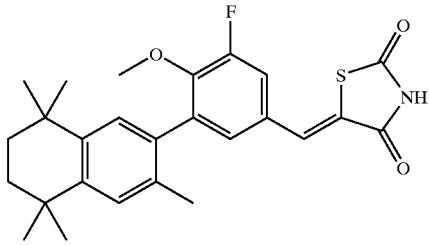

3-(3,5,5,8,8-Pentamethyl-5,6,7,8-tetrahydro-2-naphthyl)-4-methoxy-5-fluorobenzylidene-2,4-thiazolidinedione

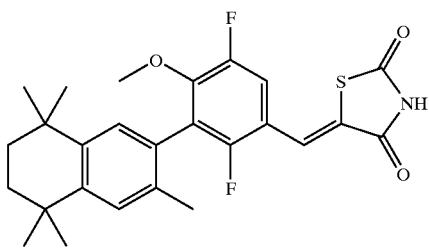

3-(3,5,5,8,8-Pentamethyl-5,6,7,8-tetrahydro-2-naphthyl)-4-methoxy-2,5-difluorobenzylidene-2,4-thiazolidinedione

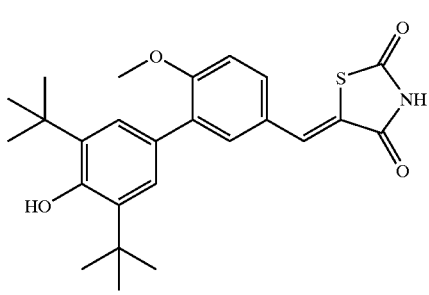

3-(3,5,-Di-t-butylphenyl)-4-methoxy-benzylidene-2,4-thiazolidinedione

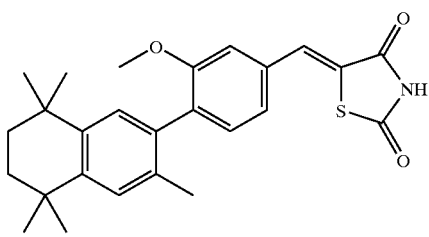

4-(3,5,5,8,8-Pentamethyl-5,6,7,8-tetrahydro-2-naphthyl)-3-methoxybenzylidene-2,4-thiazolidinedione

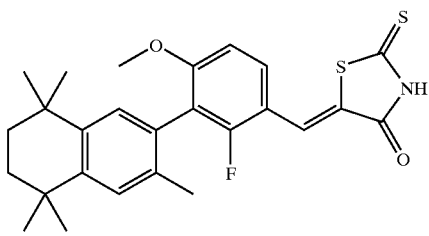

3-(3,5,5,8,8-Pentamethyl-5,6,7,8-tetrahydro-2-naphthyl)-2-fluoro-4-methoxybenzylidene-2-thioxo-4-thiazolidinedione -continued

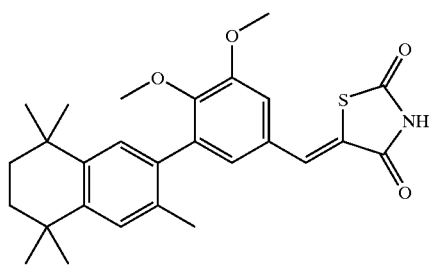

3-(3,5,5,8,8-Pentamethyl-5,6,7,8-tetrahydro-2-
naphthyl)-4,5-dimethoxybenzylidene-2,4-
thiazolidinedione

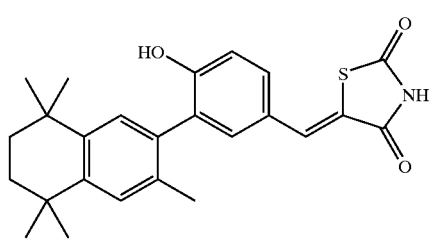

3-(3,5,5,8,8-Pentamethyl-5,6,7,8-tetrahydro-2-
naphthyl)-4-hydroxybenzylidene-2,4-
thiazolidinedione

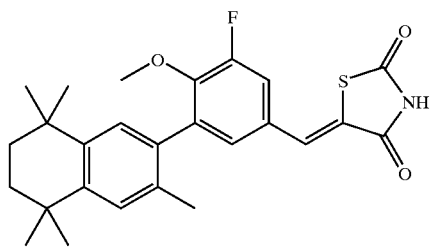

3-(3,5,5,8,8-Pentamethyl-5,6,7,8-tetrahydro-2-
naphthyl)-4-methoxy-5-fluorobenzylidene-2,4-
thiazolidinedione

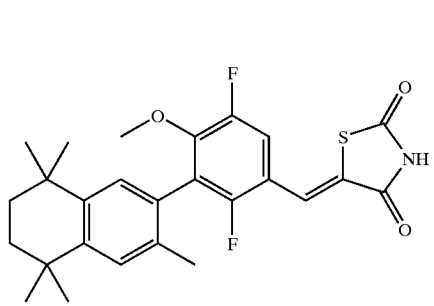

3-(3,5,5,8,8-Pentamethyl-5,6,7,8-tetrahydro-2-
naphthyl)-4-methoxy-2,5-difluorobenzylidene-
2,4-thiazolidinedione

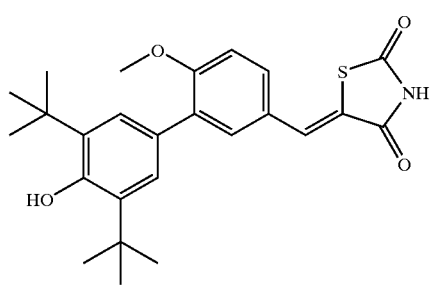

3-(3,5,-Di-t-butylphenyl-4-methoxy-
benzylidene-2,4-thiazolidinedione

-continued

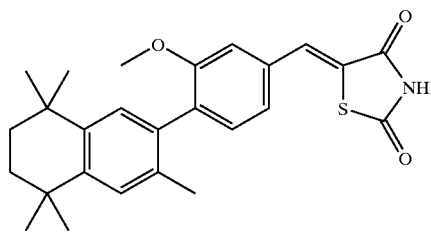

4-(3,5,5,8,8-Pentamethyl-5,6,7,8-tetrahydro-2-
naphthyl)-3-methoxybenzylidene-2,4-
thiazolidinedione

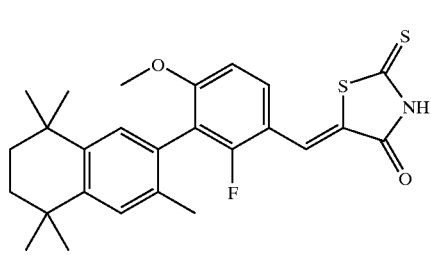

3-(3,5,5,8,8-Pentamethyl-5,6,7,8-tetrahydro-2-
naphthyl)-2-fluoro-4-methoxybenzylidene-2-
thioxo-4-thiazolidinedione

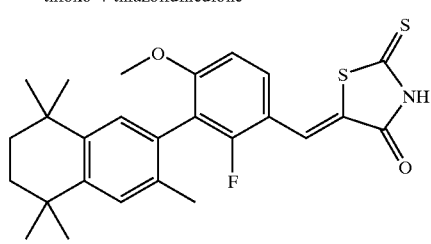

3-(3,5,5,8,8-Pentamethyl-5,6,7,8-tetrahydro-2-
naphthyl)-2-fluoro-4-methoxybenzylidene-2-
thioxo-4-thiazolidinedione

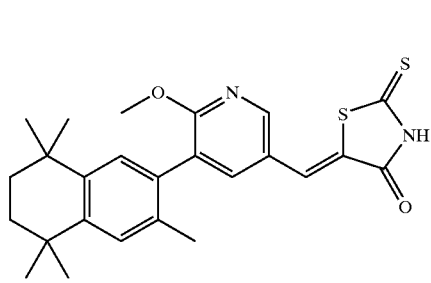

5-(3,5,5,8,8-Pentamethyl-5,6,7,8-tetrahydro-2-
naphthyl)-6-methoxy-3-pyridylidene-2-thioxo-
4-thiazolidinedione

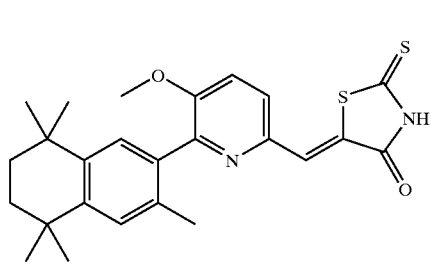

6-(3,5,5,8,8-Pentamethyl-5,6,7,8-tetrahydro-2-
naphthyl)-5-methoxy-2-pyridylidene-2-thioxo-
4-thiazolidinedione -continued

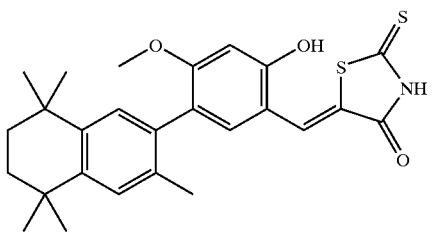

3-(3,5,5,8,8-Pentamethyl-5,6,7,8-tetrahydro-2-
naphthyl)-4-methoxy-6-hydroxybenzylidene-
2-thioxo-4-thiazolidinedione

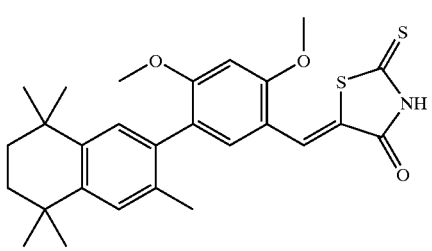

3-(3,5,5,8,8-Pentamethyl-5,6,7,8-tetrahydro-2-
naphthyl)-4,6-dimethoxybenzylidene-2-thioxo-
4-thiazolidinedione

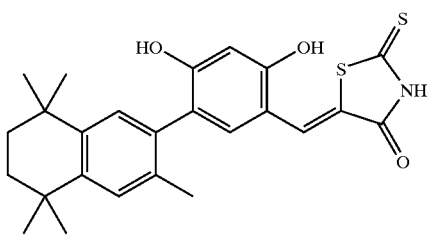

3-(3,5,5,8,8-Pentamethyl-5,6,7,8-tetrahydro-2-
naphthyl)-4,6-dihydroxybenzylidene-2-thioxo-
4-thiazolidinedione

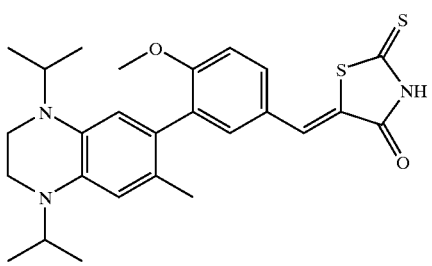

3-(1,4-Diisopropyl-6-methyl-1,2,3,4-tetrahydro-
7-quinoxalinyl)-4-methoxybenzylidene-2-thioxo-
4-thiazolidinedione

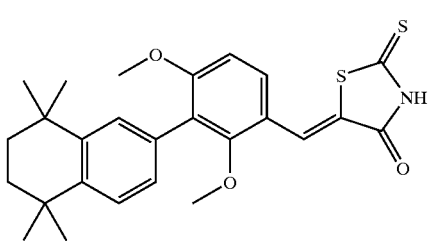

3-(5,5,8,8-Tetramethyl-5,6,7,8-tetrahydro-2-
naphthyl)-2,4-dimethoxybenzylidene-2-
thioxo-4-thiazolidinedione -continued

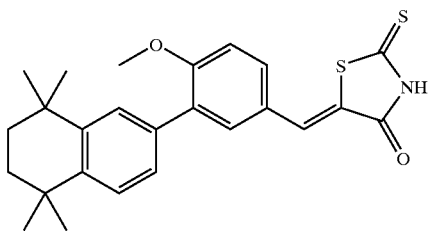

3-(5,5,8,8-Tetramethyl-5,6,7,8-tetrahydro-2-
naphthyl)-4-methoxybenzylidene-2-thioxo-4-
thiazolidinedione

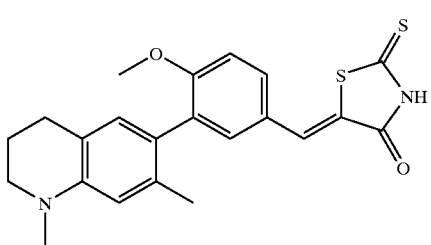

3-(l-Isopropyl-7-methyl-1,2,3,4-tetrahydro-6-
quinolinyl)-4-methoxybenzylidene-2-thioxo-
4-thiazolindinedione

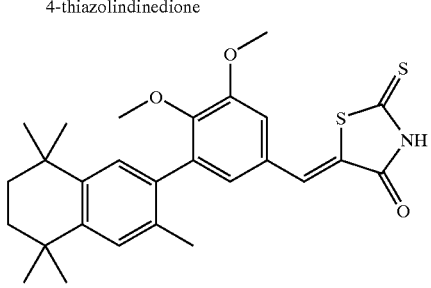

3-(3,5,5,8,8-Pentamethyl-5,6,7,8-tetrahydro-2-
naphthyl)-4,5-dimethoxybenzylidene-2-thioxo-
4-thiazolidinedione

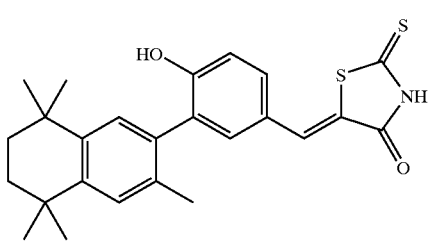

3-(3,5,5,8,8-Pentamethyl-5,6,7,8-tetrahydro-2-
naphthyl)-4-hydroxybenzylidene-2-thioxo-4-
thiazolidinedione

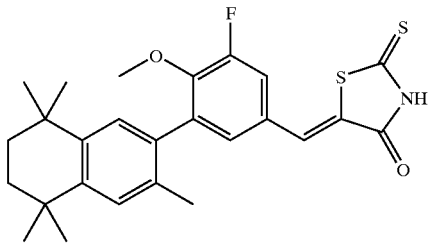

3-(3,5,5,8,8-Pentamethyl-5,6,7,8-tetrahydro-
2-naphthyl)-4-methoxy-5-fluorobenzylidene-
2-thioxo-4-thiazolidinedione

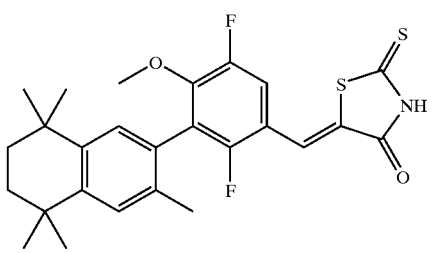

3-(3,5,5,8,8-Pentamethyl-5,6,7,8-tetrahydro-2-naphthyl)-4-methoxy-2,5-difluorobenzylidene-2-thioxo-4-thiazolidinedione

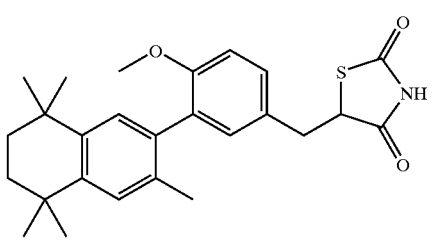

3-[(3,5,5,8,8-Pentamethyl-5,6,7,8-tetrahydro-2-naphthyl)-4-methoxybenzyl]-2,4-thiazolidinedione

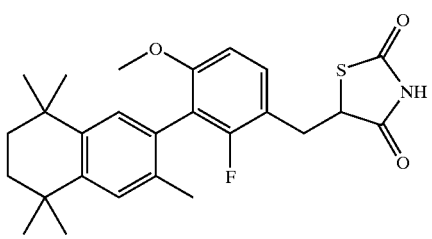

3-[(3,5,5,8,8-Pentamethyl-5,6,7,8-tetrahydro-2-naphthyl)-2-fluoro-4-methoxybenzyl)]-2,4-thiazolidinedione

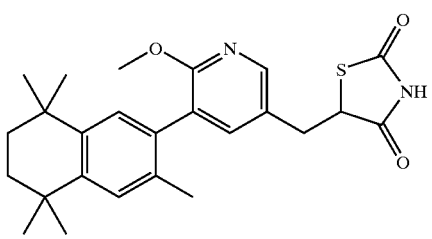

5-[(3,5,5,8,8-Pentamethyl-5,6,7,8-tetrahydro-2-naphthyl)-6-methoxy-3-pyridylmethylene]-2,4-thiazolidinedione

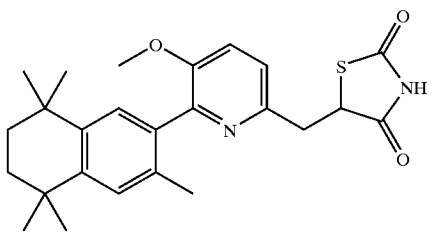

6-[(3,5,5,8,8-Pentamethyl-5,6,7,8-tetrahydro-2-naphthyl)-5-methoxy-2-pyridylmethylene]-2,4-thiazolidinedione

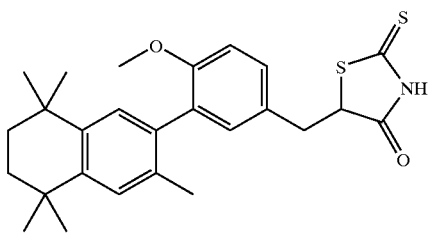

3-(3,5,5,8,8-Pentamethyl-5,6,7,8-tetrahydro-2-naphthyl)-4-methoxybenyzyl-2-thioxo-4-thiazolidinedione

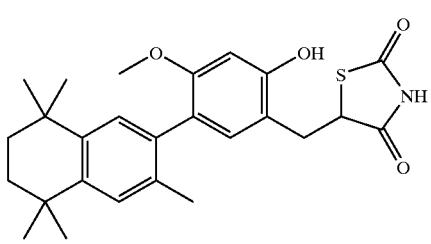

3-(3,5,5,8,8-Pentamethyl-5,6,7,8-tetrahydro-2-naphthyl)-4-methoxy-6-hydroxybenzyl-2,4-thiazolidinedione

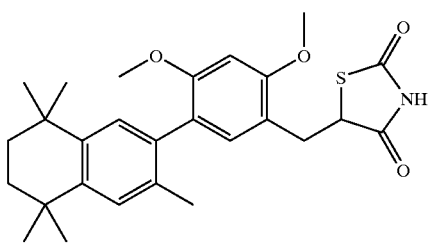

3-(3,5,5,8,8-Pentamethyl-5,6,7,8-tetrahydro-2-naphthyl)-4,6-dimethoxybenzyl-2,4-thiazolidinedione

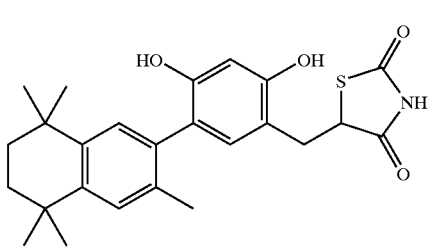

3-(3,5,5,8,8-Pentamethyl-5,6,7,8-tetrahydro-2-naphthyl)-4,6-dihydroxybenzyl-2,4-thiazolidinedione

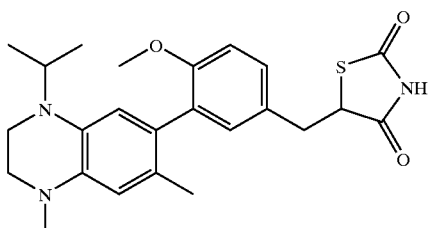

3-(1,4-Diisopropyl-6-methyl-1,2,3,4-tetrahydro-7-quinoxalinyl)-4-methoxybenzyl-2,4-thiazolidinedione

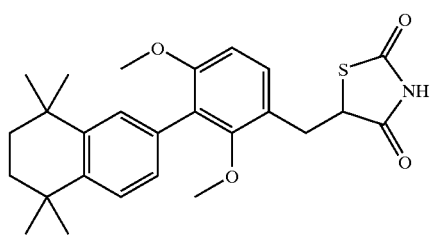

3-(5,5,8,8-Tetramethyl-5,6,7,8-tetrahydro-2-naphthyl)-2,4-dimethoxybenzyl-2,4-thiazolidinedione

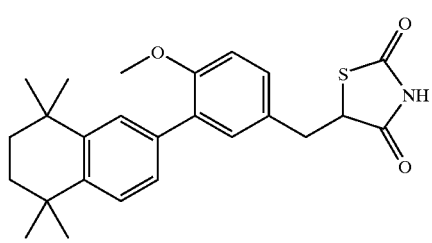

3-(5,5,8,8-Tetramethyl-5,6,7,8-tetrahydro-2-naphthyl)-4-methoxybenzyl-2,4-thiazolidinedione

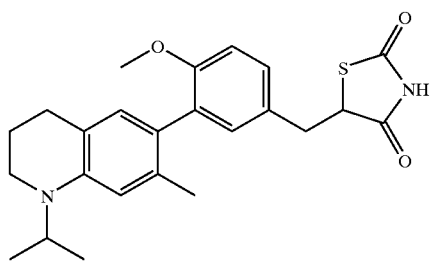

3-(1-Isopropyl-7-methyl-1,2,3,4-tetrahydro-6-quinolinyl)-4-methoxybenzyl-2,4-thiazolidinedione

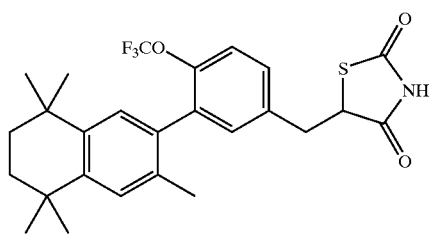

3-(3,5,5,8,8-Pentamethyl-5,6,7,8-tetrahydro-2-naphthyl)-4-trifluoromethoxybenzyl-2,4-thiazolidinedione

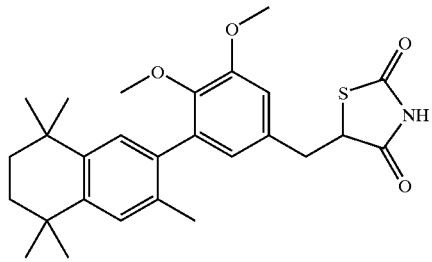

3-(3,5,5,8,8-Pentamethyl-5,6,7,8-tetrahydro-2-naphthyl)-4,5-dimethoxybenzyl-2,4-thiazolidinedione

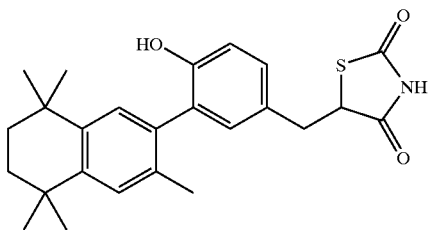

3-(3,5,5,8,8-Pentamethyl-5,6,7,8-tetrahydro-2-naphthyl)-4-hydroxybenzyl-2,4-thiazolidinedione

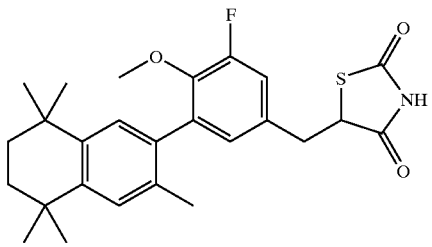

3-(3,5,5,8,8-Pentamethyl-5,6,7,8-tetrahydro-2-naphthyl)-4-methoxy-5-fluorobenzyl-2,4-thiazolidinedione

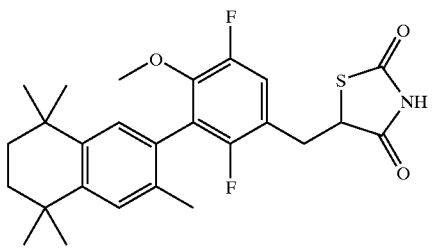

3-(3,5,5,8,8-Pentamethyl-5,6,7,8-tetrahydro-2-naphthyl)-4-methoxy-2,5-difluorobenzyl-2,4-thiazolidinedione

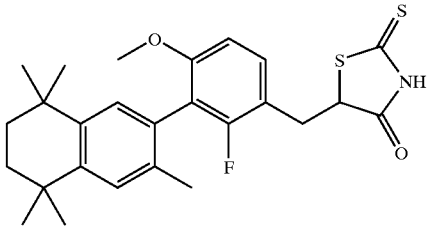

3-(3,5,5,8,8-Pentamethyl-5,6,7,8-tetrahydro-2-naphthyl)-2-fluoro-4-methoxybenzyl-2-thioxo-4-thiazolidinedione

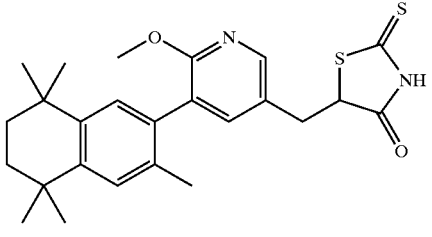

5-(3,5,5,8,8-Pentamethyl-5,6,7,8-tetrahydro-2-naphthyl)-6-methoxy-3-pyridylmethylene-2-thioxo-4-thiazolidinedione

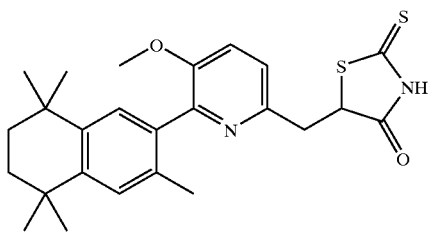

6-(3,5,5,8,8-Pentamethyl-5,6,7,8-tetrahydro-2-naphthyl)-5-methoxy-2-pyridylmethylene-2-thioxo-4-thiazolidinedione

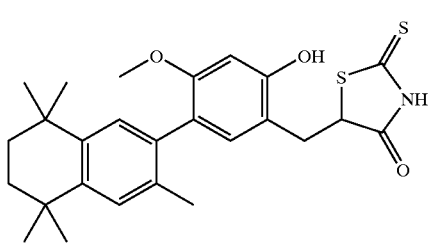

3-(3,5,5,8,8-Pentamethyl-5,6,7,8-tetrahydro-2-naphthyl)-4-methoxy-6-hydroxybenzyl-2-thioxo-4-thiazolidinedione

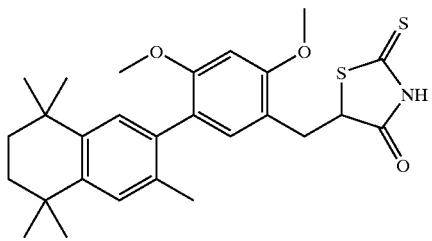

3-(3,5,5,8,8-Pentamethyl-5,6,7,8-tetrahydro-2-naphthyl)-4,6-dimethoxybenzyl-2-thioxo-4-thiazolidinedione

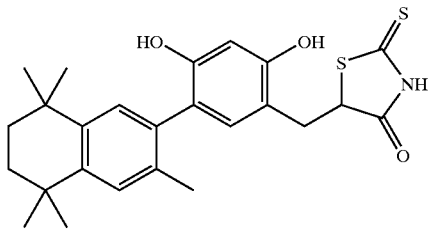

3-(3,5,5,8,8-Pentamethyl-5,6,7,8-tetrahydro-2-naphthyl)-4,6-dihydroxybenzyl-2-thioxo-4-thiazolidinedione

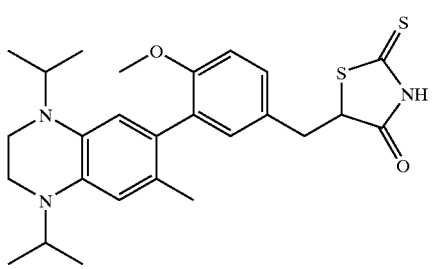

3-(1,4-Diisopropyl-6-methyl-1,2,3,4-tetrahydro-7-quinoxalinyl)-4-methoxybenzyl-2-thioxo-4-thiazolidinedione

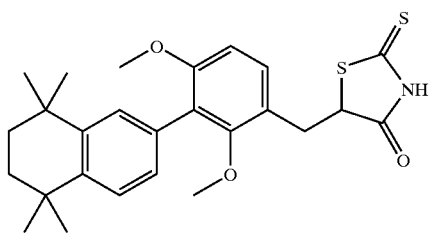

3-(5,5,8,8-Tetramethyl-5,6,7,8-tetrahydro-2-napthyl)-2,4-dimethoxybenzyl-2-thioxo-4-thiazolidinedione

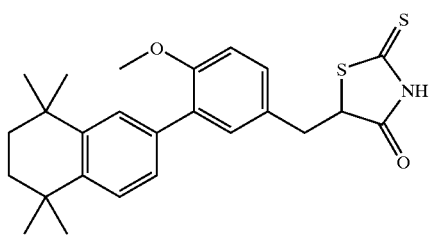

3-(5,5,8,8-Tetramethyl-5,6,7,8-tetrahydro-2-napthyl)-4-methoxybenzyl-2-thioxo-4-thiazolidinedione

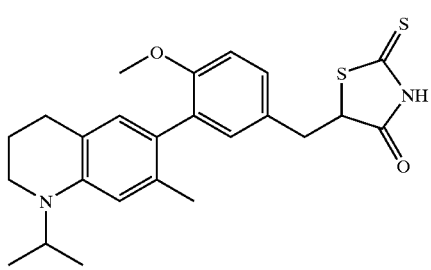

3-(1-Isopropyl-7-methyl-1,2,3,4-tetrahydro-6-quinolinyl)-4-methoxybenzyl-2-thioxo-4-thiazolidinedione

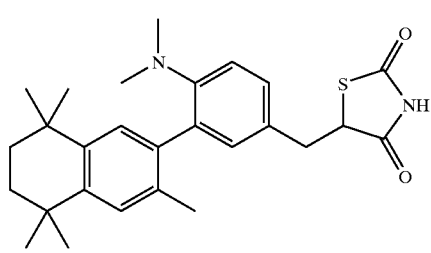

3-(3,5,5,8,8-Pentamethyl-5,6,7,8-tetrahydro-2-naphthyl)-4-dimethylaminobenzyl-2,4-thiazolidinedione

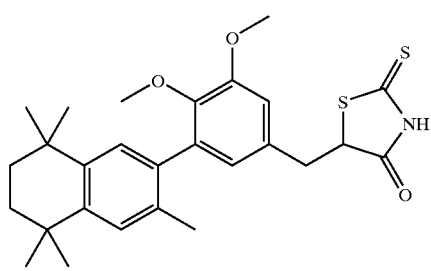

3-(3,5,5,8,8-Pentamethyl-5,6,7,8-tetrahydro-2-naphthyl)-4,5-dimethoxybenzyl-2-thioxo-4-thiazolidinedione

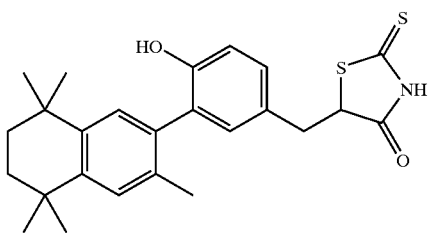

3-(3,5,5,8,8-Pentamethyl-5,6,7,8-tetrahydro-2-naphthyl)-4-hydroxybenzyl-2-thioxo-4-thiazolidinedione

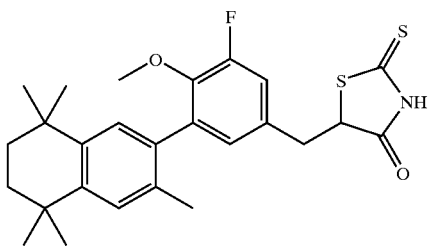

3-(3,5,5,8,8-Pentamethyl-5,6,7,8-tetrahydro-2-naphthyl)-4-methoxy-5-fluorobenzyl-2-thioxo-4-thiazolidinedione

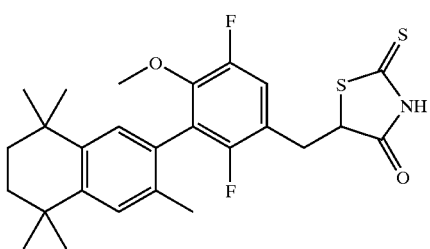

3-(3,5,5,8,8-Pentamethyl-5,6,7,8-tetrahydro-2-naphthyl)-4-methoxy-2,5-difluorobenzyl-2-thioxo-4-thiazolidinedione

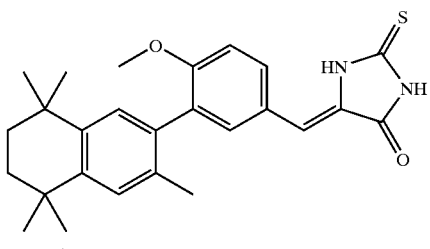

3-(3,5,5,8,8-Pentamethyl-5,6,7,8-tetrahydro-2-naphthyl)-4-methoxybenzylidene-2-thioxo-4-imidazolidinedione

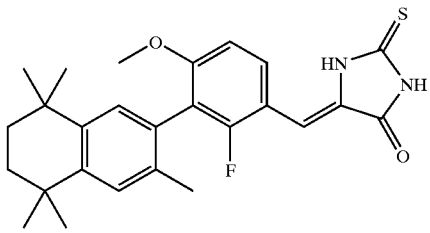

3-(3,5,5,8,8-Pentamethyl-5,6,7,8-tetrahydro-2-naphthyl)-2-fluoro-4-methoxybenzylidene-2-thioxo-4-imidazolidinedione

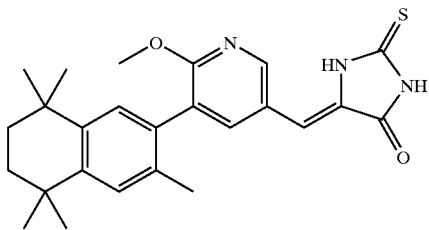

5-(3,5,5,8,8-Pentamethyl-5,6,7,8-tetrahydro-2-naphthyl)-6-methoxy-3-pyridylidene-2-thioxo-4-imidazolidinedione

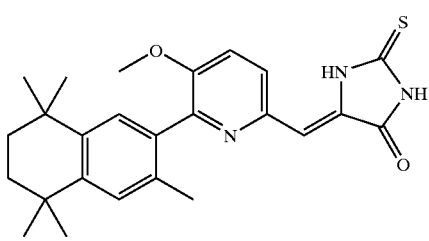

6-(3,5,5,8,8-Pentamethyl-5,6,7,8-tetrahydro-2-naphthyl)-5-methoxy-2-pyridylidene-2-thioxo-4-imidazolidinedione

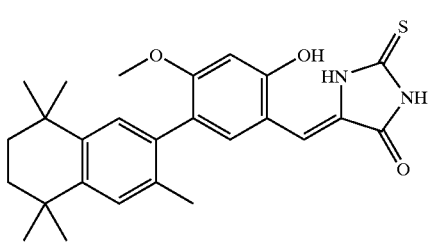

3-(3,5,5,8,8-Pentamethyl-5,6,7,8-tetrahydro-2-naphthyl)-4-methoxy-6-hydroxybenzylidene-2-thioxo-4-imidazolidinedione

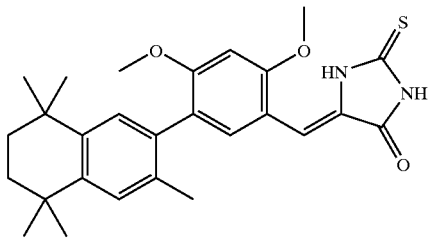

3-(3,5,5,8,8-Pentamethyl-5,6,7,8-tetrahydro-2-naphthyl)-4,6-dimethoxybenzylidene-2-thioxo-4-imidazolidinedione

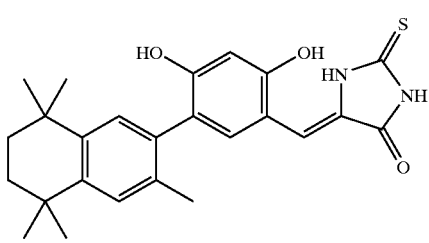

3-(3,5,5,8,8-Pentamethyl-5,6,7,8-tetrahydro-2-naphthyl)-4,6-dihydroxybenzylidene-2-thioxo-4-imidazolidinedione

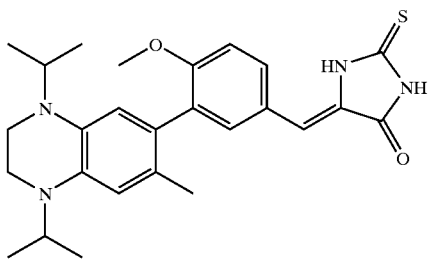

3-(1,4-Diisopropyl-6-methyl-1,2,3,4-tetrahydro-7-quinoxalinyl-4-methoxybenzylidene-2-thioxo-4-imidazolidinedione

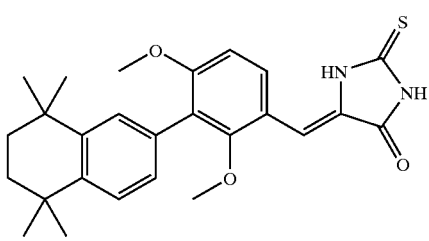

3-(5,5,8,8-Tetramethyl-5,6,7,8-tetrahydro-2-naphthyl)-2,4-dimethoxybenzylidene-2-thioxo-4-imidazolidinedione

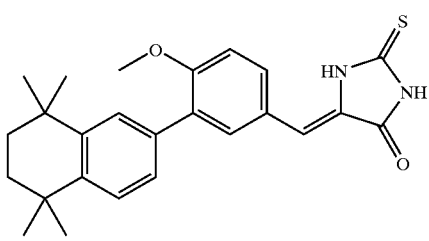

3-(5,5,8,8-Tetramethyl-5,6,7,8-tetrahydro-2-naphthyl)-4-methoxybenzylidene-2-thioxo-4-imidazolidinedione

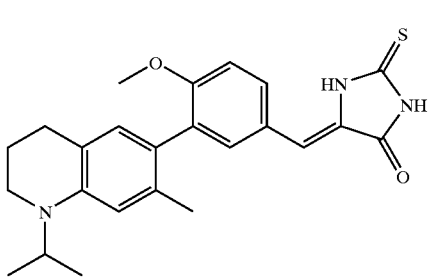

3-(l-Isopropyl-7-methyl-1,2,3,4-tetrahydro-6-quinolinyl)-4-methoxybenzylidene-2-thioxo-4-imidazolidinedione

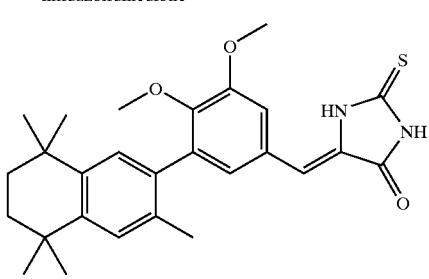

3-(3,5,5,8,8-Pentamethyl-5,6,7,8-tetrahydro-2-naphthyl)-4,5-dimethoxybenzylidene-2-thioxo-4-imidazolidinedione

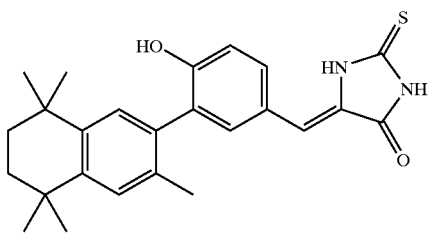

3-(3,5,5,8,8-Pentamethyl-5,6,7,8-tetrahydro-2-naphthyl)-4-hydroxybenzylidene-2-thioxo-4-imidazolinedione

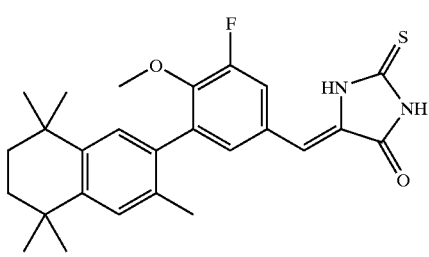

3-(3,5,5,8,8-Pentamethyl-5,6,7,8-tetrahydro-2-naphthyl)-4-methoxy-5-fluorobenzylidene-2-thioxo-4-imidazolidinedione

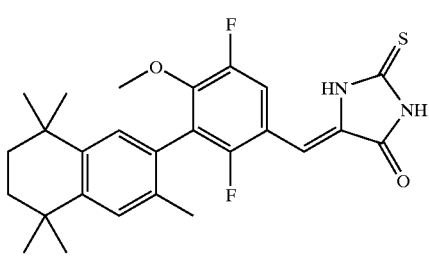

3-(3,5,5,8,8-Pentamethyl-5,6,7,8-tetrahydro-2-naphthyl)-4-methoxy-2,5-difluorobenzylidene-2-thioxo-4-imidazolidinedione

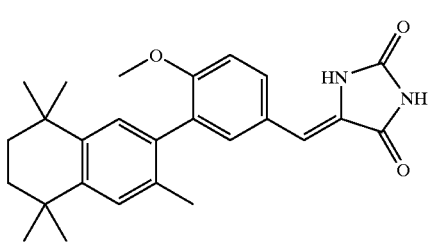

3-(3,5,5,8,8-Pentamethyl-5,6,7,8-tetrahydro-2-naphthyl)-4-methoxybenzylidene-2,4-imidazolidinedione

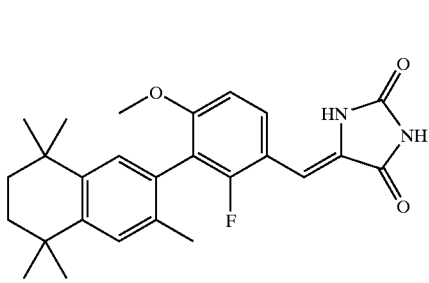

3-(3,5,5,8,8-Pentamethyl-5,6,7,8-tetrahydro-2-naphthyl)-2-fluoro-4-methoxybenzylidene-2,4-imidazolidinedione

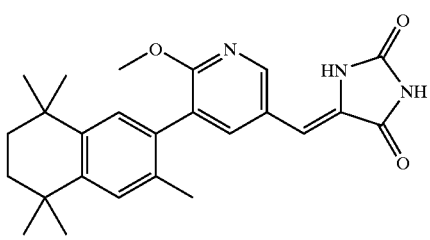

5-(3,5,5,8,8-Pentamethyl-5,6,7,8-tetrahydro-2-naphthyl)-6-methoxyl-3-pyridylidene-2,4-imidazolidinedione

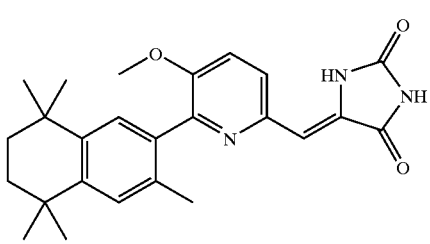

6-(3,5,5,8,8-Pentamethyl-5,6,7,8-tetrahydro-2-naphthyl)-5-methoxyl-2-pyridylidene-2,4-imidazolidinedione

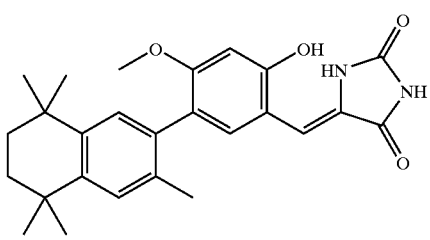

3-(3,5,5,8,8-Pentamethyl-5,6,7,8-tetrahydro-2-naphthyl)-4-methoxyl-6-hydroxybenzylidene-2,4-imidazolinedione

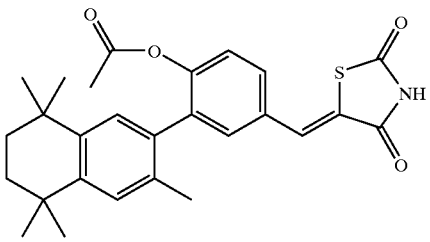

3-(3,5,5,8,8-Pentamethyl-5,6,7,8-tetrahydro-2-naphthyl)-4-acetoxybenzylidene-2,4-thizolidinedione

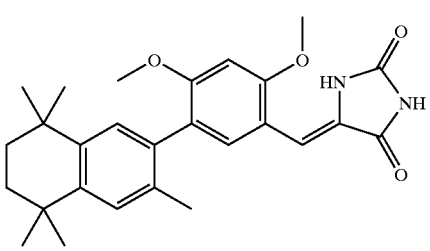

3-(3,5,5,8,8-Pentamethyl-5,6,7,8-tetrahydro-2-naphthyl)-4,6-dimethoxybenzylidene-2,4-imidazolidinedione

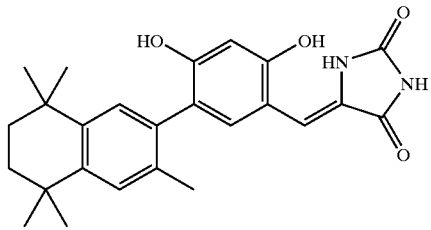

3-(3,5,5,8,8-Pentamethyl-5,6,7,8-tetrahydro-2-naphthyl)-4,6-dihydroxybenzylidene-2,4-imidazolidinedione

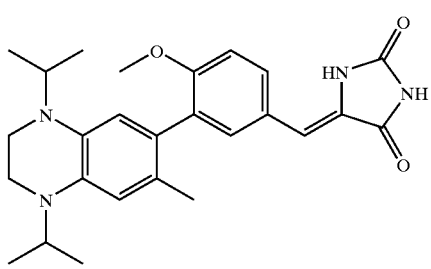

3-(1,4-Diisopropyl-6-methyl-1,2,3,4-tetrahydro-7-quinoxalinyl)-4-methoxybenzylidene-2,4-imidazolidinedione

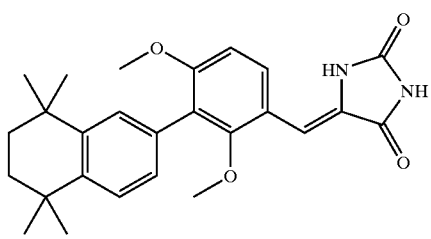

3-(5,5,8,8-Tetramethyl-5,6,7,8-tetrahydro-2-naphthyl)-2,4-dimethoxybenzylidene-2,4-imidazolidinedione

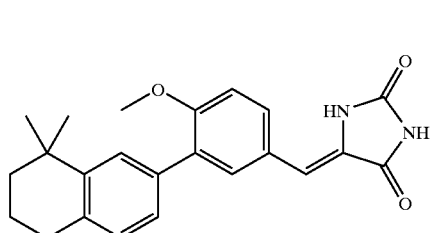

3-(5,5,8,8-Tetramethyl-5,6,7,8-tetrahydro-2-naphthyl)-4-methoxybenzylidene-2,4-imidazolidinedione

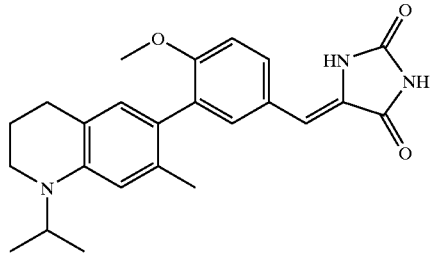

3-(1-Isopropyl-7-methyl-1,2,3,4-tetrahydro-6-quinolinyl)-4-methoxybenzylidene-2,4-imidazolidinedione

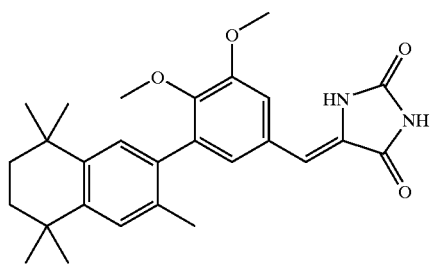

3-(3,5,5,8,8-Pentamethyl-5,6,7,8-tetrahydro-2-naphthyl)-4,5-dimethoxybenzylidene-2,4-imidazolidinedione

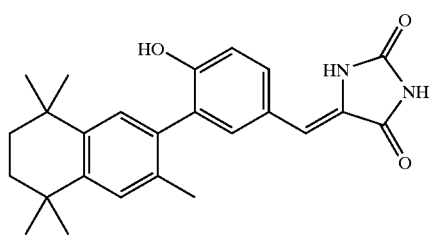

3-(3,5,5,8,8-Pentamethyl-5,6,7,8-tetrahydro-2-naphthyl)-4-hydroxybenzylidene-2,4-imidazolidinedione

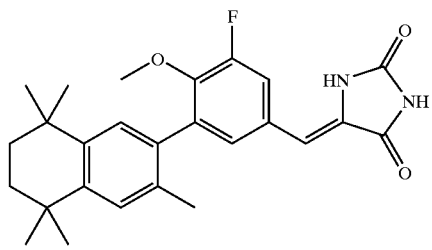

3-(3,5,5,8,8-Pentamethyl-5,6,7,8-tetrahydro-2-naphthyl)-4-methoxy-5-fluorobenzylidene-2,4-imidazolidinedione

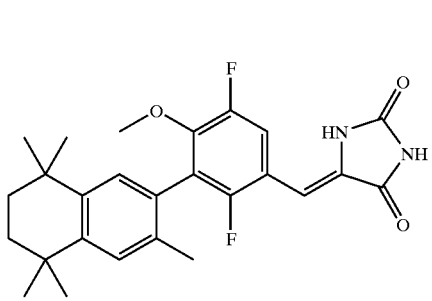

3-(3,5,5,8,8-Pentamethyl-5,6,7,8-tetrahydro-2-naphthyl)-4-methoxy-2,5-difluorobenzylidene-2,4-imidazolidinedione

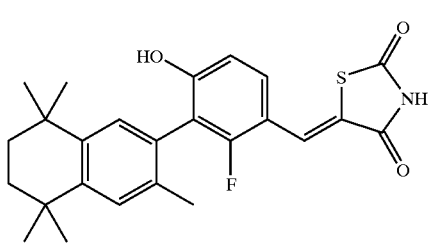

3-(3,5,5,8,8-Pentamethyl-5,6,7,8-tetrahydro-2-naphthyl)-2-fluoro-4-hydroxybenzylidene-2,4-thiazolidinedione

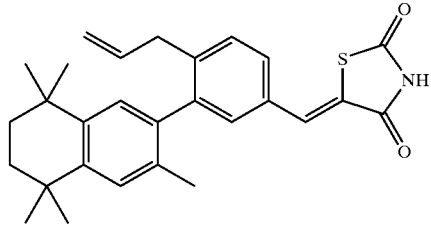

3-(3,5,5,8,8-Pentamethyl-5,6,7,8-tetrahydro-2-naphthyl)-4-(1-propen-3-yl)-benzylidene-2,4-thiazolidinedione

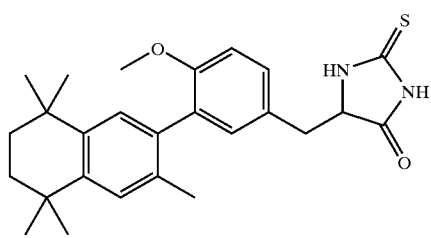

3-[(3,5,5,8,8-Pentamethyl-5,6,7,8-tetrahydro-2-naphthyl)-4-methoxybenzyl]-2-thioxo-4-imidazolidinedione

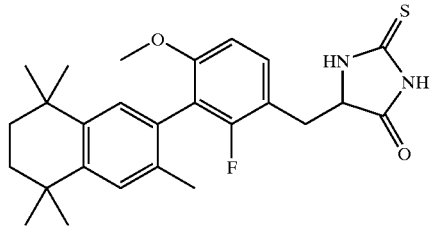

3-[(3,5,5,8,8-Pentamethyl-5,6,7,8-tetrahydro-2-naphthyl)-2-fluoro-4-methoxybenzyl)]-2-thioxo-4-imidazolidinedione

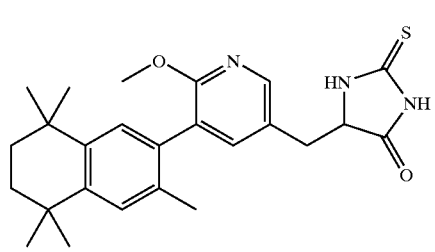

5-[(3,5,5,8,8-Pentamethyl-5,6,7,8-tetrahydro-2-naphthyl)-6-methoxyl-3-pyridylmethylene]-2-thioxo-4-imidazolidinedione

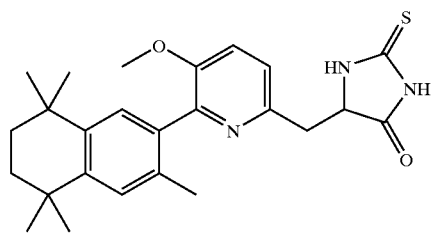

6-[(3,5,5,8,8-Pentamethyl-5,6,7,8-tetrahydro-2-naphthyl)-5-methoxy-2-pyridylmethylene]-2-thioxo-4-imidazolidinedione -continued

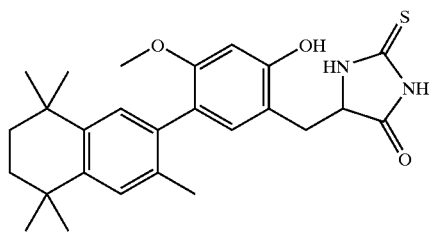

3-(3,5,5,8,8-Pentamethyl-5,6,7,8-tetrahydro-2-
naphthyl)-4-methoxyl-6-hydroxybenzyl-2-
thioxo-4-imidazolidinedione

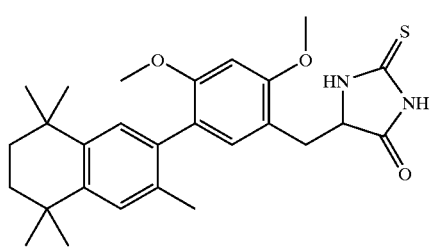

3-(3,5,5,8,8-Pentamethyl-5,6,7,8-tetrahydro-2-
naphthyl)-4,6-dimethoxybenzyl-2-thioxo-4-
imidazolidinedione,

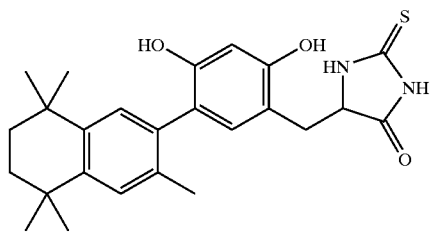

3-(3,5,5,8,8-Pentamethyl-5,6,7,8-tetrahydro-2-
naphthyl)-4,6-dihydroxybenzyl-2-thioxo-4-
imidazolidinedione

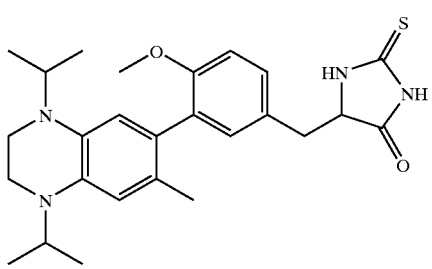

3-(1,4-Diisopropyl-6-methyl-1,2,3,4-tetrahydro-
7-quinoxalinyl)-4-methoxbenzyl-2-thioxo-4-
imidazolidinedione

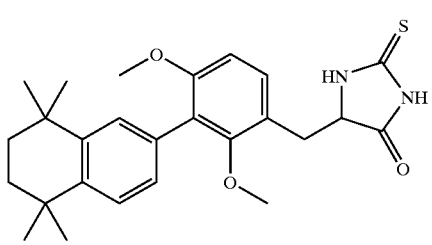

3-(5,5,8,8-Tetramethyl-5,6,7,8-tetrahydro-2-
naphthyl)-2,4-dimethoxybenzyl-2-thioxo-4-
imidazolidinedione

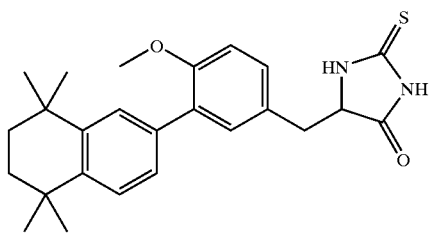

3-(5,5,8,8-Tetramethyl-5,6,7,8-tetrahydro-2-
naphthyl)-4-methoxybenzyl-2-thioxo-4-
imidazolidinedione

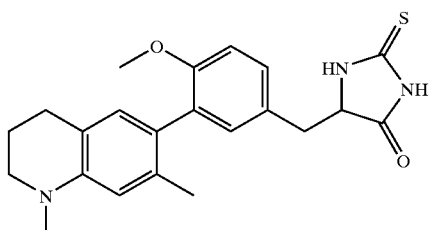

3-(1-Isopropyl-7-methyl-1,2,3,4-tetrahydro-6-
quinolinyl)-4-methoxybenzyl-2-thioxo-4-
imidazolidinedione,

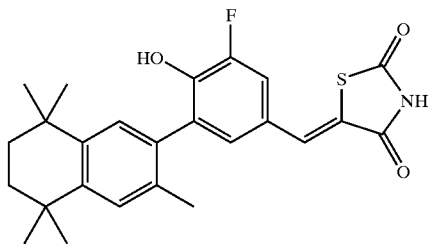

3-(3,5,5,8,8-Pentamethyl-5,6,7,8-tetrahydro-2-
naphthyl)-4-hydroxy-5-fluorobenzylidene-2,4-
thiazolidinedione

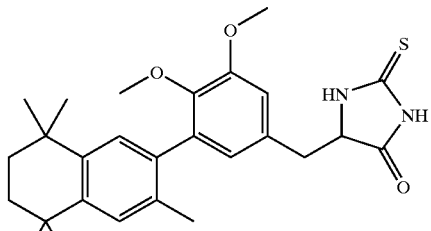

3-(3,5,5,8,8-Pentamethyl-5,6,7,8-tetrahydro-2-
naphthyl)-4,5-dimethoxybenzyl-2-thioxo-4-
imidazolidinedione

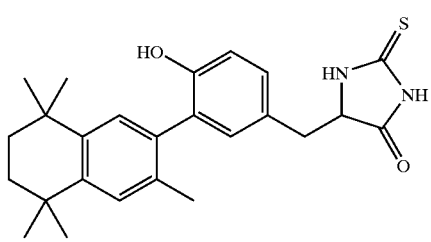

3-(3,5,5,8,8-Pentamethyl-5,6,7,8-tetrahydro-2-
naphthyl)-4-hydroxybenzyl-2-thioxo-4-
imidazolidinedione, -continued

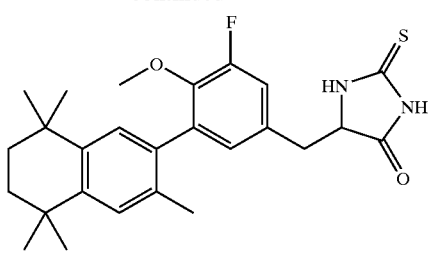

3-(3,5,5,8,8-Pentamethyl-5,6,7,8-tetrahydro-2-
naphthyl)-4-methoxy-5-fluorobenzyl-2-thioxo-
4-imidazolidinedione,

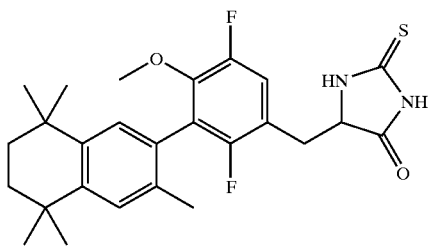

3-(3,5,5,8,8-Pentamethyl-5,6,7,8-tetrahydro-2-
naphthyl)-4-methoxy-2,5-difluorobenzyl-2-
thioxo-4-imidazolidinedione,

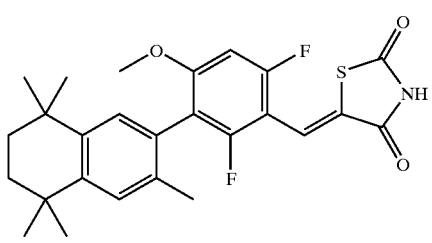

3-(3,5,5,8,8-Pentamethyl-5,6,7,8-tetrahydro-2-
naphthyl)-4-methoxy-2,6-difluorobenzylidene-
2,4-thiazolidinedione

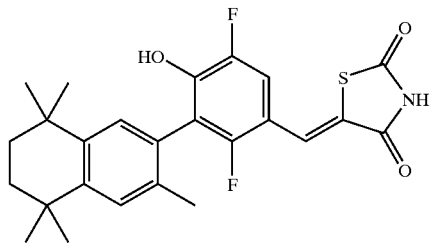

3-(3,5,5,8,8-Pentamethyl-5,6,7,8-tetrahydro-2-
naphthyl)-4-hydroxy-2,5-difluorobenzylidene-
2,4-thiazolidinedione

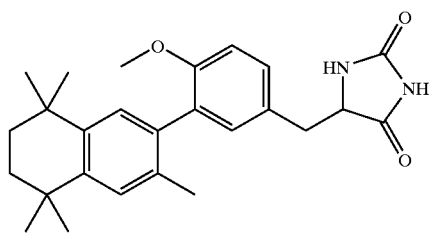

3-[(3,5,5,8,8-Pentamethyl-5,6,7,8-tetrahydro-2-
naphthyl]-4-methoxybenzyl]-2,4-
imidazolidinedione -continued

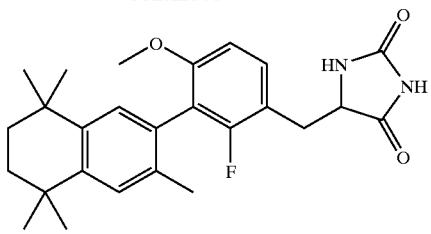

3-[(3,5,5,8,8-Pentamethyl-5,6,7,8-tetrahydro-2-
naphthyl)-2-fluoro-4-methoxybenzyl)]-2,4-
imidazolidinedione

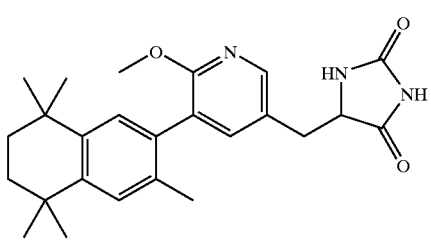

5-[(3,5,5,8,8-Pentamethyl-5,6,7,8-tetrahydro-2-
naphthyl)-6-methoxy-3-pyridylmethylene]-2,4-
imidazolidinedione

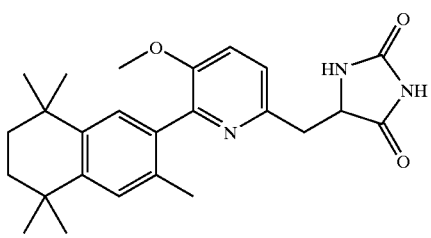

6-[(3,5,5,8,8-Pentamethyl-5,6,7,8-tetrahydro-2-
naphthyl)-5-methoxy-2-pyridylmethylene]-2,4-
imidazolidinedione

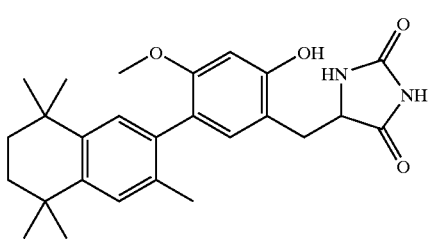

3-(3,5,5,8,8-Pentamethyl-5,6,7,8-tetrahydro-2-
naphthyl)-4-methoxy-6-hydroxybenzyl-2,4-
imidazolidinedione

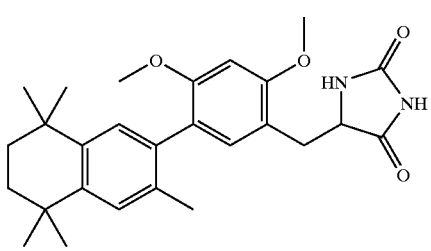

3-(3,5,5,8,8-Pentamethyl-5,6,7,8-tetrahydro-2-
naphthyl)-4,6-dimethoxybenzyl-2,4-
imidazolidinedione -continued

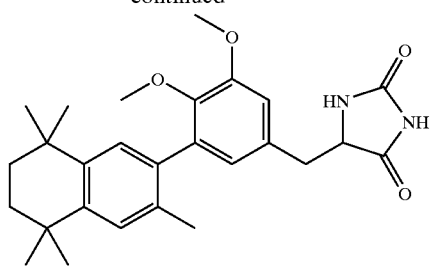

3-(3,5,5,8,8-Pentamethyl-5,6,7,8-tetrahydro-2-
naphthyl)-4,5-dimethoxybenzyl-2,4-
imidazolidinedion,

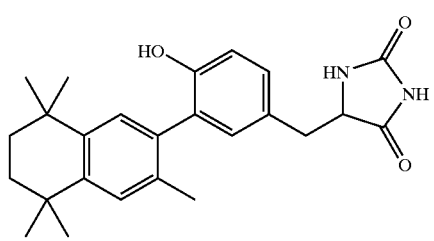

3-(3,5,5,8,8-Pentamethyl-5,6,7,8-tetrahydro-2-
naphthyl)-4-hydroxybenzyl-2,4-
imidazolidinedione

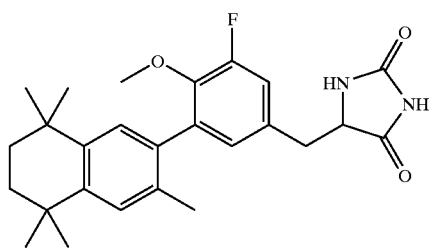

3-(3,5,5,8,8-Pentamethyl-5,6,7,8-tetrahydro-
2-naphthyl)-4-methoxy-5-fluorobenzyl-2,4-
imidazolidinedione

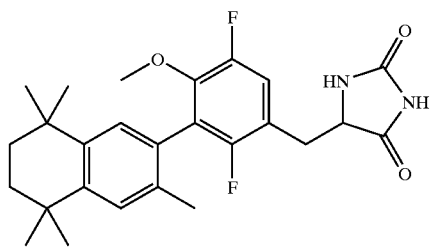

3-(3,5,5,8,8-Pentamethyl-5,6,7,8-tetrahydro-
2-naphthyl)-4-methoxy-2,5-difluorobenzyl-
2,4-imidazolidinedione

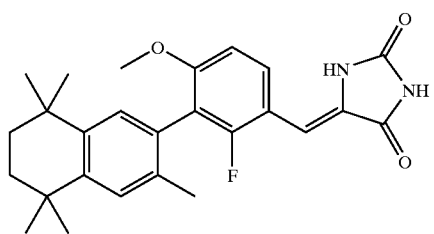

3-(3,5,5,8,8-Pentamethyl-5,6,7,8-tetrahydro-2-
naphthyl)-2-fluoro-4-methoxybenzylidene-
2,4-imidazolidinedione -continued

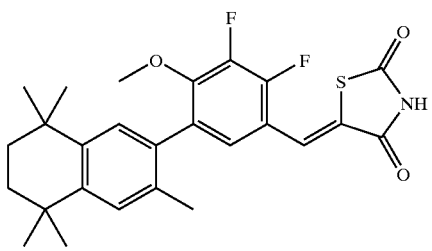

3-(3,5,5,8,8-Pentamethyl-5,6,7,8-tetrahydro-2-
naphthyl)-4-methoxy-5,6-difluorobenzylidene-
2,4-thiazolidinedione

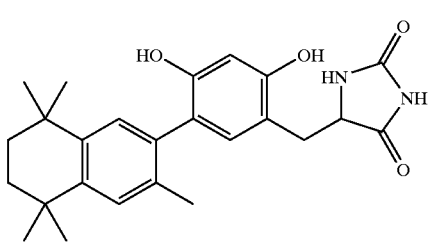

3-(3,5,5,8,8-Pentamethyl-5,6,7,8-tetrahydro-2-
naphthyl)-4,6-dihydroxybenzyl-2,4-
imidazolidinedione

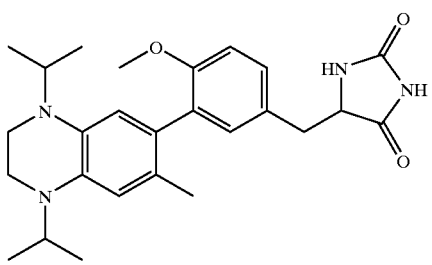

3-(1,4-Diisopropyl-6-methyl-1,2,3,4-tetrahydro-
7-quinoxalinyl)-4-methoxybenzyl-2,4-
imidazolidinedione

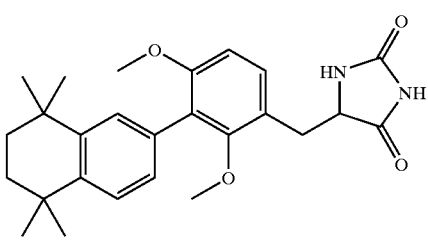

3-(5,5,8,8-Tetramethyl-5,6,7,8-tetrahydro-2-
naphthyl)-2,4-dimethoxybenzyl-2,4-
imidazolidinedione

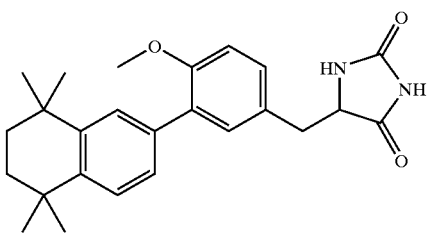

3-(5,5,8,8-Tetramethyl-5,6,7,8-tetrahydro-2-
naphthyl)-2,4-methoxybenzyl-2,4-
imidazolidinedione -continued

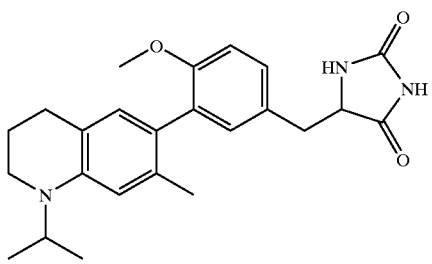

3-(1-Isopropyl-7-methyl-1,2,3,4-tetrahydro-6-quinolinyl)-4-methoxybenzyl-2,4-imidazolidinedione

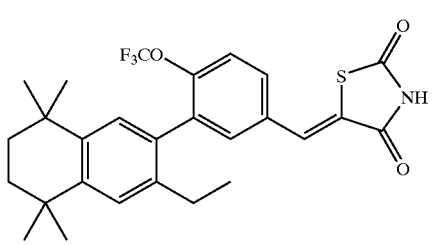

3-(3-Ethyl-5,5,8,8-tetramethyl-5,6,7,8-tetrahydro-2-naphthyl)-4-trifluoromethoxybenzylidene-2,4-thiazolidinedione

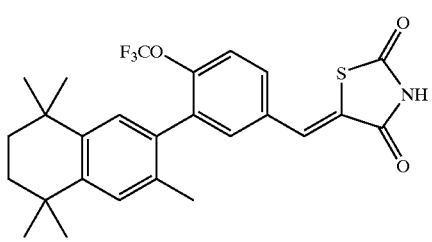

3-(3,5,5,8,8-Pentamethyl-5,6,7,8-tetrahydro-2-naphthyl)-4-trifluoromethoxybenzylidene-2,4-thiazolidinedione

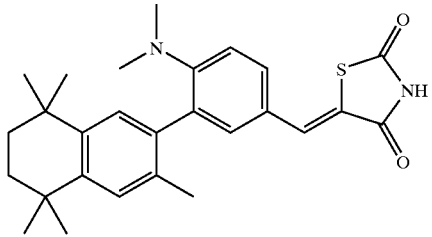

3-(3,5,5,8,8-Pentamethyl-5,6,7,8-tetrahydro-2-naphthyl)-4-dimethylaminobenzylidene-2,4-thiazolidinedione

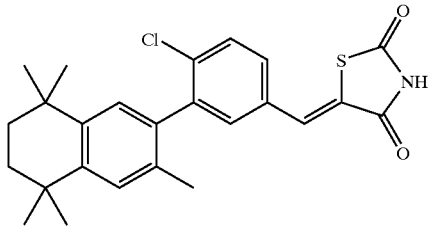

3-(3,5,5,8,8-Pentamethyl-5,6,7,8-tetrahydro-2-naphthyl)-4-chlorobenzylidene-2,4-thiazolidinedione -continued

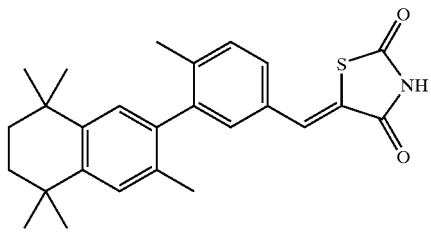

3-(3,5,5,8,8-Pentamethyl-5,6,7,8-tetrahydro-2-naphthyl)-4-methylbenzylidene-2,4-thiazolidindione

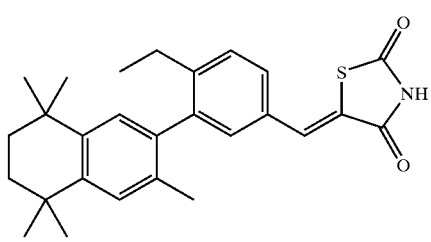

3-(3,5,5,8,8-Pentamethyl-5,6,7,8-tetrahydro-2-naphthyl)-4-ethylbenzylidene-2,4-thiazolidinedione

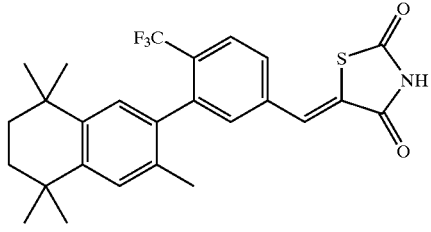

3-(3,5,5,8,8-Pentamethyl-5,6,7,8-tetrahydro-2-naphthyl)-4-trifluoromethylbenzylidene-2,4-thiazolidinedione

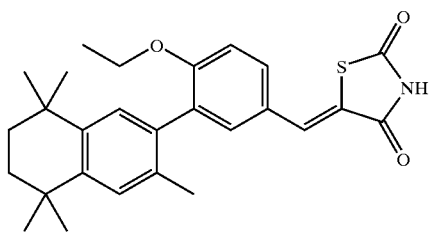

3-(3,5,5,8,8-Pentamethyl-5,6,7,8-tetrahydro-2-naphthyl)-4-ethoxybenzylidene-2,4-thiazolidinedione

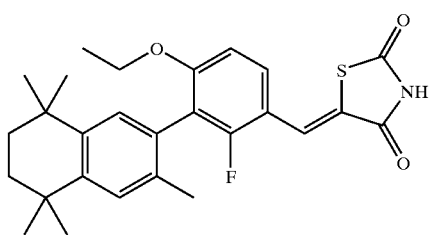

3-(3,5,5,8,8-Pentamethyl-5,6,7,8-tetrahydro-2-naphthyl)-4-ethoxy-2-fluorobenzylidene-2,4-thiazolidinedione -continued

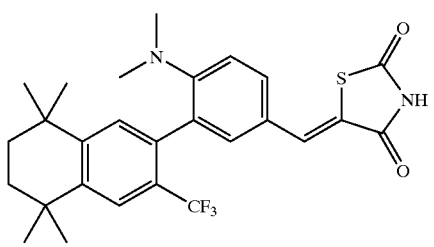

3-(3-Trifluoro-5,5,8,8-tetramethyl-5,6,7,8-
tetrahydro-2-naphthyl)-4-dimethylamino
benzylidene-2,4-thiazolidinedione

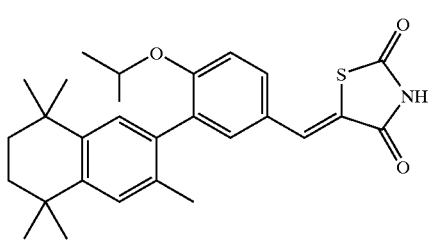

3-(3,5,5,8,8-Pentamethyl-5,6,7,8-tetrahydro-2-
naphthyl)-4-isopropoxybenzylidene-2,4-
thiazolidindione

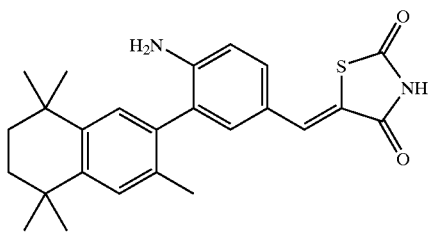

3-(3,5,5,8,8-Pentamethyl-5,6,7,8-tetrahydro-2-
napthyl)-4-aminobenzylidene-2,4-thiazolidine
dione

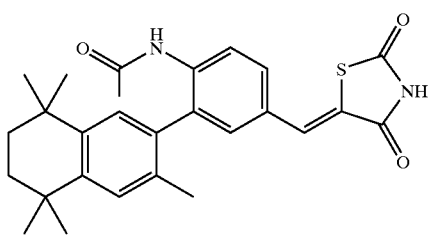

3-(3,5,5,8,8-Pentamethyl-5,6,7,8-tetrahydro-2-
napthyl)-4-acetamidobenzylidene-2,4-
thiazolidinedione

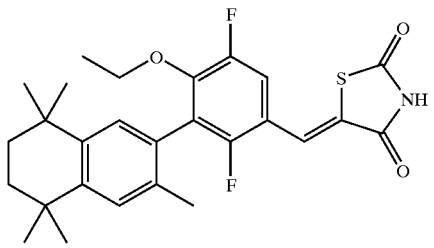

3-(3,5,5,8,8-Pentamethyl-5,6,7,8-tetrahydro-2-
naphthyl)-4-ethoxy-2,5-fluorobenzylidene-2,4-
thiazolidinedione -continued

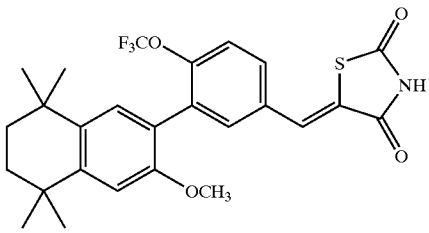

3-(3-Methoxy-5,5,8,8-tetramethyl-5,6,7,8-tetra
hydro-2-naphthyl)-4-trifluoromethoxy-
benzylidene-2,4-thiazolidinedione

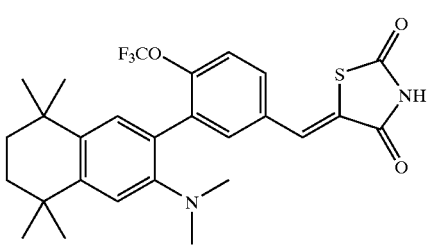

3-(3-Dimethylamino-5,5,8,8-tetramethyl-5,6,7,8-
tetrahydro-2-naphthyl)-4-trifluoromethoxybenzyl
idene-2,4-thiazolidinedione

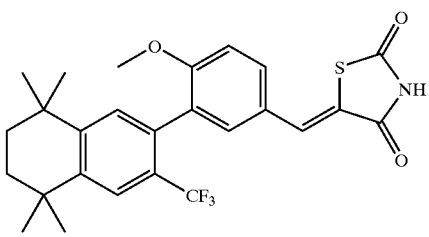

3-(3-Trifluoromethyl-5,5,8,8-tetramethyl-5,6,7,8-
tetrahydro-2-naphthyl)-4-methoxybenzylidene-
2,4-thiazolidinedione

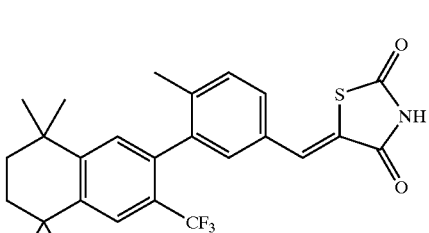

3-(3-Trifluoromethyl-5,5,8,8-tetramethyl-5,6,7,8-
tetrahydro-2-naphthyl)-4-methylbenzylidene-2,4-
thiazolidinedione

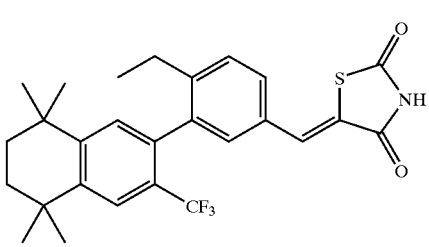

3-(3-Trifluoromethyl-5,5,8,8-tetramethyl-5,6,7,8-
tetrahydro-2-naphthyl)-4-ethylbenzylidene-2,4-
thiazolidinedione -continued

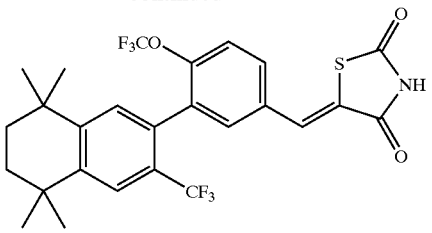

3-(3-Trifluoromethyl-5,5,8,8-tetramethyl-5,6,7,8-
tetrahydro-2-naphthyl)-4-trifluoromethoxy-
benzylidene-2,4-thiazolidinedione

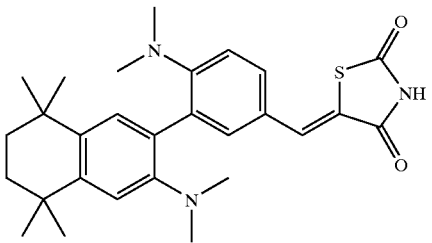

3-(3-Dimethylamino-5,5,8,8-tetramethyl-5,6,7,
8-tetrahydro-2-naphthyl)-4-dimethylamino-
benzylidene-2,4-thiazolidinedione

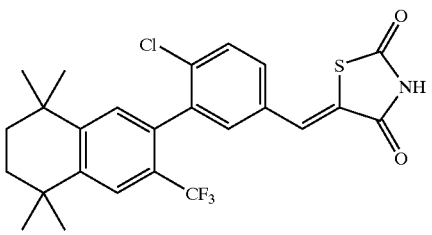

3-(3-Trifluoromethyl-5,5,8,8-tetramethyl-5,6,7,8-
tetrahydro-2-naphthyl)-4-chlorobenzylidene-2,4-
thiazolidinedione

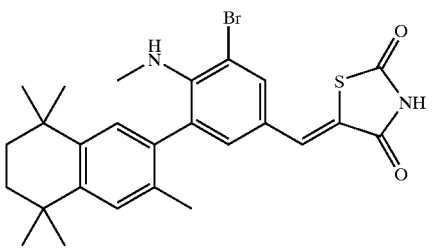

3-(3,5,5,8,8-Pentamethyl-5,6,7,8-tetrahydro-2-
naphthyl)-4-methylamino-5-bromobenzylidene-
2,4-thiazolidinedione In some embodiments of Formula (I) wherein A is present, (i.e. 0 when n is 1), $R_1$ and $R_2$ together with the aromatic ring form a substituted cycloalkyl optionally comprising 1 or 2 nitrogen heteroatoms; and $R_3$ is alkyl or substituted alkyl. In other embodiments wherein A is —$CR_6R_7$—, $R_6$ and $R_7$ are independently or together alkyl; or $R_6$ and $R_7$ together form a substituted or unsubstituted cycloalkyl optionally comprising 1 or 2 oxygen heteroatoms, or more preferably a 1,3-dioxolane ring. Still with respect to when n is 1, preferably W, X, Y and Z are independently or together —C(O)—, —C(S)—, —S— or —NH— to form a 2,4-thiazolidinedione, 2-thioxo-4-thiazolidinedione, 2-thioxo-4-imidazolidinedione or 2,4-imidazolidinedione.

Preferably when n=1, and — represents the bond is present, the compound is:

4-[2-(3,5,5,8,8-Tetramethyl-5,6,7,8-tetrahydro-2-naphthyl)-1,3-dioxolane]benzylidene-2,4-thiazolidinedione, 4-[2-(5,5,8,8-Tetramethyl-5,6,7,8-tetrahydro-2-naphthyl)-2-propyl]benzylidene-2,4-thiazolidinedione, 4-[2-(3,5,5,8,8-Tetramethyl-5,6,7,8-tetrahydro-2-naphthyl)-1,3-dioxolane]benzylidene-2-thioxo-4-thiazolidinedione, 4-[2-(5,5,8,8-Tetramethyl-5,6,7,8-tetrahydro-2-naphthyl)-2-propyl]benzylidene-2-thioxo-4-thiazolidinedione, 4-[2-(3,5,5,8,8-Tetramethyl-5,6,7,8-tetrahydro-2-naphthyl)-1,3-dioxolane]benzylidene-2-thioxo-4-imidazolidinedione, 4-[2-(5,5,8,8-Tetramethyl-5,6,7,8-tetrahydro-2-naphthyl)-2-propyl]benzylidene-2-thioxo-4-imidazolidinedione, 4-[2-(3,5,5,8,8-Tetramethyl-5,6,7,8-tetrahydro-2-naphthyl)-1,3-dioxolane]benzylidene-2,4-imidazolidinedione; or 4-[2-(5,5,8,8-Tetramethyl-5,6,7,8-tetrahydro-2-naphthyl)-2-propyl]benzylidene-2,4-imidazolidinedione.

In addition, when n=1, and — represents the bond is absent, the compound is:

4-[2-(3,5,5,8,8-Pentamethyl-5,6,7,8-tetrahydro-2-naphthyl)-1,3-dioxolane]benzyl-2,4-thiazolidinedione, 4-[2-(5,5,8,8-Tetramethyl-5,6,7,8-tetrahydro-2-naphthyl)-2-propyl]benzyl-2,4-thiazolidinedione, 4-[2-(3,5,5,8,8-Pentamethyl-5,6,7,8-tetrahydro-2-naphthyl)-1,3-dioxolane]benzyl-2-thioxo-4-thiazolidinedione, 4-[2-(5,5,8,8-Tetramethyl-5,6,7,8-tetrahydro-2-naphthyl)-2-propyl]benzyl-2-thioxo-4-thiazolidinedione, 4-[2-(3,5,5,8,8-Pentamethyl-5,6,7,8-tetrahydro-2-naphthyl)-1,3-dioxolane]benzyl-2-thioxo-4-imidazolidinedione, 4-[2-(5,5,8,8-Tetramethyl-5,6,7,8-tetrahydro-2-naphthyl)-2-propyl]benzyl-2-thioxo-4-imidazolidinedione, 4-[2-(3,5,5,8,8-Pentamethyl-5,6,7,8-tetrahydro-2-naphthyl)-1,3-dioxolane]benzyl-2,4-imidazolidinedione, or 4-[2-(5,5,8,8-Tetramethyl-5,6,7,8-tetrahydro-2-naphthyl)-2-propyl]benzyl-2,4-imidazolidinedione.

The structures for these compounds are shown below:

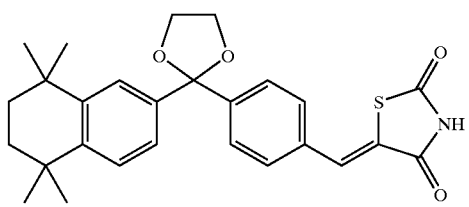

4-[2-(5,5,8,8-Tetramethyl-5,6,7,8-tetrahydro-2-
naphthyl)-1,3-dioxolane] benzylidene-2,4-
thiazolidinedione -continued

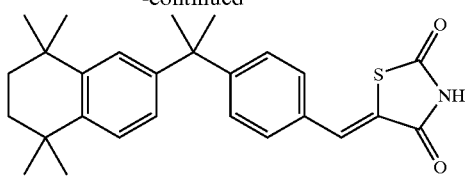

4-[2-(5,5,8,8-Tetramethyl-5,6,7,8-tetrahydro-2-naphthyl)-2-propyl]benzylidene-2,4-thiazolidinedione

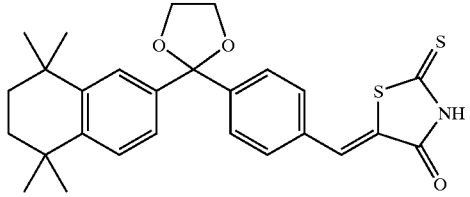

4-[2-(5,5,8,8-Tetramethyl-5,6,7,8-tetrahydro-2-naphthyl)-1,3-dioxolane]benzylidene-2-thioxo-4-thiazolidinedione

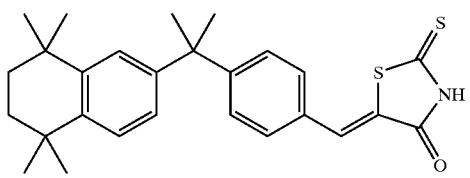

4-[2-(5,5,8,8-Tetramethyl-5,6,7,8-tetrahydro-2-naphthyl)-2-propyl]benzylidene-2-thioxo-4-thiazolidinedione

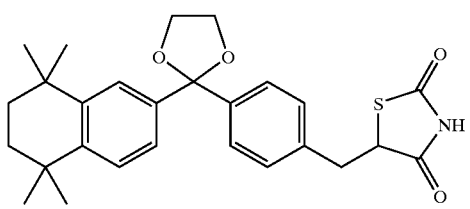

4-[2-(5,5,8,8-Tetramethyl-5,6,7,8-tetrahydro-2-naphthyl)-1,3-dioxolane]benzyl-2,4-thiazolidinedione

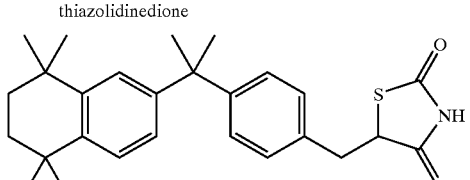

4-[2-(5,5,8,8-Tetramethyl-5,6,7,8-tetrahydro-2-naphthyl)-2-propyl]benzyl-2,4-thiazolidinedione

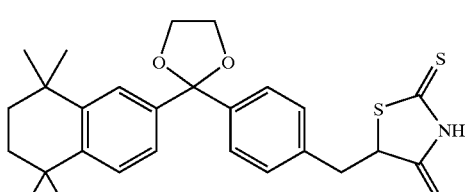

4-[2-(5,5,8,8-Tetramethyl-5,6,7,8-tetrahydro-2-naphthyl)-1,3-dioxolane]benzyl-2-thioxo-4-thiazolidinedione -continued

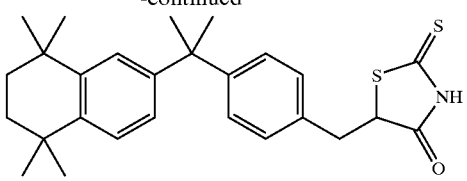

4-[2-(5,5,8,8-Tetramethyl-5,6,7,8-tetrahydro-2-naphthyl)-2-propyl]benzyl-2-thioxo-4-thiazolidinedione

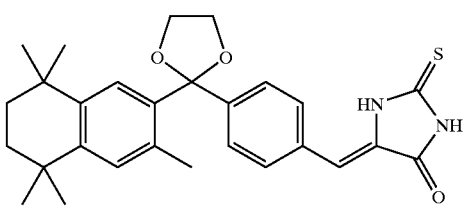

4-[2-(3,5,5,8,8-Tetramethyl-5,6,7,8-tetrahydro-2-naphthyl)-1,3-dioxolane]Benzylidene-2-thioxo-4-imidazolidinedione

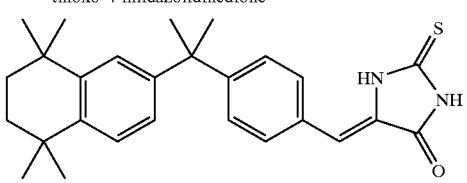

4-[2-(5,5,8,8-Tetramethyl-5,6,7,8-tetrahydro-2-naphthyl)-2-propyl]benzylidene-2-thioxo-4-imidazolidinedione

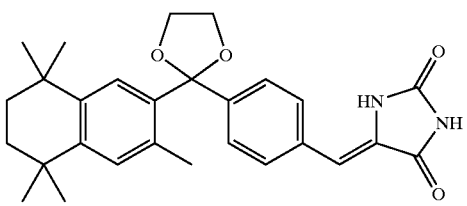

4-[2-(3,5,5,8,8-Tetramethyl-5,6,7,8-tetrahydro-2-naphthyl)-1,3-dioxolane]benzylidene-2,4-imidazo lidinedione

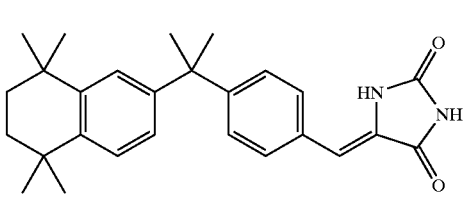

4-[2-(5,5,8,8-Tetramethyl-5,6,7,8-tetrahydro-2-naphthyl)-2-propyl]benzylidene-2,4-imidazolidinedione

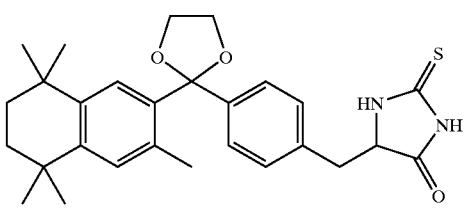

4-[2-(3,5,5,8,8-Pentamethyl-5,6,7,8-tetrahydro-2-naphthyl)-1,3-dioxolane]benzyl-2-thioxo-4-imidazolidinedione

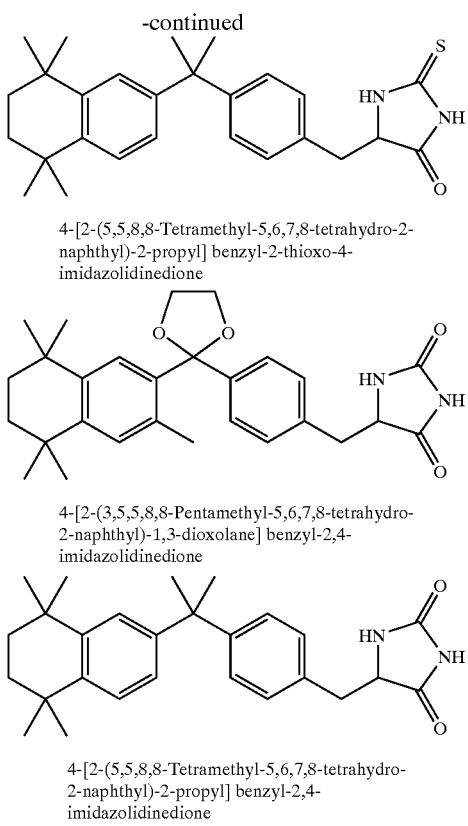

Figure 5:
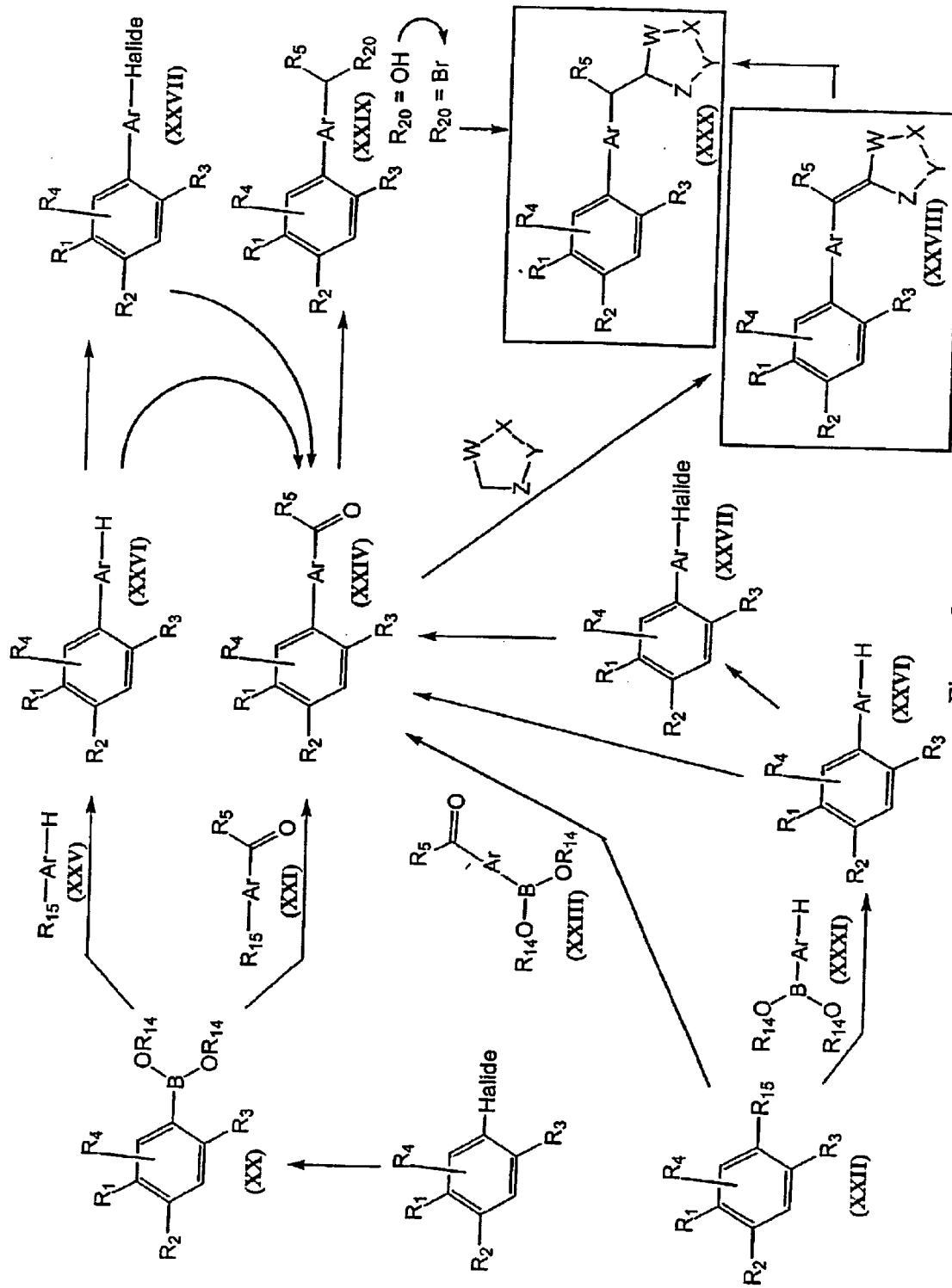
FIG. 5 shows examples of methods for synthesizing the compounds disclosed herein wherein n is 0 and m is 1.

4-[2-(5,5,8,8-Tetramethyl-5,6,7,8-tetrahydro-2-naphthyl)-2-propyl] benzyl-2-thioxo-4-imidazolidinedione 4-[2-(3,5,5,8,8-Pentamethyl-5,6,7,8-tetrahydro-2-naphthyl)-1,3-dioxolane] benzyl-2,4-imidazolidinedione 4-[2-(5,5,8,8-Tetramethyl-5,6,7,8-tetrahydro-2-naphthyl)-2-propyl] benzyl-2,4-imidazolidinedione Making the Compositions Various synthetic methods may be employed in the production of the compounds disclosed herein. A representative set of synthetic pathways are shown in FIG. 5 for n=0. One method, for example, includes coupling a boronic acid of Formula (XX), $R_{14}$=H, with a carbonyl-containing aryl bromide of Formula (XXI), $R_{15}$=Br, to give biaryl (XXIV) that is substituted with a carbonyl group, preferably a formyl group (i.e., $R_5$=H). Alternatively, boronic acid (XX) may be coupled with aryl bromide (XXV), $R_{15}$=Br, to give biaryl (XXVI) that is subsequently formulated using techniques known in the art, such as the Vilsmeier or the Vilsmeier-Haack reaction, the Gatterman reaction, the Duff reaction, the Reimer-Tiemann reaction or a like, reaction. Coupling reactions such as that described for the formation of Biaryl (XXIV) and (XXVI) may also be conducted using boronic esters, such as where $R_{14}$ together with the boron from a pinacol borate ester (formation of pinacol esters: Ishiyama, T., et al., *J. Org. Chem.* 1995, 60, 7508–7510, Ishiyama, T., et al., *Tetrahedron Letters* 1997, 38, 3447–3450; coupling pinacol esters: Firooznia, F. et al., *Tetrahedron Letters* 1999, 40, 213–216, Manickam, G. et al., *Synthesis* 2000, 442–446; all four citations incorporated herein by reference). In addition, $R_{15}$ may also be I, Cl or triflate (derived from a phenol).

Biaryl (XXVI) may also be acylated, for example by the Friedel-Crafts Acylation reaction or the like. Preferably, biaryl (XXVI) is formylated. Alternatively, in a two step manner, biaryl (XXVI) is formylated by first performing a halogenation step to give biaryl (XXVII), such as a bromination, followed by a halogen-metal exchange reaction using an alkyl lithium and reaction with DMF or equivalent known in the art to give biaryl (XXIV) where $R_5$ is H. The carbonyl group of biaryl (XXIV) may subsequently be condensed with a heterocycle possessing an active methylene moiety, such as 2,4-thiazolidinedione, 2-thioxo-4-thiazolidinedione, isoxazolidinedione, 2,4-imidazolidinedione or 2-thioxo-4-imidazolidinedione to give benzylidene (XXVIII). The carbonyl group of biaryl (XXIV) may also be reduced, such as with sodium borohydride, to benzyl alcohol (XXIX, $R_{20}$=OH) and converted to benzyl bromide (XXIX, $R_{20}$=Br) with HBr or some other method known in the art, such as $PPh_3/CBr_4$. Benzyl bromide (XXIX, $R_{20}$=Br) is allowed to react with the anion(s) of 2,4-thiazolidinedione to give biaryl [(XXX), where: W=—C(O)—, X=—NH—, Y=—C(O)— and Z=—S—]. Similarly, anions of other heterocycles disclosed herein may be used. Alternative, biaryl [(XXX), where: W=—C(O)—, X=—NH—, Y=—C(O)— and Z=—S—] may be prepared by a reduction of benzylidene [(XXVIII), where: W=—C(O)—, X=—NH—, Y=—C(O)— and Z=—S—] using methods known in the art, such as hydrogenation in the presence of Pd/C, Mg/MeOH and the like.

In an alternative manner, the coupling may take place between aryl (XXII), such as where $R_{15}$=Br, and boronic acid (XXIII, $R_{14}$=H) to give the above mention biaryl (XXIV). Also aryl (XXII) may be coupled with boronic acid (XXXI) to give biaryl (XXVI). Employing the same strategy as described above biaryl (XXVI) may be either formylated or acylated to achieve biaryl (XXIV).

In some embodiments of the invention provide a process for the preparation of a compound of the Formula (XV):

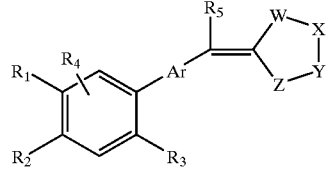

(XV)

wherein:

$R_1$ and $R_2$ are independently or together hydrogen, alkyl, substituted alkyl, alkenyl, substituted alkenyl, alkynyl, substituted alkynyl, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide or haloalkoxy; or $R_1$ and $R_2$ together with the aromatic ring form a cycloalkyl, substituted cycloalkyl, cycloalkenyl or substituted cycloalkenyl optionally comprising 1 or 2 heteroatoms selected from O, S, NH and N-alkyl;

$R_3$ and $R_4$ are independently or together hydrogen, alkyl, substituted alkyl, alkenyl, substituted alkenyl, alkynyl, substituted alkynyl, halogen, cyano, nitro, hydroxyl, acyloxy, amino, mono-substituted amino, di-substituted amino, alkylsulfonamide, arylsulfonamide, alkylurea, arylurea, alkylcarbamate, arylcarbamate, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

Ar is Formula (II), (III), (IV) or (V):

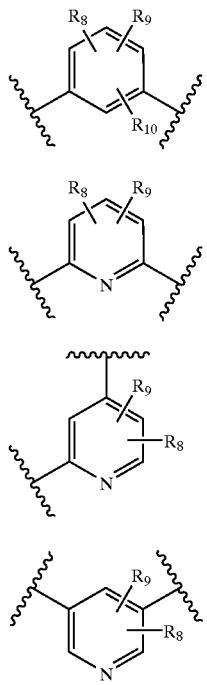

(II)

(III)

(IV)

(V)

where

R$_8$, R$_9$ and R$_{10}$ are independently or together hydrogen, alkyl, substituted alkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide;

R$_{11}$ is hydrogen, alkyl or substituted alkyl;

R$_5$ is hydrogen, halogen, hydroxy, alkyl or substituted alkyl;

— represents a bond present or absent; and

W, X, Y and Z are independently or together —C(O)—, —C(S)—, —S—, —O— or —NH— residues that form a 2,4-thiazolidinedione, 2-thioxo-4-thiazolidinedione, isoxazolidinedione, 2,4-imidazolidinedione or 2-thioxo-4-imidazolidinedione residue;

comprising the steps of:

1) coupling a first aryl residue with a second aryl residue to give a biaryl carbonyl containing compound; wherein the first aryl residue comprises a substituted or unsubstituted residue having the structure:

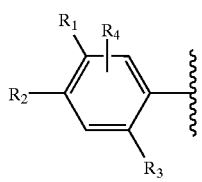

and wherein the second aryl residue has a carbonyl group and comprises a substituted or unsubstituted residue having the structure:

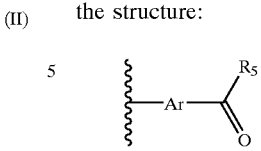

and wherein the biaryl carbonyl containing compound comprises a substituted or unsubstituted residue having the structure:

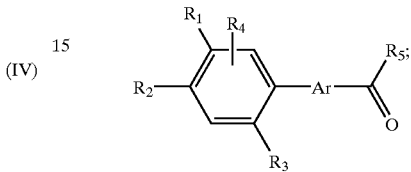

and 2) condensing the biaryl carbonyl containing compound with an active methylene compound of the structure:

In another embodiments of the invention provides a process further comprising the step of reducing the benzylidene of Formula (XV) to form the benzyl compound of Formula (XVI):

(XVI)

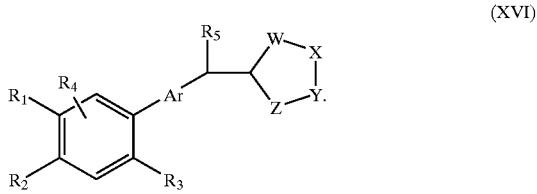

A number of methods suitable for reducing benzylidene compounds to benzyl compounds (including hydrogenation, reaction with metal hydride reagents, or dissolving metal reductions) are known to those of skill in the art, and those methods may be applied in the methods of the instant invention.

The various organic group transformations utilized herein may be performed by a number of procedures other than those described above. References for other synthetic procedures that may be utilized for the synthetic steps leading to the compounds disclosed herein may be found in, for example, March, J., *Advanced Organic Chemistry*, 4$^{th}$ Edition, Weiley-Interscience (1992); or Larock, R. C., *Comprehensive Organic Transformations, A Guide to Functional Group Preparations*, VCH Publishers, Inc. (1989), both incorporated herein by reference.

One embodiment of the invention relates to the processes for making compounds of Formula I, where n is 0, which comprises coupling two aromatic rings to give a biaryl wherein one of the aryl rings contains a carbonyl moiety, preferably an aldehyde. The resulting biaryl product may be subsequently condensed with an active methylene compound, such as 2,4-thiazolidinedione, 2-thioxo-4-thiazolidinedione, 2,4-imidazolidinedione or 2-thioxo-4-imidazolidinedione to give a benzylidene compound of Formula (I) where — is a bond. In an optional step, the benzylidene compound may be reduced to give a benzyl compound of Formula (I) where — is absent.

Coupling of two aryl rings may be conducted using an aryl boronic acid or esters with an aryl halide (such as, iodo, bromo, or chloro), triflate or diazonium tetrafluoroborate; as described respectively in Suzuki, *Pure & Applied Chem.*, 66:213–222 (1994), Miyaura and Suzuki, *Chem. Rev.* 95:2457–2483 (1995), Watanabe, Miyaura and Suzuki, *Synlett.* 207–210 (1992), Littke and Fu, *Angew. Chem. Int. Ed.*, 37:3387–3388 (1998), Indolese, *Tetrahedron Letters*, 38:3513–3516 (1997), Firooznia, et. al., *Tetrahedron Letters* 40:213–216 (1999), and Darses, et al., *Bull. Soc. Chim. Fr.* 133:1095–1102 (1996); all incorporated herein by reference. According to this coupling reaction, precursors such as (XX) and (XXI) may be employed:

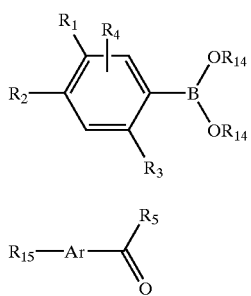

where $R_{14}$ is either alkyl or hydrogen and $R_{15}$ is a halide (such as, iodo, bromo, or chloro), triflate or diazonium tetrafluoroborate. Alternately, it is understood that the coupling groups may be reversed, such as the use of (XXII) and (XXIII), to achieve the same coupling product:

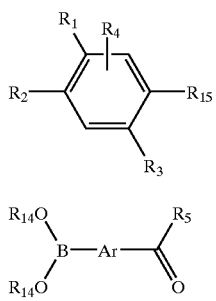

where $R_{14}$ and $R_{15}$ have the same meaning as described above. The preparation of the above mentioned precursors may be prepared by methods readily available to those skilled in the art. For example, the boronic ester may be prepared from an aryl halide by conversion into the corresponding aryl lithium, followed by treatment with a trialkyl borate. Preferably, the boronic ester is hydrolyzed to the boronic acid.

The coupling reaction may also be conducted between an arylzinc halide and an aryl halide or triflate. Alternately, the coupling reaction may also be executed using an aryl trialkyltin derivative and an aryl halide or triflate. These coupling methods are reviewed by Stanforth, *Tetrahedron* 54:263–303 (1998) and incorporated herein by reference. In general, the utilization of a specific coupling procedure is selected with respect to available precursors, chemoselectivity, regioselectivity and steric considerations.

Condensation of the biaryl carbonyl containing derivatives (e.g., FIG. 5, compound (XXIV)) with a suitable active methylene compound, such as, 2,4-thiazolidinedione, may be accomplished by the use of methods known in the art. For example, the biaryl carbonyl product from the coupling reaction may be condensed with an active methylene compound to give a benzylidene compound of Formula (I) (i.e., — is a bond) as described by Tietze and Beifuss, *Comprehensive Organic Synthesis* (Pergamon Press), 2:341–394, (1991), incorporated herein by reference. It is understood by those of skill in the art that intermediates having hydroxyl groups bound thereto may be formed during condensation of a biaryl carbonyl containing derivative and an active methylene compound, as shown below.

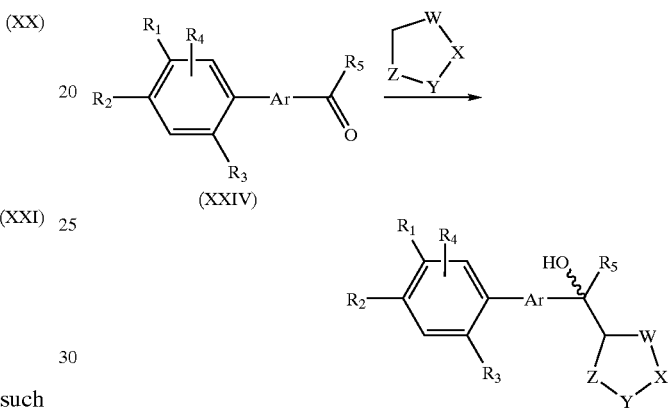

The hydroxyl groups of such intermediates are often eliminated (as water) during the condensation reaction, to form the desired benzylidene compound. Nevertheless, the conditions of the reaction may be modified for the isolation or further use of hydroxyl containing intermediates, and such embodiments are within the scope of the invention. Although the reaction shown above depicts the formation of the condensation intermediate for the reaction between compound (XXIV) and an active methylene compound, it is understood that a similar intermediate is within the scope of the invention for compounds (XLV) and (XLII). Effective catalysts for the condensation may be selected from ammonia, primary, secondary and tertiary amines, either as the free base or the amine salt with an organic acid, such as acetic acid. Examples of catalysts include pyrrolidine, piperidine, pyridine, diethylamine and the acetate salts thereof. Inorganic catalysts may also be used for the condensation. Inorganic, catalysts include, but are not limited to, titanium tetrachloride and a tertiary base, such as pyridine; and magnesium oxide or zinc oxide in an inert solvent system. This type of condensation can be strongly solvent-dependent and it is understood that routine experimentation may be necessary to identify the optimal solvent with a particular catalyst, preferable solvents include ethanol, tetrahydrofuran, dioxane or toluene; or mixtures thereof.

The active methylene compound of the present invention may be 2,4-thiazolidinedione, 2-thioxo-4-thiazolidinone, 2,4-imidazolidinedione or 2-thioxo-4-imidazolidinedione. The resulting benzylidene (e.g., FIG. 5, compound (XXXIII)) may be reduced, if desired, to a compound of Formula (I) wherein — is absent (e.g., FIG. 5, compound (XXX)).

Figure 6:
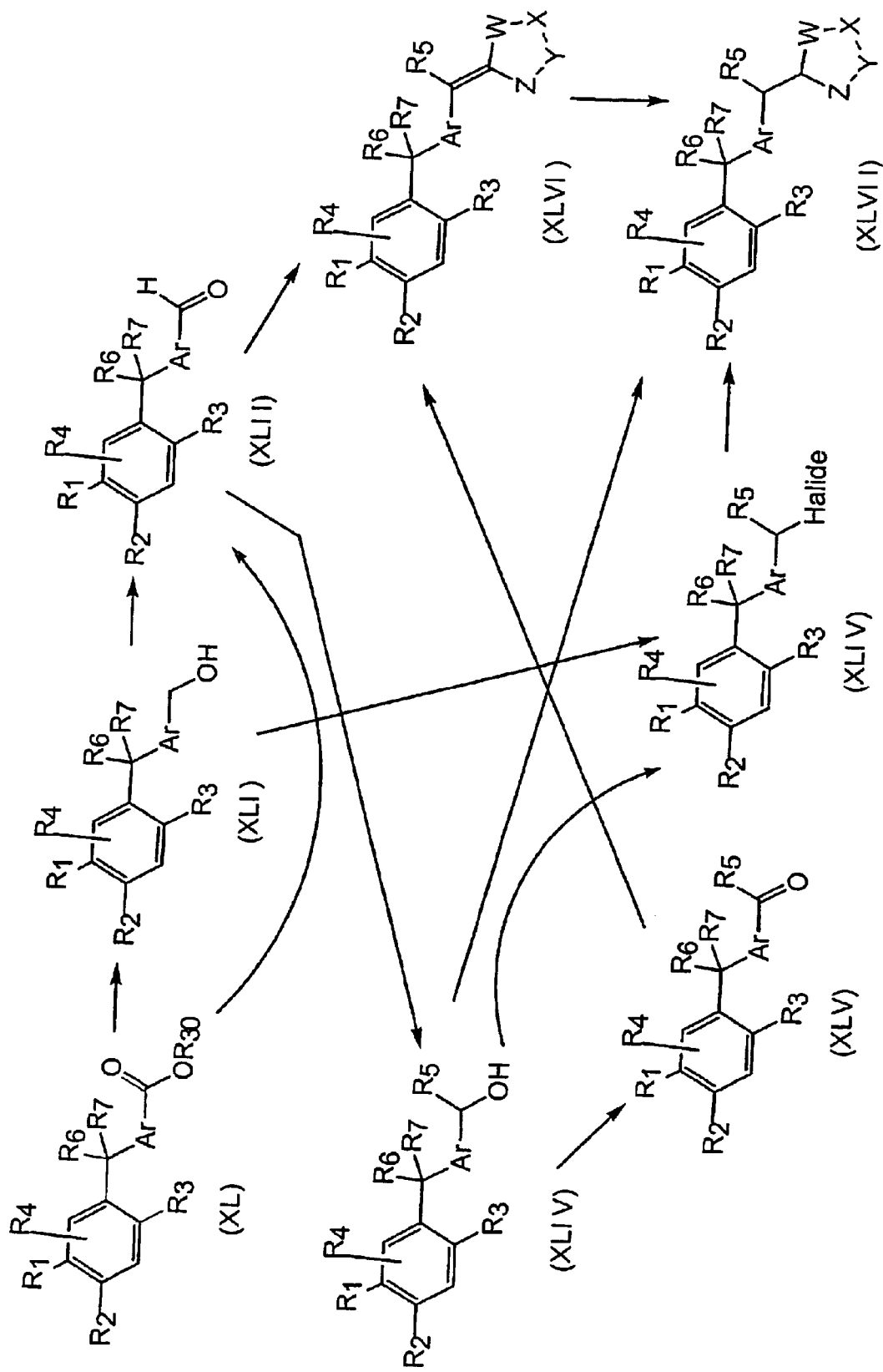
FIG. 6 shows examples of methods for synthesizing the compounds disclosed herein wherein n and m are 1.

In addition, various methods may be employed in the production of the compounds disclosed herein wherein n=1, representative examples are shown in FIG. 6. Structures of compound (XL) may be prepared by methods known in the art. The acid, $R_{30}$=H or the ester, $R_{30}$=aryl, alkyl or substituted alkyl, may be reduced to the corresponding benzyl alcohol (XLI) followed by oxidation to an aldehyde (XLII). Alternatively, ester (XL), $R_{30}$=alkyl or substituted alkyl, may be reduced directly to the aldehyde via selective reductions, for example, DIBAL. Aldehyde (XLII) may be, reacted with a metal reagent, such as a Grignard reagent, to give benzyl alcohol (XLIV) that can subsequently be converted to ketone (XLV) via an oxidation, such as a Swern oxidation, Corey oxidation with NCS or another suitable procedure described by Hudlicky, M, *Oxidations in Organic Chemistry*, ACS Monograph 186 (1990), incorporated herein by reference. In a similar manner as described above, compound (XLII) or compound (XLV) may be condensed with an active methylene of a heterocycle to give compound (XLVI). The reduced analogue (XLVII) may be prepared in a manner similar to the process described above using a benzyl halide derived from either benzyl alcohol (XLI) or reduction from compound (XLVI).

Figure 7:
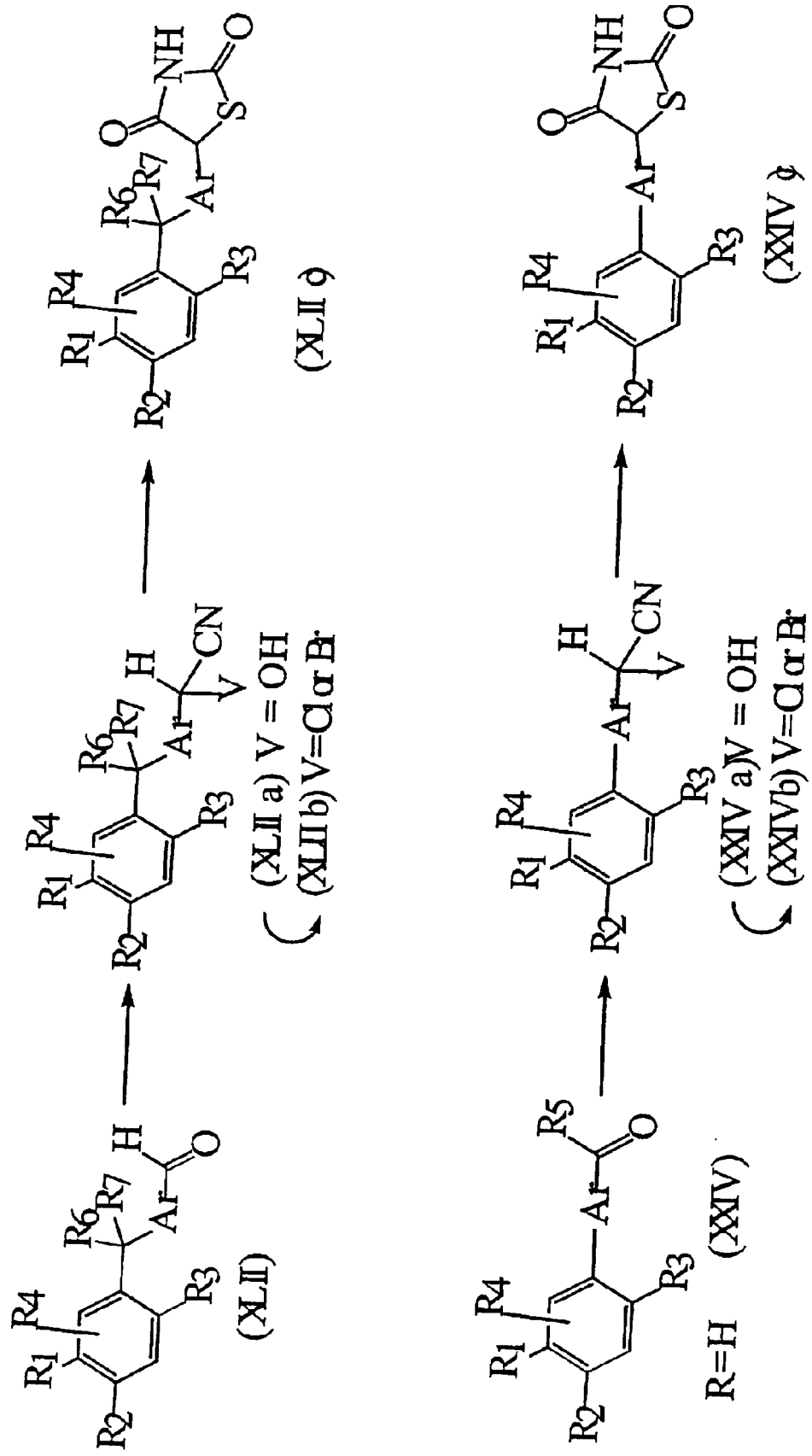
FIG. 7 shows examples of methods for synthesizing the compounds disclosed herein wherein n is 0 or 1 and m is 0.

In addition, various methods may be employed in the production of the compounds disclosed herein wherein n is either 0 or 1 and m is 0, representative examples are shown in FIG. 7. Utilizing, for example, compound (XLII) or (XXIV) the carbonyl may be converted to a cyanohydrin using methods known in the art. Such methods include, the use of acetone cyanohydrin, TMS—CN/$ZnI_2$ (followed by hydrolysis of the TMS ether) and the like. The resulting alcohol of the cyanohydrin may be converted to a halide (where V=Cl or Br) with the use of thionyl chloride, thionyl bromide or the like, in the presence or absence of solvent. Conversion to compounds of Formula where m is equal to 0 may be prepared by the reaction of the (XLII b) or (XXIV b) with thiourea followed by hydrolysis.

Using the Compositions

The compounds of the present invention have been found to be potent compounds in a number of biological assays, both in vitro and in vivo, that correlate to, or are representative of, human diseases.

Figure 1B:
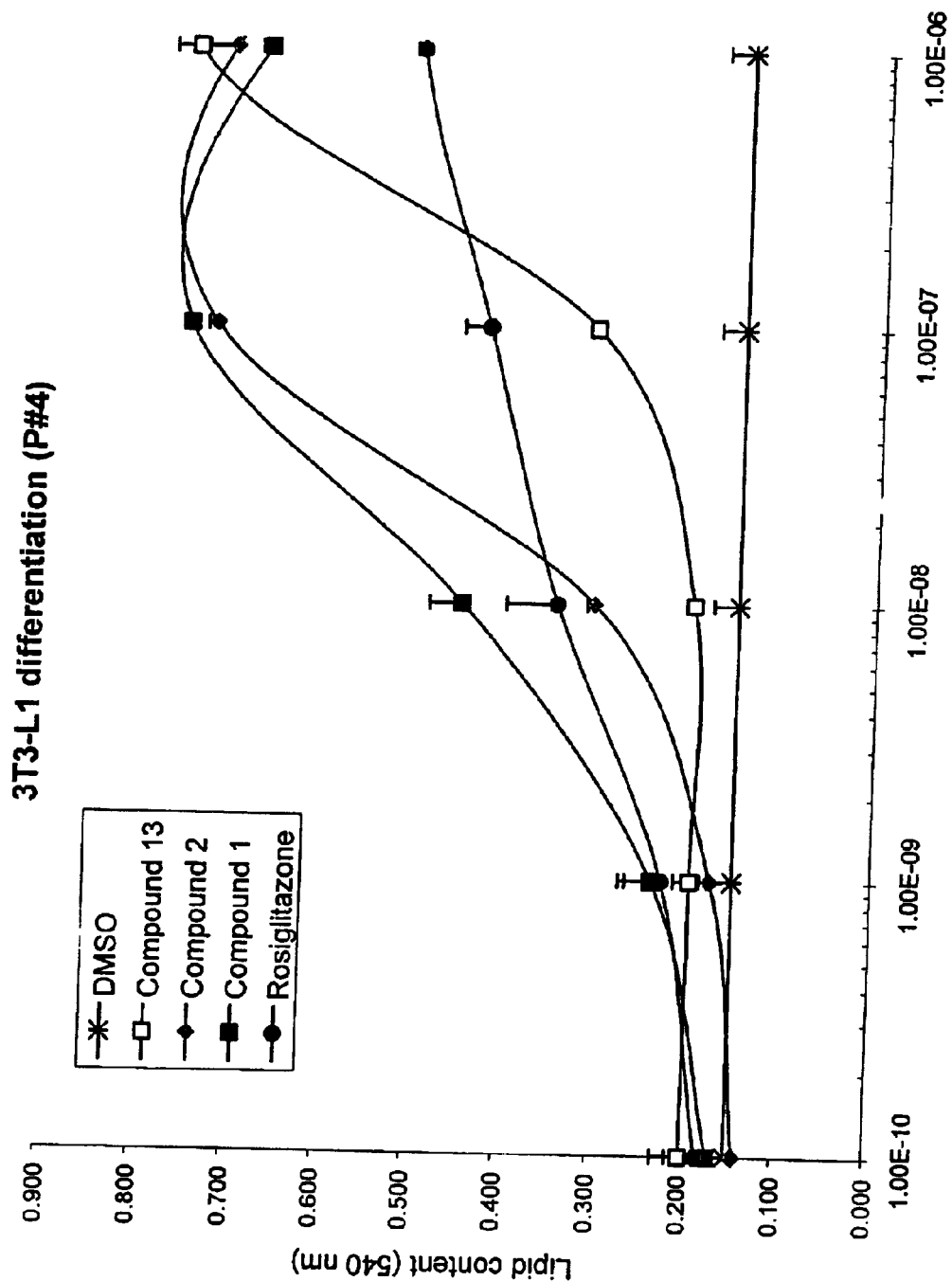
FIG. 1b shows the differentiation inducing activity of the compounds of the present invention in the presence of insulin.

For instance, the compounds induce the differentiation of preadipocytes into adipocytes. This activity (Harris and Kletzien, *Mol. Pharmacol.*, 45:439–445 (1994); Willson et al., *J. Med. Chem.* 39:665–668 (1996)) has been observed for certain compounds that have antidiabetic activity in humans (Teboul et al., *J. Biol. Chem.* 270:28183–28187 (1995)). Examples for the adipocyte differentiation activity of the compounds of the present invention are shown in FIGS. 1a and 1b (rosiglitazone, Avandia™, an insulin sensitizer approved for the treatment of type 2 diabetes, is shown for comparison). FIG. 1a shows the differentiation activity of the present invention without the presence of insulin, whereas FIG. 1b shows the differentiation activity in the presence of insulin. Both in the absence and presence of insulin, the disclosed compounds increase lipid levels. The ability of the compounds to induce cells of the adipocyte lineage to differentiate may also correlate to the ability of the compounds to treat or prevent other diseases including such proliferative diseases as breast, prostate and other cancers.

Figure 2A:
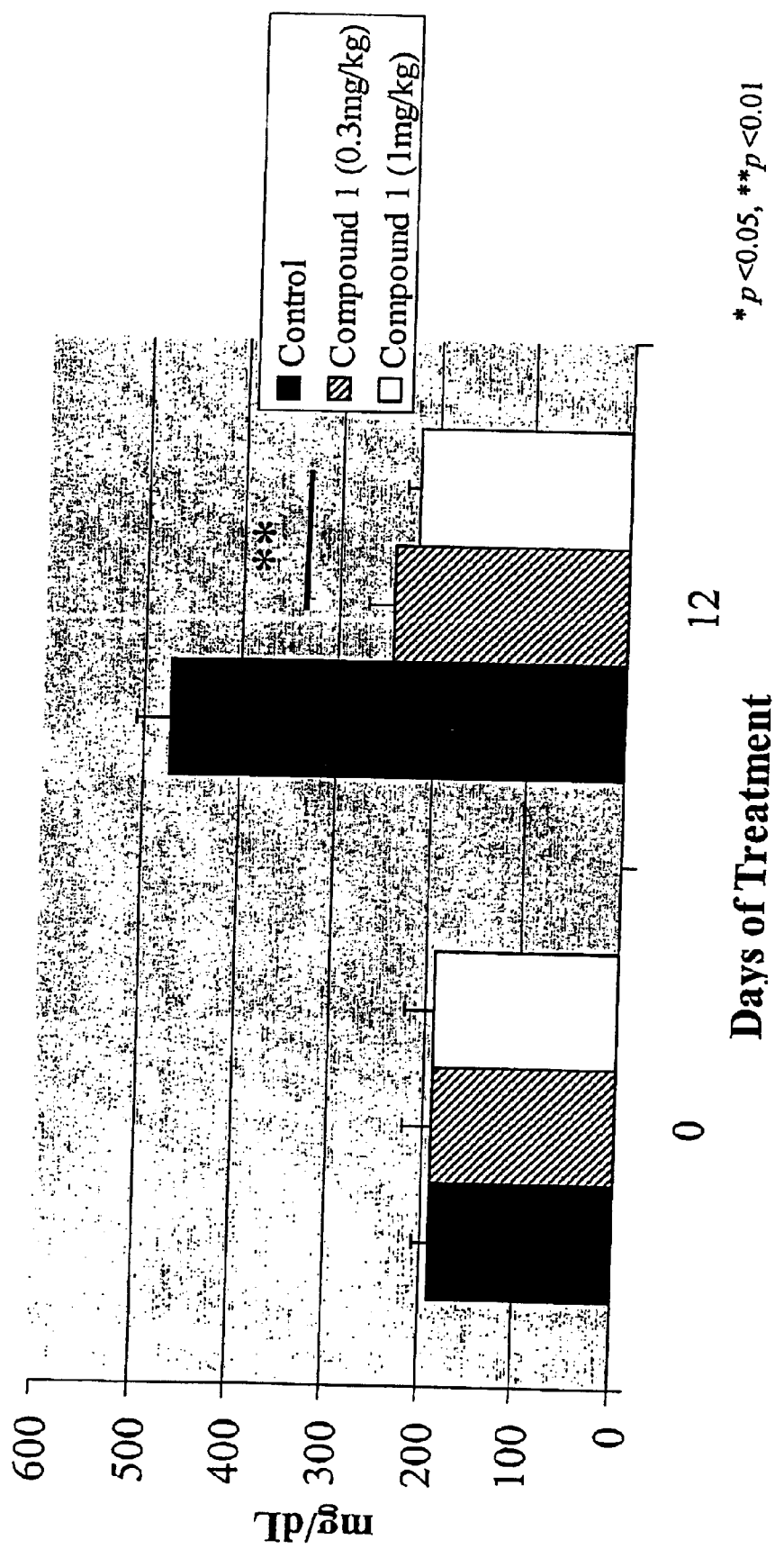
FIG. 2a shows the glucose lowering activity of Compound 1 in the db/db Mouse Model.
Figure 2B:
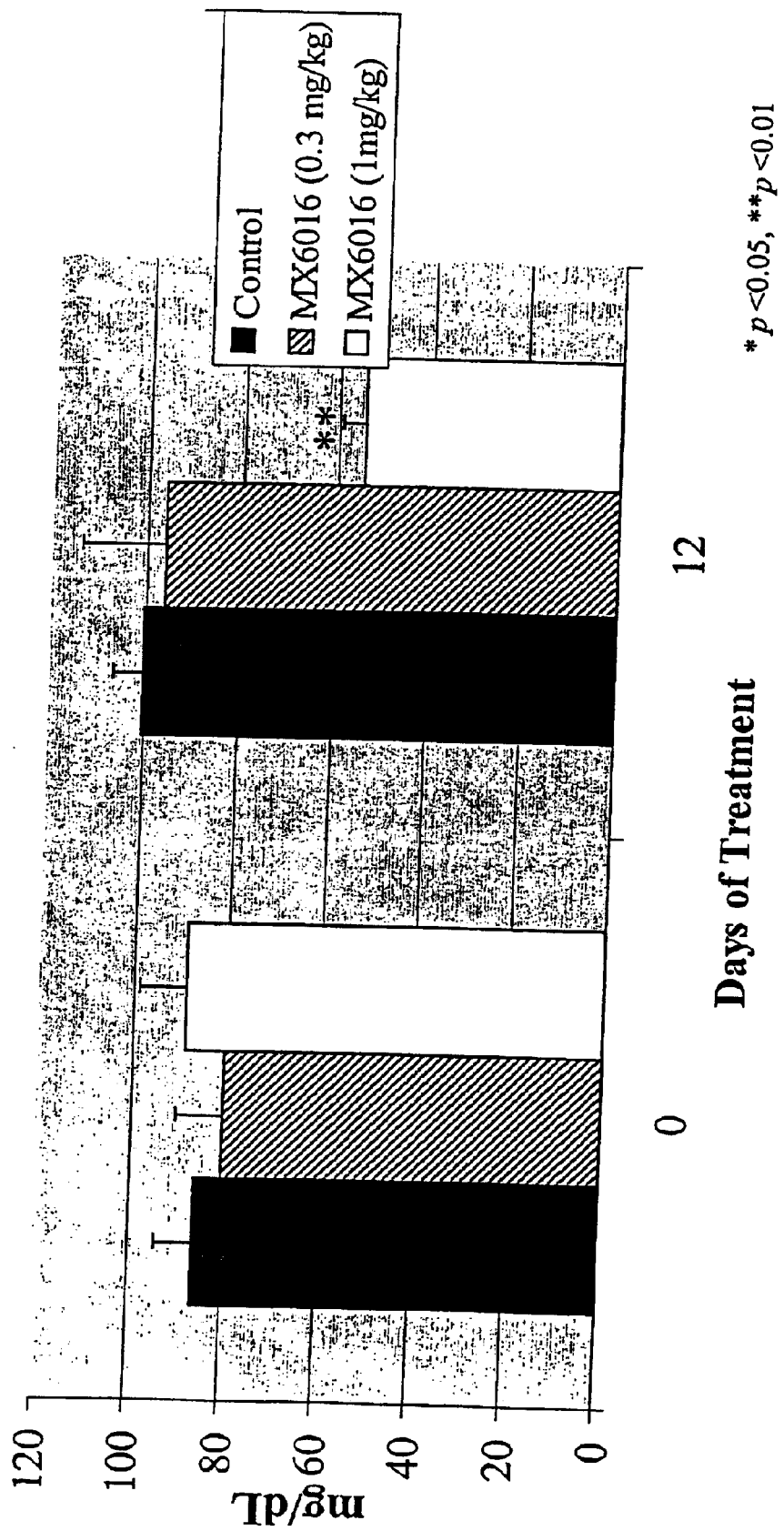
FIG. 2b shows the triglyceride lowering activity of Compound 1 in the db/db Mouse Model.
Figure 3A:
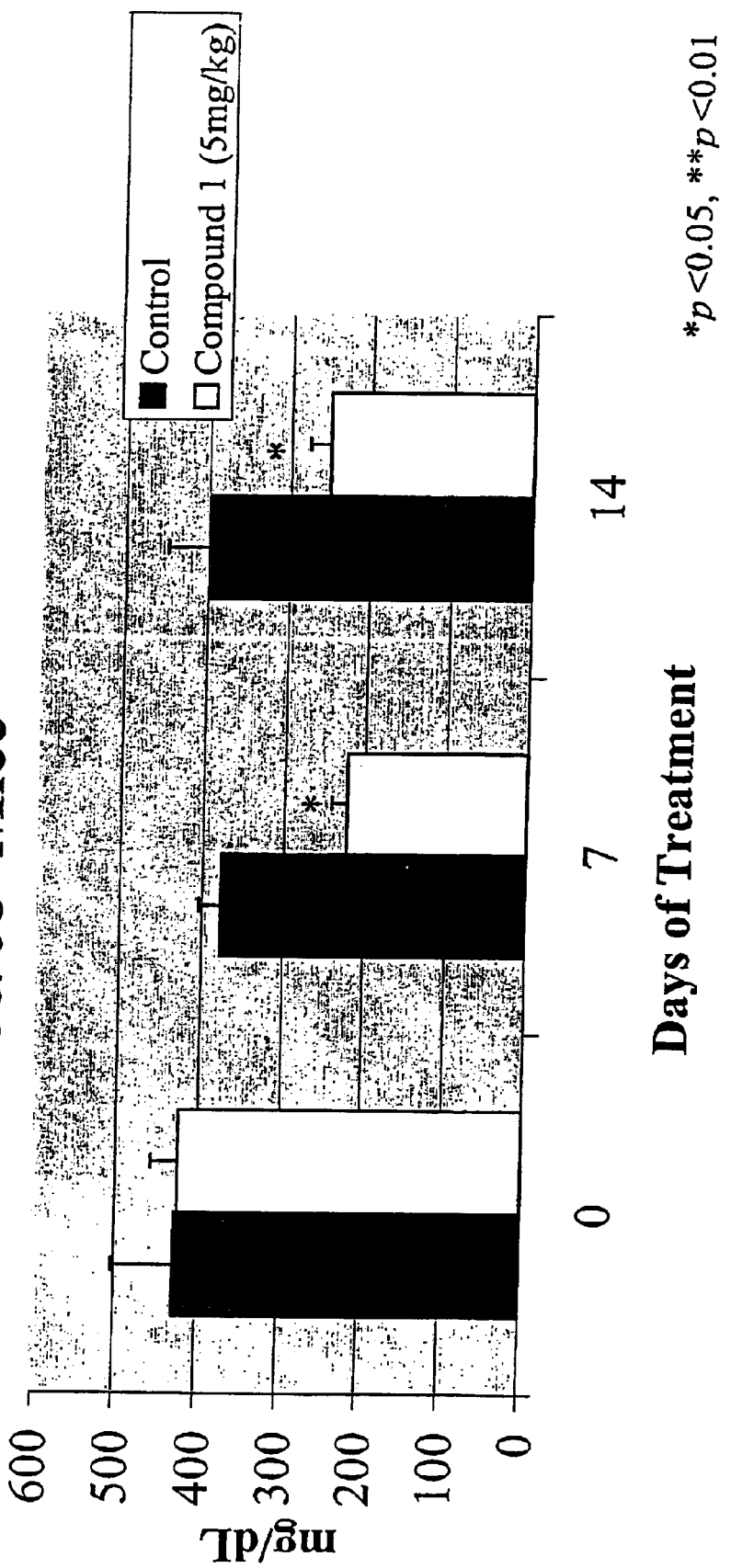
FIG. 3a shows the glucose lowering activity of Compound 1 in the ob/ob, Mouse Model.
Figure 4A:
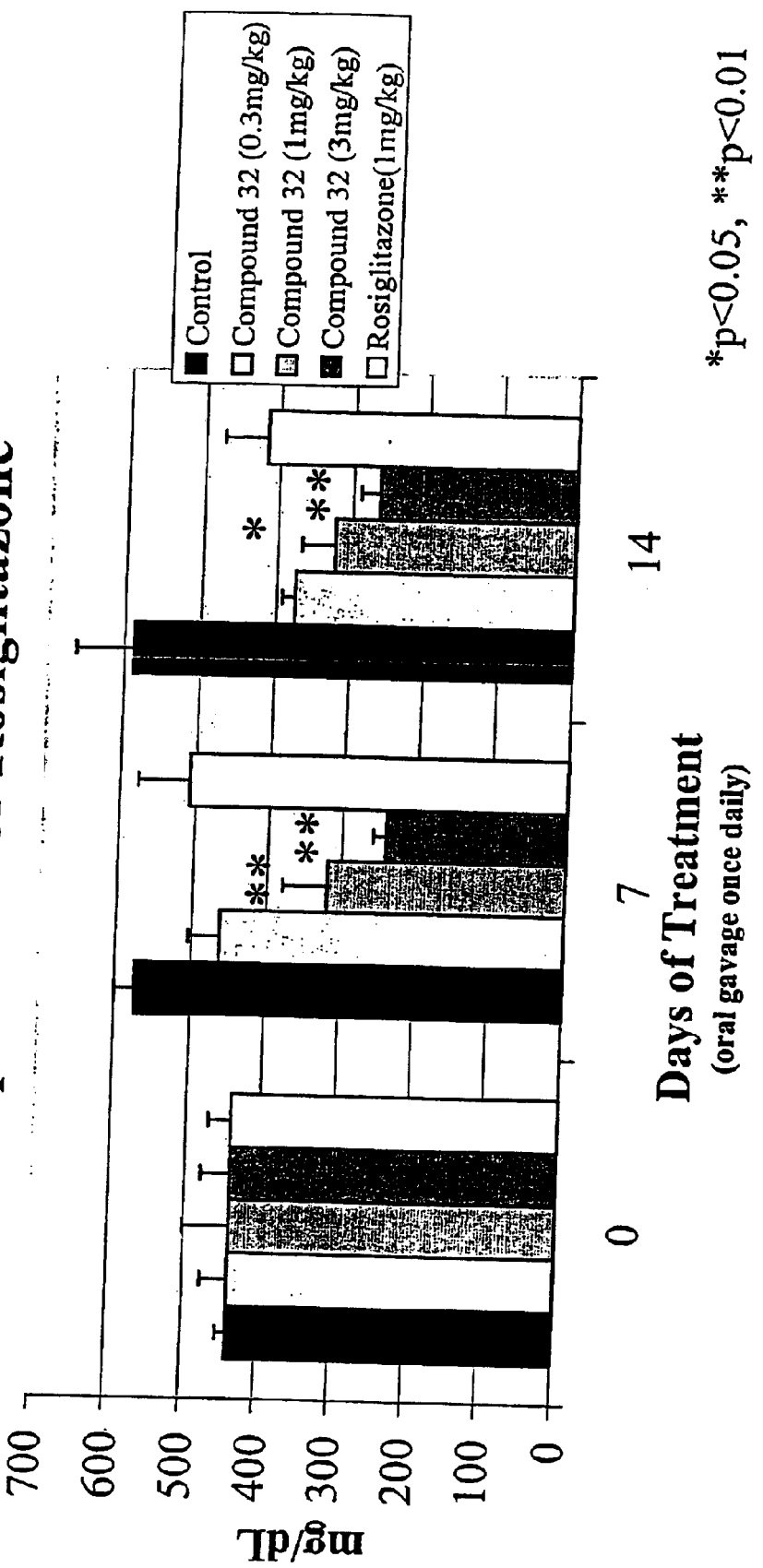
FIG. 4a shows the glucose lowering activity of Compound 32 in the db/db Mouse Model.
Figure 4B:
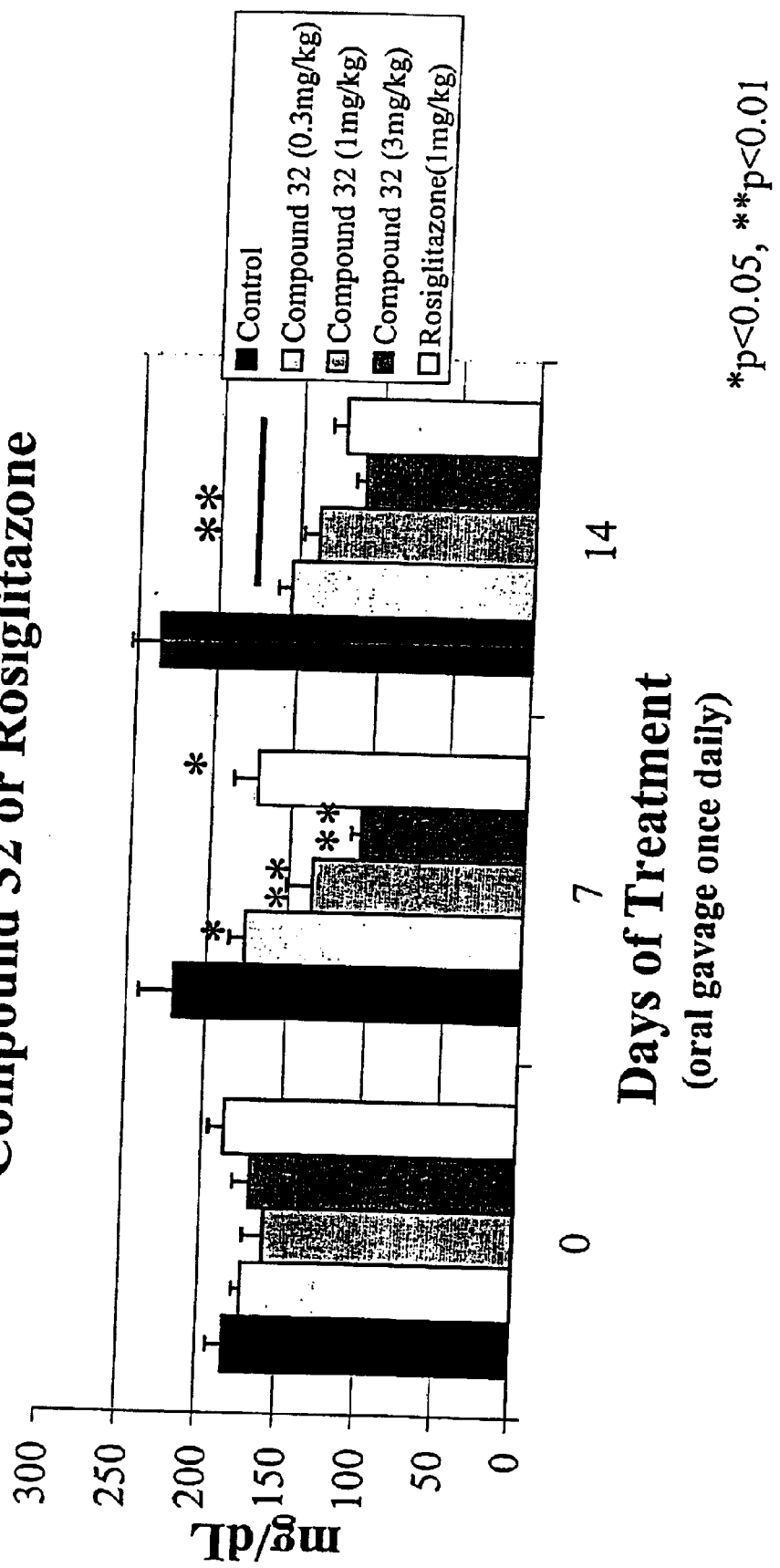
FIG. 4b shows the triglyceride lowering activity of Compound 32 in the db/db Mouse Model.

The ability of the compounds to function as antidiabetic molecules may be demonstrated in animal models for type 2 diabetes. In young db/db mice, compound 1 is shown to prevent increases in glucose and triglyceride levels when administered orally (FIGS. 2a, b). In another animal model of type 2 diabetes, the ob/ob mouse, compound 1 is shown to reduce glucose and triglyceride levels (FIGS. 3a, b). In yet another animal model of type 2 diabetes, diabetic db/db mice, compound 32 is shown to be equally or more potent than rosiglitazone in reducing glucose and triglyceride levels (FIGS. 4a and 4b).

Compounds disclosed herein are useful, for example, to modulate metabolism (such as, for example, lipid metabolism and carbohydrate metabolism) or adipocyte differentiation, and especially to treat type 2 diabetes. Modulation of lipid metabolism, for example, would include an increase of lipid content intracellularly or extracellularly. Modulation of lipid metabolism could also include a decrease of lipid content intracellularly or extracellularly. Modulation of metabolism may occur directly for example, through binding of the compound of Formula I with its cognate nuclear receptor, which directly affects an increase) or decrease in lipid content by up-regulation or down-regulation of a gene involved in lipid metabolism. Modulation of metabolism may also occur indirectly, for example, through binding of the compound of Formula I with its cognate receptor, which up-regulates or down-regulates cellular differentiation or growth of cells that produce lipids, thereby indirectly causing lipid metabolism to be modulated. Modulation, for example, could be an increase in lipid metabolism, such that lipid metabolism is greater than that of a control. Modulation, also includes, for example, an increase in lipid metabolism, such that the lipid metabolism approaches that of a control. Likewise, modulation of lipid metabolism could be a decrease in lipid metabolism, such that the lipid metabolism is less than or decreasing towards a control. Carbohydrate metabolism may also be up-regulated or down-regulated to either approach the level of carbohydrate metabolism in a control or to deviate from the level of carbohydrate metabolism in a control. Changes in carbohydrate metabolism may directly or indirectly also result in changes of lipid metabolism and, similarly, changes in lipid metabolism may lead to changes in carbohydrate metabolism. An example is type 2 diabetes where an increase in free fatty acids in the patients leads to decreased cellular uptake and metabolism of glucose.

Performing an adipocyte differentiation assay, as described in Examples 33 and 34, is one way to assay whether a compound indirectly increases lipid content. In one disclosed embodiment, the compounds of Formula I, when the concentration of the compounds of Formula I is less than or equal to $10^{-6}$ M, will lead to the differentiation of preadipocytes into adipocytes, of which the latter will have an increase in lipid content.

It is understood that a variety of lipid molecules may be modulated. The compounds disclosed herein may modulate a single type of lipid molecule, such as a triglyceride, or the compounds disclosed herein may modulate multiple types of lipid molecules. The compounds disclosed herein may also modulate a single or variety of carbohydrate molecules. The compounds disclosed herein may modulate metabolism disorders, such as type 2 diabetes. Metabolism can be modulated by the compounds disclosed herein by, for example, decreasing the serum glucose levels and/or decreasing the serum triglyceride levels, relative to a control having serum glucose and/or triglyceride levels indicative of a mammal having type 2 diabetes. It is recognized that any decrease in serum glucose and/or triglyceride levels can benefit the mammal having type 2 diabetes.

These compounds may be characterized by their low molecular weights and physiological stability, and therefore, represent a class that may be implemented to prevent, alleviate, and/or otherwise, treat disorders of lipid and carbohydrate metabolism, such as obesity, dislipidemea, type 2 diabetes and other diseases related to type 2 diabetes.

It is understood that treatment or prevention of type 2 diabetes may involve modulation of lipid or carbohydrate metabolism, such as the modulation of serum glucose or serum triglyceride levels.

A preferred embodiment of the invention relates to the use of the compounds disclosed herein. The compounds disclosed herein may be either used singularly or plurally, and pharmaceutical compositions thereof for the treatment of mammalian diseases, particularly those related to humans. Compounds disclosed herein and compositions thereof may be administered by various methods including, for example, orally, enterally, parentally, topically, nasally, vaginally, ophthalinically, sublingually or by inhalation for the treatment of diseases related to lipid metabolism, carbohydrate metabolism, lipid and carbohydrate metabolism such as polycystic ovary syndrome, syndrome X, type 2 diabetes, including disorders related to type 2 diabetes such as, diabetic retinopathy, neuropathy, macrovascular disease or differentiation of adipocytes. Routes of administration and dosages known in the art may be found in *Comprehensive Medicinal Chemistry*, Volume 5, Hansch, C. Pergamon Press, 1990; incorporated herein by reference. The compositions may also be used as regulators in diseases of uncontrolled proliferation. The composition may be useful in the treatment of polycystic kidney disease and cancers such as, carcinomas, lymphomas, leukemias, and sarcomas. A representative but non-limiting list of cancers is lymphoma, Hodgkin's Disease, myeloid leukemia, bladder cancer, brain cancer, head and neck cancer, kidney cancer, lung cancers such as small cell lung cancer and non-small cell lung cancer, myeloma, neuroblastoma/glioblastoma, ovarian cancer, pancreatic cancer, prostate cancer, skin cancer, liver cancer, melanoma, colon cancer, cervical carcinoma, breast cancer, and epithelial cancer. Compounds disclosed herein may be used for the treatment of inflammatory diseases such as osteoarthritis, rheumatoid arthritis, Crohn's Disease, pulmonary fibrosis, and Inflammatory Bowel Disease.

Although the compounds described herein may be administered as pure chemicals, it is preferable to present the active ingredient as a pharmaceutical composition. Thus another embodiment of is the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the composition and not overly deleterious to the recipient thereof.

Pharmaceutical compositions include those suitable for oral, enteral, parental (including intramuscular, subcutaneous and intravenous), topical, nasal, vaginal, ophthalinical, sublingually or by inhalation administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or one or more preservative.

The compounds may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603, incorporated herein by reference) or Bawas et al. (U.S. Pat. Nos. 4,931,279, 4,668,504 and 4,713,224; all incorporated herein by reference). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient may also be delivered via iontophoresis, e.g., as disclosed in U.S. Pat. Nos. 4,140,122, 4383,529, or 4,051,842; incorporated herein by reference.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions may be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, one of skill in the art understands how to extrapolate in vivo data obtained in a model organism, such as an ob/ob or db/db mouse, to another mammal, such as a human. These extrapolations are not simply based on the weights of the two organisms, but rather incorporate differences in metabolism, differences in pharmacological delivery, and administrative routes. Based on these types of considerations, a suitable dose will, in alternative embodiments, typically be in the range of from about 0.5 to about 100 mg/kg/day, from about 1 to about 75 mg/kg of body weight per day, from about 3 to about 50 mg per kilogram body weight of the recipient per day, or in the range of 6 to 90 mg/kg/day, most preferably in the range of 15 to 60 mg/kg/day.

The compound is conveniently administered in unit dosage form; for example, in alternative embodiments, containing 0.5 to 1000 mg, 5 to 750 mg, most conveniently, or 10 to 500 mg of active ingredient per unit dosage form.

One skilled in the art will recognize that dosage and dosage forms outside these typical ranges can be tested and, where appropriate, be used in the methods of this invention.

In separate embodiments, the active ingredient may be administered to achieve peak plasma concentrations of the active compound of from about 0.5 to about 75 $\mu$M, about 1 to 50 $\mu$M, or about 2 to about 30 $\mu$M. This may be achieved, for example, by the intravenous injection of a 0.05 to 5% solution of the active ingredient, optionally in saline, or orally administered as a bolus containing about 0.5–500 mg of the active ingredient. Desirable blood levels may be maintained by continuous infusion to provide about 0.01–5.0 mg/kg/hr or by intermittent infusions containing about 0.4–15 mg/kg of the active ingredients.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The following examples are given to illustrate the invention and are not intended to be inclusive in any manner:

EXAMPLES

Example 1

3-(3,5,5,8,8-Pentamethyl-5,6,7,8-tetrahydro-2-naphthyl)-4-methoxybenzylidene-2,4-thiazolidinedione, also Referred to as Compound 1 Herein To a solution of toluene (200 mL) containing piperidine (0.6 mL) and acetic acid (0.6 mL) was added 4-methoxy-3-(3,5,5,8,8-pentamethyl-5,6,7,8-tetrahydronaphthylen-2-yl)benzaldehyde (20.3 g, 60.2 mmol) and 2,4-thiazolidinedione (7.0 g, 60.2 mmol) and the solution was heated at reflux for 6 hours with continuous removal of water using a Dean-Stark water separator. The reaction mixture was, cooled to room temperature, and the resulting crystalline compound was filtered and washed with water (150 mL). The yellow solid was taken up in a mixture of ethanol (50 mL) and water (300 mL), filtered, further washed with water (500 mL) and dried to afford 21.0 g of 5-[4-methoxy-3-(3,5,5,8,8-pentamethyl-5,6,7,8-tetrahydronaphthalen-2-yl)benzylidene] thiazolidine-2,4-dione (80%). The toluene filtrate was concentrated under reduced pressure and the residue chromatographed on silica gel (Biotage, 2% methanol in dichloromethane) to give 2.5 g more of product (9.7%); totalsyield 89.7%.

$^1$H NMR (500 MHz; DMSO-d$_6$): $\delta$1.22 (s, 6 H); 1.27 (s, 6 H); 1.65 (s, 4 H); 2.01 (s, 3 H); 3.80 (s, 3 H); 7.03 (s, 1 H); 7.17 (s, 1 H); 7.23 (d, J=8.7 Hz, 1 H); 7.32 (d, J=2.4 Hz, 1 H); 7.60 (dd, J$_1$=8.7 Hz, J$_2$=2 Hz, 1 H); 7.78 (s, 1 H); 12.5 (br, 1 H).

$^1$H NMR (500 MHz; CDCl$_3$): $\delta$1.27 (s, 6 H); 1.32 (s, 6 H); 1.70 (s, 4 H); 2.10 (s, 3 H); 3.83 (s, 3 H); 7.03 (d, J=8.4 Hz, 1 H); 7.09 (s, 1 H); 7.16 (s, 1 H); 7.33 (d, J=2 Hz, 1 H); 7.48 (dd, J$_1$=8.6 Hz, J$_2$=2 Hz, 1 H); 7.83 (s, 1 H). $^{13}$C NMR (125 MHz; DMSO-d$_6$): $\delta$19.2; 31.6; 33.5; 33.6; 34.7; 55.6; 111.9; 120.9; 125.5; 127.3; 127.7; 131.0; 131.2; 131.6; 132.9; 134.6; 141.5; 143.4; 158.1; 167.9; 168.1.

The intermediate 4-methoxy-3-(3,5,5,8,8-pentamethyl-5,6,7,8-tetrahydronaphthalen-2-yl)benzaldehyde was prepared as follows:

a. (3,5,5,8,8-Pentamethyl-5,6,7,8-tetrahydronaphthalen-2-yl) boronic acid.

The (3,5,5,8,8-pentamethyl-5,6,7,8-tetrahydronaphthalen-2-yl) boronic acid, was prepared in an analogous manner as reported by Dawson et al. (*J. Med. Chem.* 1995, 38, 3368–3383).

b. 3-(3,5,5,8,8-Pentamethyl-5,6,7,8-tetrahydronaphthalen-2-yl)-4-methoxy-benzaldehyde.

A mixture of 3-bromo-4-methoxybenzaldehyde (19.0 g, 88.4 mmol), (3,5,5,8,8-pentamethyl-5,6,7,8-tetrahydronaphthalen-2-yl) boronic acid (23.8 g, 97.2 mmol) and potassium carbonate (48.8 g, 353.6 mmol) in 1,2-dimethoxyethane (500 mL) and water (40 mL) was degassed with argon for 60 minutes. Tetrakis(triphenylphosphine) palladium(0) (5.0 g, 4.3 mmol) was added and the mixture heated at reflux under argon for 16 hours. The solution was cooled to room temperature, diluted with ethyl acetate (200 mL) and washed successively with water (100 mL) and brine (100 mL), dried over anhydrous magnesium sulfate, filtered and evaporated. The residue was chromatographed on silica gel (eluent: ethyl acetate/hexane, 1:9) to give 26.8 g of 3-(3,5,5,8,8-pentamethyl-5,6,7,8-tetrahydronaphthalen-2-yl)-4-methoxy-benzaldehyde (90%). $^1$H NMR (500 MHz; CDCl$_3$): $\delta$1.26 (s, 6 H); 1.32 (s, 6 H); 1.70 (s, 4 H); 2.08 (s, 3 H); 3.89 (s, 3 H); 7.06 (d, J=8.5 Hz, 1 H); 7.09 (s, 1 H); 7.16 (s, 1 H); 7.71 (d, J=2.0 Hz, 1 H); 7.88 (dd, J$_1$=2.0 Hz, J$_2$=8.5 Hz 1 H), 9.91 (s, 1 H).

Example 2

3-(3,5,5,8,8-Pentamethyl-5,6,7,8-tetrahydro-2-naphthyl)-4-methoxybenzylidene-2-thioxo-4-thiazolidinedione, also Referred to as Compound 2 herein To a mixture of 2-thioxo-4-thiazolidine (199 mg, 1.49 mmol), piperidine (0.05 mL, 0.49 mmol) and acetic acid (0.05 mL, 0.89 mmol) in dry toluene (20 mL) was added 3-(3,5,5,8,8-pentamethyl-5,6,7,8-tetrahydronaphthalen-2-yl)-4-methoxy-benzaldehyde (500 mg, 1.49 mmol). The reaction mixture was heated under reflux for 22 hours, allowed to cool to room temperature and extracted with ethyl acetate (2×75 mL). The organic extracts were successively washed with water (50 mL), saturated aqueous NH$_4$Cl (50 mL), saturated aqueous NaCl (100 mL), dried over MgSO$_4$ and filtered. Removal of the solvent under reduced pressure gave a yellow solid which was purified by column chromatography, using a Biotage 40S cartridge, eluting with 15% ethyl acetate/85% hexane. The title compound was isolated as a bright yellow solid (394 mg, 60%).

$^1$H NMR (500 MHz, DMSO-d$_6$): δ1.27 and 1.23 (12 H), 1.65 (s, 4 H), 2.02 (s, 3 H), 3.82 (s, 3 H), 7.04 (s, 1 H), 7.18 (s, 1 H), 7.26 (d, J=8.7 Hz, 1 H), 7.33 (d, J=2.5 Hz, 1 H), 7.62 (dd, J$_1$=6.2 Hz, J$_2$=2.5 Hz, 1 H), 7.67 (s, 1 H), 13.75 (s, 1 H).

Example 3

5-(3,5,5,8,8-Pentamethyl-5,6,7,8-tetrahydro-2-naphthyl)-6-methoxy-3-pyridylidene-2,4-thiazolidinedione Prepared similar to Example 1 in 63% yield using 2-methoxy-3-(3,5,5,8,8-pentamethyl-5,6,7,8-tetrahydronaphthalen-2-yl)pyridine-5-carboxaldehyde.

$^1$H NMR (500 MHz, DMSO-d$_6$): δ1.22 (s, 6 H), 1.27 (s, 6 H), 1.64 (s, 4 H) 2.03 (s, 3 H), 3.90 (s, 3 H), 7.10 (s, 1 H), 7.21 (s, 1 H), 7.67 (d, J=2.2 Hz, 1 H), 7.84 (s, 1 H), 8.47 (d, J=2.1 Hz, 1 H), 12.65 (s, 1 H).

The intermediate 2-methoxy-3-(3,5,5,8,8-pentamethyl-5,6,7,8-tetrahydronaphthalen-2-yl)pyridine-5-carboxaldehyde was prepared as follows:

a. 5-Bromo-2-methoxy-pyridine

To a suspension of 2-methoxypyridine (10.00 g, 0.09 mol) and sodium acetate (8.27 g, 0.10 mmol) in 30 mL of glacial acetic acid was added a solution of bromine in 20 mL glacial acetic acid while maintaining the reaction temperature below 50° C. After 3 hours, 100 mL of H$_2$O was added and the resulting solution neutralized with cold 2.5 M NaOH. The suspension was extracted with ether (2×200 mL), the combined organics were dried over MgSO$_4$, filtered and evaporated. The crude material was purified on silica gel (eluent: hexane to hexane:ethyl acetate 97:3) and distilled (34–36.5° C./0.05 mm Hg) to give 8.84 g (51.3%) of 5-bromo-2-methoxy-pyridine as a clear colorless liquid.

b. 2-methoxy-pyridine-5-carboxaldehyde.

To a solution of 5-bromo-2-methoxy-pyridine (8.50 g, 45.2 mmol) in 100 mL dry ether under argon at −64° C. was added 1.6 M n-BuLi in hexanes. The resulting mixture was stirred at −64° C. for 40 minutes and allowed to warm to −35° C. To the resulting suspension was added 7.0 mL of dry DMF over 10 minutes. After 15 minutes, the mixture was allowed to warm to 0° C. and 75 mL of 5% NH$_4$Cl was added. The resulting mixture was separated and the aqueous layer extracted with EtOAc (3×75 mL). The organics were combined, dried (MgSO$_4$), filtered and evaporated under vacuum to give 2-methoxy-pyridine-5-carboxaldehyde as a tannish solid (recrystallized from hexane), 3.76 g (60.6%); m.p. 48.5–50° C.

c. 2-methoxy-3-bromo-pyridine-5-carboxyaldehyde

To a suspension of 2-methoxypyridine-5-carboxyaldehyde (3.50 g, 25.5 mmol) and sodium acetate (2.30 g, 28.1 mmol) in 15 mL of glacial acetic acid was added a solution of bromine (1.45 mL, 28.1 mmol);in 20 mL glacial acetic acid and the resulting mixture heated to 100° C. for 18 hours under argon. The mixture was cooled, diluted with water (50 mL) and neutralized with 2.0 M NaOH. The resulting mixture was extracted with ether (4×200 mL), the combined organics dried (MgSO$_4$), filtered and evaporated. The crude material was purified on silica gel [gradient, hexane:ethyl acetate (99:1) to hexane:ethyl acetate (92:8)] to give 2-methoxy-3-bromo-pyridine-5-carboxyaldehyde as a white solid,0.97 g (17.6%). $^1$H NMR (500 MHz, CDCl$_3$): δ4.11 (s, 3 H), 8.29 (d, J=2.0 Hz, 1 H), 8.56 (d, J=2.0 Hz, 1 H), 9.92 (s, 1 H).

d. 2-Methoxy-3-(3,5,5,8,8-pentamethyl-5,6,7,8-tetrahydronaphthalen-2-yl)pyridine-5-carboxaldehyde.

A mixture of 2-methoxy-3-bromo-pyridine-5-carboxyaldehyde (319 mg, 1.48 mmol), (3,5,5,8,8-pentamethyl-5,6,7,8-tetrahydronaphthalen-2-yl) boronic acid (545 mg, 2.22 mmol), potassium carbonate (817 mg, 5.91 mmol) and water (2 mL) in anhydrous 1,2-dimethoxyethane (30 mL) was degassed with argon for 15 minutes prior to the addition of tetrakis(triphenylphosphine) palladium (0) (342 mg, 0.30 mmol). The reaction mixture was heated under reflux for 15 hours, allowed to cool to room temperature and extracted with ethyl acetate (2×100 mL). The organic extracts were successively washed with water (100 mL), a saturated aqueous solution of NH$_4$Cl (100 mL), a saturated aqueous solution of NaCl (100 mL), dried over MgSO$_4$ and filtered. Removal of the solvent under reduced pressure gave an oil which was purified by column chromatography, using a Biotage 12M cartridge, eluting with 5% ethyl acetate/95% hexane. The title compound was isolated in quantitative yield.

$^1$H NMR (500 MHz, CDCl$_3$): δ1.24 (s, 6 H), 1.27 (s, 6 H), 1.70 (s, 4 H), 2.09 (s, 3 H), 4.09 (s, 3 H), 7.07 (s, 1 H), 7.17 (s, 1 H), 7.94 (d, J=2.0 Hz, 1 H), 8.64 (d, J=2.0 Hz, 1 H), 10.01 (s, 1 H).

Example 4

3-(3,5,5,8,8-Pentamethyl-5,6,7,8-tetrahydro-2-naphthyl)-2-fluoro-4-methoxybenzylidene-2,4-thiazolidinedione, also Referred to as Compound 4 Herein Prepared similar to Example 1 in a 57% yield using 3-(3,5,5,8,8-Pentamethyl-5,6,7,8-tetrahydro-2-naphthyl)-2-fluoro-4-methoxybenzaldehyde.

$^1$H NMR (500 MHz; CDCl$_3$): δ1.25 (s, 6 H); 1.32 (s, 6 H); 1.69 (s, 4 H); 2.06 (s, 3 H); 3.83 (s, 3 H); 6.88 (d, J=8.5 Hz, 1 H); 7.05 (s, 1 H); 7.18 (s, 1 H); 7.47 (t, J=8.5 Hz, 1 H); 8.08 (s, 1 H).

The intermediate 3-(3,5,5,8,8-pentamethyl-5,6,7,8-tetrahydro-2-naphthyl)-2-fluoro-4-methoxybenzaldehyde was prepared as follows:

a. 2-Fluoro-3-hydroxy-4-methoxybenzaldehyde.

To a heated solution (80° C.) of hexamethylenetetramine (2.8 g, 20 mmol) in trifluoroacetic acid (10 mL) was added dropwise over a 50 minutes period 2-fluoro-6-methoxyphenol (1.42 g, 10 mmol) in trifluoroacetic acid (10 mL). The mixture was heated for an additional 1 hour, concentrated and water (50 ml) was added. The solution was stirred for 10 minutes and solid potassium carbonate was added until the solution was neutral. The solid that formed was collected to afford 1.1 g of 2-fluoro-3-hydroxy-4-methoxybenzaldehyde (65%). $^1$H NMR (500 MHz; DMSO-d$_6$): δ3.90 (s, 3 H); 6.98 (d, J=8.5 Hz, 1 H); 7.31 (t, J=8.5 Hz, 1 H); 9.66 (br, 1 H); 10.02 (s, 1 H).

b. 2-Fluoro-4-methoxy-3-trifluoromethanesulfonyl benzaldehyde

To a solution of 2-fluoro-3-hydroxy-4-methoxybenzaldehyde (1.1 g, 6.47 mmol) in dichloromethane (50 mL) was added pyridine (0.6 mL, 7.76 mmol) and the solution cooled to 0° C. Triflic anhydride (1.3 mL, 7.76 mmol) was added slowly and the reaction mixture warmed slowly to room temperature and stirred overnight at room temperature. The solution was washed successively with water and brine, dried over anhydrous magnesium sulfate, filtered and evaporated. The residue was chromatographed and silica gel (eluent: ethyl acetate/hexane, 1:4) to give 1.21 g of 2-fluoro-4-methoxy-3-trifluoromethanesulfonyl benzaldehyde (62%). $^1$H NMR (500 MHz; CDCl$_3$): δ4.03 (s, 3 H), 6.95 (d, J=8.0 Hz, 1 H), 7.89 (dd, J$_1$=8.0 Hz, J$_2$=9.0 Hz, 1 H), 10.20 (s, 1 H).

c. 2-Fluoro-4-methoxy-3-trifluoromethanesulfonyl benzaldehyde.

A mixture of 2-fluoro-4-methoxy-3-trifluoromethanesulfonyl benzaldehyde (1.21 g, 4.01 mmol), (3,5,5,8,8-pentamethyl-5,6,7,8-tetrahydronaphthalen-2-yl) boronic acid (1.08 g, 4.41 mmol) and potassium carbonate (2.22 g, 16.04 mmol) in 1,2-dimethoxyethane (30 mL) and water (2 mL) was degassed with argon for 30 minutes. Tetrakis(triphenylphosphine)palladium(0) (0.23 g, 0.2 mmol) was added and the mixture heated at reflux under argon for 16 hours. The solution was cooled to room temperature, diluted with ethyl acetate and washed successively with water and brine, dried over anhydrous magnesium sulfate, filtered and evaporated. The residue was chromatographed on silica gel (Biotage, eluent: ethyl acetate/hexane, 0.5:8.5) to give 0.87 g of 4-methoxy-2-fluoro-3-(3,5,5,8,8-pentamethyl-5,6,7,8-tetrahydronaphthalen-2-yl) benzaldehyde (62%). $^1$H NMR (500 MHz; CDCl$_3$): δ1.26 (s, 6 H), 1.32 (s, 6 H), 1.69 (s, 4 H), 2.07 (s, 3 H), 3.85 (s, 3 H), 7.07 (d, J=8.8 Hz, 1 H), 7.07 (s, 1 H), 7.19 (s, 1 H), 7.90 (t, J=8.8 Hz, 1 H), 10.25 (s, 1 H).

Example 5

6-(3,5,5,8,8-Pentamethyl-5,6,7,8-tetrahydro-2-naphthyl)-5-methoxy-2-pyridylidene-2,4-thiazolidinedione Prepared similar to Example 1 in a 21% yield using 6-(3,5,5,8,8-pentamethyl-5,6,7,8-tetrahydronaphthalen-2-yl)-5-methoxy-pyridine-2-carboxaldehyde.

$^1$H NMR (500 MHz; CDCl$_3$): δ1.32 (s, 6 H); 1.34 (s, 6 H); 1.72 (s, 3 H); 2.18 (s, 3 H); 3.87 (s, 3 H); 7.18 (s, 1 H); 7.30 (d, J=8.4 Hz, 1 H); 7.40 (s, 1 H); 7.50 (d, J=8.5 Hz, 1 H); 7.77 (s, 1 H).

The intermediate 6-(3,5,5,8,8-Pentamethyl-5,6,7,8-tetrahydronaphth-2-yl)-5-methoxy-pyridine-2-carboxaldehyde was prepared as follows:

a. 2-Bromo-3-hydroxy-6-methyl-pyridine.

To a solution of 5-hydroxy-2-methylpyridine (8.80 g, 80.6 mmol) in 125 mL of pyridine was added a solution of bromine (14.18 g, 88.7 mmol) in 50 mL pyridine dropwise. The temperature of the reaction mixture rose to 40° C. upon completion of addition. After 1 hour the pyridine was removed under vacuum and the resulting solid was suspended into water (200 mL) and stirred overnight. The solid was collected and dried to give the desire product as a brownish solid (8.05 g, 53.1% yield). $^1$H NMR (500 MHz, CDCl$_3$): δ2.21 (s, 3 H), 6.73 (d, J=8.1 Hz, 1 H), 6.94 (d, J=8.1 Hz, 1 H), 9.36 (brs, 1 H).

b. 2-Bromo-3-methoxy-6-methyl-pyridine

A stirred mixture of 2-bromo-3-hydroxy-6-methyl-pyridine (7.89 g, 42.0 mmol), potassium carbonate (11.60 g, 83.9 mmol) and iodomethane (8.93 g, 62.9 mmol, 3.92 mL) in acetone (100 mL) was heated under reflux overnight. The mixture was filtered, evaporated and purified on silica gel (hexane:ethyl acetate, 95:5 to 9:1) to give the desired product as a white solid (7.49 g, 88.3%). $^1$H NMR (500 MHz, CDCl$_3$): δ2.46 (s, 3 H), 3.87 (s, 3 H), 7.04 (s, 2 H).

c. 5-Methoxy-6-bromo-pyridine-2-carboxaldehyde.

A stirred mixture of 2-bromo-3-methoxy-6-methyl-pyridine (2.00 g, 9.9 mmol), Cu(II) sulfate pentahydrate (2.47 g, 9.9 mmol), and potassium peroxydisulfate (8.03 g, 29.7 mmol) in 80 mL of acetonitrile/H$_2$O (1:1) was heated under reflux. After 1 hour, the dark green mixture was cooled to room temperature and CH$_2$Cl$_2$ was added. The layers were separated and the aqueous layer further extracted with CH$_2$Cl$_2$. The organics were combined, dried (MgSO$_4$), filtered and evaporated. The resulting crude product was purified on silica gel [Biotage, hexane:ethyl acetate (4:1)] to give a white solid (0.51 g, 24% yield).

d. 6-(3,5,5,8,8-Pentamethyl-5,6,7,8-tetrahydronaphth-2-yl)-5-methoxy-pyridine-2-carboxaldehyde.

A mixture of 6-bromo-5-methoxypyridine-2-carboxaldehyde (512 mg, 2.37 mmol), (3,5,5,8,8-pentamethyl-5,6,7,8-tetrahydronaphthalen-2-yl) boronic acid (700 mg, 2.84 mmol) and potassium carbonate (1.31 g, 9.5 mmol) in 1,2-dimethoxyethane (22 mL) and water (2 mL) was degassed with argon. Tetrakis(triphenylphosphine) palladium(0) (550 mg, 0.48 mmol) was added and the mixture heated under reflux under argon for 24 hours. The solution was cooled to room temperature, diluted with ethyl acetate and washed successively with water and brine, dried over anhydrous magnesium sulfate, filtered and evaporated. The residue was chromatographed on silica gel (Biotage hexane:EtOAc 9:1) to give 603 mg (75% yield) of 6-(3,5,5,8,8-pentamethyl-5,6,7,8-tetrahydronaphth-2-yl)-5-methoxy-pyridine-2-carboxaldehyde.

$^1$H NMR (500 MHz; CDCl$_3$): δ1.29 (s, 6 H), 1.31 (s, 6 H), 1.70 (s, 4 H), 2.15 (s, 3 H), 3.90 (s, 3 H), 7.20 (s, 1 H), 7.27 (s, 1 H), 7.37 (d, J=8.5 Hz, 1 H), 8.00 (d, J=8.5 Hz, 1 H), 10.04 (s, 1 H).

Example 6

3-(1,4-Diisopropyl-6-methyl-1,2,3,4-tetrahydro-7-quinoxalinyl)-4-methoxybenzylidene-2,4-thiazolidinedione 3-(1,4-Diisopropyl-6-methyl-1,2,3,4-tetrahydro-7-quinoxalinyl)-4-methoxybenzylidene-2,4-thiazolidinedione may be prepared in a similar manner as described in Example 1 using 3-(1,4-diisopropyl-6-methyl-1,2,3,4-tetrahydro-7-quinoxalinyl)-4-methoxybenzaldehyde.

The intermediate 3-(1,4-diisopropyl6-methyl-1,2,3,4-tetrahydro-7-quinoxalinyl)-4-methoxybenzaldehyde was prepared as follows:

a. 6-Methyl-1,2,3,4-tetrahydroquinoxaline.

To a solution of 6-methylquinoxaline (2 g, 13.87 mmol) and nickel (II) chloride hexahydrate (6.6 g, 27.74 mmol) in anhydrous methanol (70 mL) was added in portions, sodium borohydride (10.5 g, 277.43 mmol) while maintaining the temperature between 0° C. and 5° C. The reaction mixture was stirred at 0° C. for 20 minutes and at room temperature for 4 hours. Removal of the solvent under reduced pressure was ensued by acidification of the residue with 2N HCl (600 mL). The mixture was stirred at room temperature for 16 hours and filtered. The green filtrate was made basic (pH 10–11) using concentrated NH$_4$OH (150 mL) and extracted with diethylether (3×200 mL). The ethereal extracts were successively washed with water (2×300 mL), a saturated aqueous solution of NaCl (150 mL), dried over MgSO$_4$ and filtered. Removal of the solvent under reduced pressure gave 6-methyl-1,2,3,4-tetrahydroquinoxaline as a solid (880 mg, 43%).

¹H NMR (500 MHz; CDCl₃): δ2.17 (s, 3 H), 3.39–3.40 (m, 4 H), 6.41–6.33 (m, 3 H).

b. 1,4-diisopropyl-6-methyl-1,2,3,4-tetrahydroquinoxaline.

A mixture of 6-methyl-1,2,3,4-tetrahydroquinoxaline (851 mg, 5.75 mmol), potassium carbonate (3.18 g, 23 mmol) and 2-iodopropane (4.6 mL, 46 mmol) in dry dimethylformamide (10 mL) was heated under reflux for 19 hours, allowed to cool to room temperature prior to the addition of water (100 mL) and extracted with ethyl acetate (2×75 mL). The organic extracts were successively washed with a saturated aqueous solution of NH₄Cl (100 mL), a saturated aqueous solution of NaCl (100 mL), dried over MgSO₄ and filtered. Removal of the solvent under reduced pressure gave a dark orange oil which was purified by column chromatography, using a Biotage 40S cartridge, eluting with 5% ethyl acetate/95% hexane, to give 1,4-diisopropyl-6-methyl-1,2,3,4-tetrahydroquinoxaline as a solid (870 mg, 66%).

¹H NMR (500 MHz; CDCl₃): δ1.19–1.16 (m, 12 H), 2.24 (s, 3 H), 3.16–3.14 (m, 2, H), 3.23–3.21 (m, 2 H), 4.02 (quintet, J=6.5 Hz, 1 H), 4.08 (quintet, J=6.5 Hz, 1 H), 6.44 (d, J=8.0 Hz, 1 H), 6.49 (s, 1 H), 6.56 (d, J=8.1 Hz, 1 H).

c. 7-Bromo-1,4-diisopropyl-6-methyl-1,2,3,4-tetrahydroquinoxaline.

A mixture of 1,4-diisopropyl-6-methyl-1,2,3,4-tetrahydroquinoxaline (516 mg, 2.22 mmol) and tetrabutylammonium tribromide (1.18 g, 2.45 mmol) in anhydrous dichloromethane (20 mL) was stirred at room temperature for 4 hours. The solution was washed successively with a saturated aqueous solution of NaHCO₃ (150 mL), water (150 mL), a saturated aqueous, solution of NaCl (150 mL), dried over MgSO₄ and filtered. Removal of the solvent under reduced pressure gave a solid which was purified by column chromatography, using a Biotage 40S cartridge, eluting with 5% ethyl acetate/95% hexane, to give 7-bromo-1,4-diisopropyl-6-methyl-1,2,3,4-tetrahydroquinoxaline as a white solid (480 mg, 70%).

¹H NMR (500 MHz; CDCl₃): δ1.16–1.15 (m, 12 H), 2.25 (s, 3 H), 3.16 (s, 4 H), 3.95 (quintet, J=6.6 Hz, 1 H), 4.00 (quintet, J=6.6 Hz, 1 H), 6.47 (s, 1 H), 6.73 (s, 1 H).

d. 3-(1,4-Diisopropyl-6-methyl-1,2,3,4-tetrahydro-7-quinoxalinyl)-4-methoxybenzaldehyde.

A mixture of 7-bromo-1,4-diisopropyl-6-methyl-1,2,3,4-tetrahydroquinoxaline (469 mg, 1.51 mmol), 2-methoxy-5-formylphenylboronic acid (407 mg, 2.26 mmol), potassium carbonate (834 mg, 6.03 mmol) and water (2.5 mL) in anhydrous 1,2-dimethoxyethane (30 mL) was degassed with argon for 15 minutes prior to the addition of tetrakis(triphenylphosphine)palladium (0) (349 mg, 0.30 mmol). The reaction mixture was heated under reflux for 8.5 hours, allowed to cool to room temperature and extracted with ethyl acetate (2×100 mL). The organic extracts were successively washed with water (100 mL), saturated aqueous NH4Cl (100 mL), saturated aqueous NaCl (100 mL), dried over MgSO₄ and filtered. Removal of the solvent under reduced pressure gave an oil which was purified by column chromatography, using a Biotage 40S cartridge, eluting with 10% ethyl acetate/90% hexane. The title compound was isolated as bright yellow solid (315 mg, 57%).

¹H NMR (500 MHz; CDCl₃): δ1.14 (d, J=6.6 Hz, 6 H), 1.20 (d, J=6.8 Hz, 6 H), 2.01 (s, 3 H), 3.19–3.17 (m, 2 H), 3.27–3.25 (m, 2 H), 3.86 (s, 3 H), 3.99 (quintet, J=6.6 Hz, 1 H), 4.11 (quintet, J=6.6 Hz, 1 H), 6.47 (s, 1 H), 6.51 (s, 1 H), 7.03 (d, J=8.7 Hz, 1 H), 7.72 (d, J=1.9 Hz, 1 H), 7.84 (dd, J=8.3 Hz, J=2.0 Hz, 1 H), 9.90 (s, 1 H).

Example 7

3-(3,5,5,8,8-Pentamethyl-5,6,7,8-tetrahydro-2-naphthyl)-4-methoxy-6-hydroxybenzylidene-2,4-thiazolidinedione 3-(3,5,5,8,8-Pentamethyl-5,6,7,8-tetrahydro-2-naphthyl)-4-methoxy-6-hydroxybenzylidene-2,4-thiazolidinedione may be prepared in a similar manner as described in Example 1 using 3-(3,5,5,8,8-pentamethyl-5,6,7,8-tetrahydro-2-naphthyl)-4-methoxy-6-hydroxybenzaldehyde.

The intermediate 3-(3,5,5,8,8-pentamethyl-5,6,7,8-tetrahydro-2-naphthyl)-4-methoxy-6-hydroxybenzaldehyde was prepared as follows:

a. 3-Bromo-6-hydroxy-4-methoxy-benzaldehyde.

A mixture of 2-hydroxy-4-methoxy-benzaldehyde (3.64 g, 20 mmol) and tetrabutylammonium tribromide (6.40 g, 20 mmol) in anhydrous dichloromethane (200 mL) was stirred at room temperature for 24 hours. The solution was washed successively with a saturated aqueous solution of NaHCO₃ (150 mL), water (150 mL), a saturated aqueous solution of NaCl (150 mL), dried over MgSO₄ and filtered. Removal of the solvent under reduced pressure gave a solid which was purified by column chromatography, using a Biotage 40M cartridge; eluting with 5% ethyl acetate/95% hexane to give 3-bromo-6-hydroxy-4-methoxy-benzaldehyde as a white solid (3.50 g, 76%).

¹H NMR (500 MHz; CDCl₃): δ3.94 (s, 3 H), 6.47 (s, 1 H), 7.67 (s, 1 H), 9.68 (s, 1 H), 11.43 (s, 1 H).

b. 3-(3,5,5,8,8-pentamethyl-5,6,7,8-tetrahydro-2-naphthyl)-4-methoxy-6-hydroxybenzaldehyde.

A mixture of 3-bromo-6-hydroxy-4-methoxy-benzaldehyde (2 g, 8.66 mmol), (3,5,5,8,8-pentamethyl-5,6,7,8-tetrahydronaphthalen-2-yl) boronic acid (3.18 g, 12.99 mmol), potassium carbonate (4.79 g, 34.63 mmol) and water (4 mL) in anhydrous 1,2-dimethoxyethane (140 mL) was degassed with argon for 15 minutes prior to the addition of tetrakis(triphenylphosphine)palladium(0) (2.0 g, 1.73 mmol). The reaction mixture was heated under reflux for 15 hours, allowed to cool to room temperature and extracted with ethyl acetate (2×100 mL). The organic extracts were successively washed with water (100 mL), a saturated aqueous solution of NH₄Cl (100 mL), a saturated solution of NaCl (100 mL), dried over MgSO₄ and filtered. Removal of the solvent under reduced pressure gave an oil which was purified by column chromatography, using a Biotage 40M cartridge, eluting with 5% ethyl acetate/95% hexane, to give 3-(3,5,5,8,8-pentamethyl-5,6,7,8-tetrahydro-2-naphthyl)-4-methoxy-6-hydroxybenzaldehyde as a white solid (2.2 g, 73%).

¹H NMR (500 MHz; CDCl₃): δ1.28 (s, 6 H), 1.33 (s, 6 H), 1.70 (s, 4 H), 2.08 (s, 1 H), 3.84 (s, 3 H), 6.51 (s, 1 H), 7.07 (s, 1 H), 7.15 (s, 1 H), 7.31 (s, 1 H), 9.73 (s, 1 H), 11.53 (s, 1 H).

Example 8

3-(3,5,5,8,8-Pentamethyl-5,6,7,8-tetrahydro-2-naphthyl)-4,6-dimethoxybenzylidene-2,4-thiazolidinedione 3-(3,5,5,8,8-Pentamethyl-5,6,7,8-tetrahydro-2-naphthyl)-4,6-dimethoxybenzylidene-2,4-thiazolidinedione may be prepared in a similar manner as described in Example 1 using 3-(3,5,5,8,8-pentamethyl-5,6,7,8-tetrahydro-2-naphthyl)-4,6-dimethoxybenzaldehyde.

The intermediate 3-(3,5,5,8,8-pentamethyl-5,6,7,8-tetrahydro-2-naphthyl)-4,6-dimethoxybenzaldehyde was prepared as follows:

To a solution of 3-(3,5,5,8,8-pentamethyl-5,6,7,8-tetrahydro-2-naphthyl)-4-methoxy-6-hydroxybenzaldehyde (1.04 g, 2.95 mmol) in acetone (20 mL) was added dimethylsulfate (0.37 mL, 3.84 mmol) and potassium carbonate (490 mg, 3.55 mmol). The reaction mixture was stirred at room temperature for 15 hours and extracted with ethyl acetate (2×50 mL). The organic extracts were successively washed with water (100 mL) and a saturated aqueous solution of NaCl (100 mL), dried over $MgSO_4$ and filtered. Removal of the solvent under reduced pressure gave 3-(3,5,5,8,8-pentamethyl-5,6,7,8-tetrahydro-2-naphthyl)-4,6-dimethoxybenzaldehyde (1.05 g, 97%).

$^1$H NMR (500 MHz; $CDCl_3$): δ1.26 (s, 6 H), 1.31 (s, 6 H), 1.69 (s, 4 H), 2.06 (s, 3 H 3.87 (s, 3 H), 3.99 (s, 3 H), 6.50 (s, 1 H), 7.05 (s, 1 H), 7.13 (s, 1 H), 7.67 (s, 1 H), 10.35 (s, 1 H).

Example 9

3-(5,5,8,8-Tetramethyl-5,6,7,8-tetrahydro-2-naphthyl)-2,4-dimethoxybenzylidene-2,4-thiazolidinedione 3-(5,5,8,8-Tetramethyl-5,6,7,8-tetrahydro-2-naphthyl)-2,4-dimethoxybenzylidene-2,4-thiazolidinedione may be prepared in a similar manner as described in Example 1 using 3-(5,5,8,8-tetramethyl-5,6,7,8-tetrahydronaphthylen-2-yl)-2,4-dimethoxy-benzaldehyde.

The intermediate 3-(5,5,8,8-tetramethyl-5,6,7,8-tetrahydro-2-naphthyl)-2,4-dimethoxy-benzaldehyde was prepared as follows:

a. 6-(2,6-Dimethoxyphenyl)-1,1,4,4-tetramethy-1,2,3,4-tetrahydronaphthlene.

A mixture of 2,6-dimethoxy-phenylboronic acid (1.0 g, 5.48 mmol), 6-bromo-1,1,4,4 tetramethyl,2,3,4-tetrahydronaphthalene (0.73 g, 2.74 mmol) and potassium carbonate (1.50 g, 10.96 mmol) in 1,2-dimethoxyethane (20 mL) and water (1.0 mL) was degassed with argon for 15 minutes. Tetrakis(triphenylphosphine)palladium(0) (0.60 g, 0.54 mmol) was added and the mixture heated at reflux under argon for 5 hours. The solution was cooled to room temperature, diluted with ethyl acetate and washed successively with water and brine, dried over anhydrous magnesium sulfate, filtered and evaporated. The residue was chromatographed on silica gel (eluent: ethyl acetate/hexane, 1:9) to give 0.92 g of 6-(2,6-Dimethoxyphenyl)-1,1,4,4-tetramethy-1,2,3,4-tetrahydronaphthlene.

b. 6-(5-Bromo-2,6-dimethoxyphenyl)-1,1,4,4-tetramethy-1,2,3,4-tetrahydronaphthlene.

To a solution of 6-(2,6-dimethoxyphenyl)-1,1,4,4-tetramethy-1,2,3,4-tetrahydronaphthlene (340 mg, 1.05 mmol) in dichloromethane (10 mL) was added pyridinium tribromide (335 mg, 1.05 mmol) and the reaction mixture stirred at room temperature overnight. The solution was diluted with ethyl acetate and washed successively with water and brine, dried over anhydrous magnesium sulfate, filtered and evaporated. The residue was purified on silica gel (eluent: ethyl acetate/hexane, 0.5:9.5) to give 0.24 g (57%) of 6-(5-bromo-2,6-dimethoxyphenyl)-1,1,4,4-tetramethy-1,2,3,4-tetrahydronaphthlene. $^1$H NMR (500 MHz; $CDCl_3$): δ1.28 (s, 6 H); 1.31 (s, 6 H); 1.70 (s, 4 H); 3.35 (s, 3 H); 3.73 (s, 3 H); 7.14 (dd, $J_1$=1.5 Hz, $J_2$=8.5 Hz, 1 H); 7.15 (dd, $J_1$=2.0 Hz, $J_2$=8.5 Hz, 1H); 7.30 (d, J=8.0 Hz, 1H); 7.36 (d, J=1.5 Hz, 1H); 7.45 (d, J=8.0 Hz, 1 H), 7.95 (br, 1 H).

c. 3-(5,5,8,8-Tetramethyl-5,6,7,8-tetrahydro-2-naphthyl)-2,4-dimethoxy-benzaldehyde.

To a solution of 6-(5-bromo-2,6-dimethoxyphenyl)-1,1,4,4-tetramethy-1,2,3,4-tetrahydronaphthlene (0.24 g, 0.55 mmol) in anhydrous THF (6 mL) was added at −78° C. under argon n-BuLi (1.6 M in hexane, 0.7 mL, 1.1 mmol). The solution was stirred for 5 minutes at −78° C. and N,N-dimethylformamide (0.13 mL, 1.65 mmol) was added. The reaction mixture was stirred 2 hours at −78° C. then quenched with aqueous ammonium chloride and brought to room temperature. The solution was diluted with ethyl acetate and washed successively with water and brine, dried over anhydrous magnesium sulfate, filtered and evaporated. The residue was chromatographed and silica gel (eluent: ethyl acetate/hexane, 1:9) to give 0.14 g (72%) of 3-(5,5,8,8-tetramethyl-5,6,7,8-tetrahydro-2-naphthyl)-2,4-dimethoxy-benzaldehyde. $^1$H NMR (500 MHz; $CDCl_3$): δ1.29 (s, 6 H); 1.32 (s, 6 H); 1.72 (s, 4 H); 3.37 (s, 3 H); 3.83 (s, 3 H); 6.83 (d, J=9.0 Hz, 1 H); 7.14 (dd, $J_1$=2.0 Hz, $J_2$=8.5 Hz, 1 H); 7.33 (d, J=8.0 Hz, 1 H); 7.36 (s, 1 H); 7.85 (d, J=8.5 Hz, 1 H); 10.29 (s, 1 H).

Example 10

3-(1-Isopropyl-7-methyl-1,2,3,4-tetrahydro-6-quinolinyl)-4-methoxybenzylidene-2,4-thiazolidinedione 3-(1-Isopropyl-7-methyl-1,2,3,4-tetrahydro-6-quinolinyl)-4-methoxybenzylidene-2,4-thiazolidinedione may be prepared in a similar manner as described in Example 1 using 3-(1-Isopropyl-7-methyl-1,2,3,4-tetrahydro-6-quinolinyl)-4-methoxybenzaldehyde.

The intermediate 3-(1-Isopropyl-7-methyl-1,2,3,4-tetrahydro-6-quinolinyl)-4-methoxybenzaldehyde was prepared as follows:

a. 1-Isopropyl-7-methyl-1,2,3,4-tetrahydro-6-bromoquinoline.

To a cooled solution of 7-methyl quinoline (5.00 g, 35 mmol) and nickel (II) chloride hexahydrate (1.40 g, 6 mmol) in methanol (130 mL) was added sodium borohydride (5.50 g, 140 mmol) portionwise. The reaction mixture was stirred at 0° C. for 1 hour and then at room temperature for 3 hours. Hydrochloric acid (2N, 200 mL) was added to the black residue and the mixture stirred at room temperature until disappearance of the black precipitate. The acidic solution was neutralized with concentrated ammonium hydroxide and extracted with ether. The organic layer was washed with brine and dried over anhydrous magnesium sulfate, filtered and evaporated to give 5.28 g of 7-methyl-1,2,3,4-tetrahydro-quinoline (100%), used without further purification. A mixture of 7-methyl-1,2,3,4-tetrahydro-quinoline (1.20 g, 8.2 mmol), potassium carbonate (2.3 g, 16.4 mmol) and isopropyl iodide (3.3 mL, 32.8 mmol) in N,N-dimethylformamide (10 mL) was heated at 60° C. with stirring for 24 hours. The solution was cooled to room temperature and washed successively with water and brine, dried over anhydrous magnesium sulfate, filtered and evaporated to give 1.28 g (82%) of 1-isopropyl-7-methyl-1,2,3,4-tetrahydro-quinoline. To a solution of 1-isopropyl-7-methyl-1,2,3,4-tetrahydro-quinoline (1.04 g, 5.5 mmol) in dichloromethane was added tetrabutylammonium tribromide (2.65 g, 5.5 mmol) and the solution stirred at room temperature for 5 hours. The solution was washed successively with water and brine, dried over anhydrous magnesium sulfate, filtered and evaporated. The residue was chromatographed and silica gel (ethyl acetate/hexane, 1:9) to give 1.00 g of 6-bromo-1-isopropyl-7-methyl-1,2,3,4-tetrahydro-quinoline (67%).

$^1$H NMR (500 MHz; CDCl$_3$): δ1.10 (s, 3 H); 1.11 (s, 3 H); 1.81 (m, 2 H); 2.20 (s, 3 H); 2.64 (m, 2 H); 3.0.8 (m, 2 H); 3.5 (m, 1 H); 6.94 (s, 1 H); 6.54 (s, 1 H); 7.08 (s, 1 H).

b. 3-(1-Isopropyl-7-methyl-1,2,3,4-tetrahydro-6-quinolinyl)-4-methoxybenzaldehyde.

A mixture of 6-bromo-1-isopropyl-7-methyl-1,2,3,4-tetrahydro-quinoline (0.85 g, 3.16 mmol), 2-methoxy-5-formyl boronic acid (1.13 g, 6.31 mmol) and potassium carbonate (1.70 g, 12.64 mmol) in 1,2-dimethoxyethane (30 mL) and water (1.5 mL) was degassed with argon for 15 minutes. Tetrakis(triphenylphosphine)palladium(0) (0.80 g, 0.63 mmol) was added and the mixture heated at reflux under argon for 35 hours. The solution was cooled to room temperature, diluted with ethyl acetate and washed successively with water and brine, dried over anhydrous magnesium sulfate, filtered and evaporated. The residue was chromatographed and silica gel (eluent: ethyl acetate/hexane, 1:9) to give 0.81 g of 3-(1-isopropyl-7-methyl-1,2,3,4-tetrahydro-6-quinolinyl)-4-methoxybenzaldehyde (79%). $^1$H NMR (500 MHz; CDCl$_3$): δ1.18 (s, 3 H); 1.20 (s, 3 H); 1.94 (m, 2 H); 2.06 (s, 3 H); 2.72 (m, 2 H); 3.18 (m, 2 H); 3.85 (s, 3 H); 4.16 (m, 1 H); 6.57 (s, 1 H); 6.78 (s, 1 H); 7.02 (d, 1 H); 7.69 (d, 1 H); 7.34 (s, 1 H); 7.84 (m, 1 H); 9.89 (s, 1 H).

Example 11

3-(3,5,5,8,8-Pentamethyl-5,6,7,8-tetrahydro-2-naphthyl)-4,5-dimethoxybenzylidene-2,4-thiazolidinedione 3-(3,5,5,8,8-Pentamethyl-5,6,7,8-tetrahydro-2-naphthyl)-4,5-dimethoxybenzylidene-2,4-thiazolidinedione may be prepared in a similar manner as described in Example 1 using 3-(3,5,5,8,8-pentamethyl-5,6,7,8-tetrahydro-2-naphthyl)-4,5-dimethoxybenzaldehyde prepared from 3-bromo-4,5-dimethoxybenzaldehyde.

The intermediate 3-bromo-4,5-dimethoxybenzaldehyde was prepared as follows:

To a solution of 5-bromovanillin (2.00 g, 8.65 mmol) in acetone (50 mL) was added potassium carbonate (1.4 g, 10.38 mmol) and dimethylsulfate (1 mL, 10.38 mmol). The solution was stirred at room temperature for 16 hours. The reaction mixture was diluted with ethyl acetate and the organic layer was washed successively with water and brine, dried over anhydrous magnesium sulfate, filtered and evaporated to afford 1.88 g of 3-bromo-4,5-dimethoxybenzaldehyde (89%).

Example 12

3-(3,5,5,8,8-Pentamethyl-5,6,7,8-tetrahydro-2-naphthyl)-2-fluoro-4-methoxybenzylidene)-2-thioxo-4-thiazolidinedione 3-(3,5,5,8,8-Pentamethyl-5,6,7,8-tetrahydro-2-naphthyl)-2-fluoro-4-methoxybenzylidene)-2-thioxo-4-thiazolidinedione was prepared in a similar manner as described in Example 2 in a 57% yield using intermediate 3-(3,5,5,8,8-Pentamethyl-5,6,7,8-tetrahydro-2-naphthyl)-2-fluoro-4-methoxybenzaldehyde described in Example 4. $^1$H NMR (500 MHz; CDCl$_3$) 1.25 (2 s, 6 H); 1.32 (2 s, 6 H); 1.69 (s, 4 H); 2.05 (s, 3 H); 3.84 (s, 3 H); 6.88 (d, J=8.5 Hz, 1 H); 7.05 (s, 1 H); 7.18 (s, 1 H); 7.41 (t, J=8.5 Hz, 1 H); 7.89 (s, 1 H).

Example 13

3-[(3,5,5,8,8-Pentamethyl-5,6,7,8-tetrahydro-2-naphthyl)-4-methoxybenzyl]-2,4-thiazolidinedione, also Referred to as Compound 13 Herein To a solution of 4-methoxy-3-(3,5,5,8,7-pentamethyl-5,6,7,8-tetrahydronaphthalen-2-yl) benzyl alcohol (195 mg, 0.57 mmol) in acetic acid (glacial, 3 mL) was added HBr (48%, 1 mL) and the resulting mixture heated at reflux for 2 hours. The solution was cooled to room temperature, diluted with ethyl acetate and washed successively with water and brine, dried over anhydrous magnesium sulfate, filtered and evaporated to afford 200 mg of crude 4-methoxy-3-(3,5,5,8,7-pentamethyl-5,6,7,8-tetrahydronaphthalen-2-yl) benzyl bromide. To a stirred solution of 2,4-thiazolidinedione (133 mg, 1.14 mmol) in anhydrous THF (6 mL) was added, at -78° C. under argon, n-BuLi (1.6M in hexane, 1.5 mL, 2.4 mmol) dropwise. The mixture was maintained at -78° C. for 15 minutes and then warmed to 0° C. for 30 minutes to complete the dianion formation. Upon recooling to -78° C., 4-methoxy-3-(3,5,5,8,7-pentamethyl-5,6,7,8-tetrahydronaphthalen-2-yl) benzyl bromide was added in THF (3 mL). After 30 minutes the orange solution was allowed to warm to room temperature. After 1.5 hours, the solution was treated with 2N HCl, diluted with ethyl acetate and washed successively with water and brine, dried over anhydrous magnesium sulfate, filtered and evaporated. The residue was chromatographed on silica gel (eluent: ethyl acetate/hexane 2:8) to give 61 mg of 5-[4-methoxy-3-(3,5,5,8,8-pentamethyl-5,6,7,8-tetrahydronaphthalen-2-yl)benzyl] thiazolidine-2,4-dione (24% for 3 steps from benzaldehyde). $^1$H NMR (500 MHz; CDCl$_3$): δ1.27 (s, 6 H); 1.26 (s, 6 H); 1.69 (s, 4 H); 2.08 (s, 3 H); 3.12 (dd, J$_1$=14.0 Hz, J$_2$=9.5 Hz, 1 H); 3.50 (dd, J$_1$=14.0 Hz, J$_2$=4.0 Hz, 1 H); 3.76 (s, 3 H); 4.54 (dd, J$_1$=9.5 Hz, J$_2$=4.0 Hz, 1 H); 6.89 (d, J=8.0 Hz, 1 H); 7.03 (d, J=2 Hz, 1 H); 7.07 (s, 1 H); 7.14 (s, 1 H); 7.17 (dd, J$_1$=8.0 Hz, J$_2$=2.0 Hz, 1 H), 7.95 (br, 1 H).

The intermediate 4-methoxy-3-(3,5,5,8,7-pentamethyl-5,6,7,8-tetrahydronaphthalen-2-yl) benzyl alcohol was prepared as follows:

a. 4-Methoxy-3-(3,5,5,8,7-pentamethyl-5,6,7,8-tetrahydronaphthalen-2-yl) benzaldehyde.

A mixture of 2-methoxy-5-formylphenylboronic acid (2.3 g, 12.80 mmol), 6-bromo-1,1,4,4,7pentamethyl 1,2,3,4-tetrahydronaphthalene (3.0 g, 10.66 mmol) and potassium carbonate (5.89 g, 42.64 mmol) in 1,2-dimethoxyethane (100 mL) and water (5 mL) was degassed with argon for 15 minutes.

Tetrakis(triphenylphosphine)palladium(0) (2.4 g, 2.13 mmol) was added and the mixture heated at reflux under argon for 8 hours. The solution was cooled to room temperature, diluted with ethyl acetate and washed successively with water and brine, dried over anhydrous magnesium sulfate, filtered and evaporated. The residue was chromatographed on silica gel (eluent: 0% to 25% ethyl acetate in hexane) to give 3.43 g (95%) of 4-methoxy-3-(3,5,5,8,7-pentamethyl-5,6,7,8-tetrahydronaphthalen-2-yl) benzaldehyde. $^1$H NMR (500 MHz; CDCl$_3$): δ1.26 (s, 6 H); 1.32 (s, 6 H); 1.70 (s, 4 H); 2.08 (s, 3 H); 3.89 (s, 3 H); 7.06 (d, J=8.5 Hz, 1 H); 7.09 (s, 1 H); 7.16 (s, 1 H); 7.71 (d, J=2.0 Hz, 1 H); 7.88 (dd, J$_1$=8.5 Hz, J$_2$=2.0 Hz 1 H), 9.91 (s, 1 H).

b. 4-Methoxy-3-(3,5,5,8,7-pentamethyl-5,6,7,8-tetrahydronaphthalen-2-yl) benzyl alcohol.

To a solution of 4-methoxy-3-(3,5,5,8,7-pentamethyl-5,6,7,8-tetrahydronaphthalen-2-yl) benzaldehyde (200 mg, 0.59 mmol) in methanol (5 mL) was added at 0° C. in small portions sodium borohydride (70 mg, 1.77 mmol). The solution was stirred 1 hour at 0° C. then quenched with 2N HCl. The reaction mixture was diluted with ethyl acetate and washed successively with water and brine, dried over anhydrous magnesium sulfate; filtered and evaporated to afford 195 mg (98%) of 4-methoxy-3-(3,5,5,8,7-pentamethyl-5,6,7,8-tetrahydronaphthalen-2-yl) benzyl alcohol.

¹H NMR (500 MHz; CDCl₃): δ1.27 (s, 6 H); 1.31 (s, 6 H); 1.69 (s, 4 H); 2.10 (s, 3 H); 3.78 (s, 3 H); 4.65 (s, 2 H); 6.94 (d, J=8.5 Hz, 1 H); 7.10 (s, 1 H); 7.14 (s, 1 H); 7.17 (d, J=2.0 Hz, 1 H); 7.33 (dd, J₁=8.5 Hz, J₂=2.0 Hz, 1 H).

Example 14

5-(3,5,5,8,8-Pentamethyl-5,6,7,8-tetrahydro-2-naphthyl)-6-methoxy-3-pyridylidene-2-thioxo-4-thiazolidinedione 5-(3,5,5,8,8-Pentamethyl-5,6,7,8-tetrahydro-2-naphthyl)-6-methoxy-3-pyridylidene-2-thioxo-4-thiazolidinedione may be prepared in a similar manner as described in Example 2 using intermediate 2-methoxy-3-(3,5,5,8,8-pentamethyl-5,6,7,8-tetrahydronaphthalen-2-yl)pyridine-5-carboxaldehyde described in Example 3.

Example 15

6-(3,5,5,8,8-Pentamethyl-5,6,7,8-tetrahydro-2-naphthyl)-5-methoxy-2-pyridylidene-2-thioxo-4-thiazolidinedione 6-(3,5,5,8,8-Pentamethyl-5,6,7,8-tetrahydro-2-naphthyl)-5-methoxy-2-pyridylidene-2-thioxo-4-thiazolidinedione may be prepared in a similar manner as described in Example 2 using intermediate 6-(3,5,5,8,8-pentamethyl-5,6,7,8-tetrahydronaphthalen-2-yl)-5-methoxy-pyridine-2-carboxaldehyde described in Example 5.

Example 16

3-(3,5,5;8,8-Pentamethyl-5,6,7,8-tetrahydro-2-naphthyl)-4-methoxy-6-hydroxybenzylidene-2-thioxo-4-thiazolidinedione 3-(3,5,5,8,8-Pentamethyl-5,6,7,8-tetrahydro-2-naphthyl)-4-methoxy-6-hydroxybenzylidene-2-thioxo-4-thiazolidinedione may be prepared in a similar manner as described in Example 2 using intermediate 3-(3,5,5,8,8-pentamethyl-5,6,7,8-tetrahydro-2-naphthyl)-4-methoxy-6-hydroxybenzaldehyde described in Example 7.

Example 17

3-(3,5,5,8,8-Pentamethyl-5,6,7,8-tetrahydro-2-naphthyl)-4,6-dimethoxybenzylidene-2-thioxo-4-thiazolidinedione 3-(3,5,5,8,8-Pentamethyl-5,6,7,8-tetrahydro-2-naphthyl)-4-methoxy-6-hydroxybenzylidene-2-thioxo-4-thiazolidinedione may be prepared in a similar manner as described in Example 2 using intermediate 3-(3,5,5,8,8-pentamethyl-5,6,7,8-tetrahydro-2-naphthyl)-4,6-dimethoxybenzaldehyde described in Example 8.

Example 18

3-(1,4-Diisopropyl-6-methyl-1,2,3,4-tetrahydro-7-quinoxalinyl)-4-methoxybenzylidene-2-thioxo-4-thiazolidinedione 3-(1,4-Diisopropyl-6-methyl-1,2,3,4-tetrahydro-7-quinoxalinyl)-4-methoxybenzylidene-2-thioxo-4-thiazolidinedione may be prepared in a similar manner as described in Example 2 using intermediate 3-(1,4-diisopropyl-6-methyl-1,2,3,4-tetrahydro-7-quinoxalinyl)-4-methoxybenzaldehyde described in Example 6.

Example 19

3-(5,5,8,8-Tetramethyl-5,6,7,8-tetrahydro-2-naphthyl)-2,4-dimethoxybenzylidene-2-thioxo-4-thiazolidinedione 3-(5,5,8,8-Tetramethyl-5,6,7,8-tetrahydro-2-naphthyl)-2,4-dimethoxybenzylidene-2-thioxo-4-thiazolidinedione may be prepared in a similar manner as described in Example 2 using intermediate 3-(5,5,8,8-tetramethyl-5,6,7,8-tetrahydronaphthylen-2-yl)-2,4-dimethoxy-benzaldehyde described in Example 9.

Example 20

3-(1-Isopropyl-7-methyl-1,2,3,4-tetrahydro-6-quinolinyl)-4-methoxybenzylidene-2-thioxo-4-thiazolidinedione 3-(1-Isopropyl-7-methyl-1,2,3,4-tetrahydro-6-quinolinyl)-4-methoxybenzylidene-2-thioxo-4-thiazolidinedione may be prepared in a similar manner as described in Example 2 using intermediate 3-(1-isopropyl-7-methyl-1,2,3,4-tetrahydro-6-quinolinyl)-4-methoxybenzaldehyde described in Example 11.

Example 21

3-(3,5,5,8,8-Pentamethyl-5,6,7,8-tetrahydro-2-naphthyl)-4,5-dimethoxybenzylidene-2-thioxo-4-thiazolidinedione 3-(3,5,5,8,8-Pentamethyl-5,6,7,8-tetrahydro-2-naphthyl)-4,5-dimethoxybenzylidene-2-thioxo-4-thiazolidinedione may be prepared in a similar manner as described in Example 2 using intermediate 3-(3,5,5,8,8-pentamethyl-5,6,7,8-tetrahydro-2-naphthyl)-4,5-dimethoxybenzaldehyde which may be prepared from 3-bromo-4,5-dimethoxybenzaldehyde as described in Example 13.

Example 22

3-[(3,5,5,8,8-Pentamethyl-5,6,7,8-tetrahydro-2-naphthyl)-2-fluoro-4-methoxybenzyl)]-2,4-thiazolidinedione 3-[(3,5,5,8,8-Pentamethyl-5,6,7,8-tetrahydro-2-naphthyl)-2-fluoro-4-methoxybenzyl)]-2,4-thiazolidinedione may be prepared as described in Example 13 using intermediate 3-[(3,5,5,8,8-Pentamethyl-5,6,7,8-tetrahydro-2-naphthyl)-2-fluoro-4-methoxybenzaldehyde or alternatively by reducing the double bond of Example 4 {i.e., 3-(3,5,5,8,8-Pentamethyl-5,6,7,8-tetrahydro-2-naphthyl)-2-fluoro-4-methoxybenzylidene)-2,4-thiazolidinedione} by methods known in the art.

Example 23

5-[(3,5,5,8,8-Pentamethyl-5,6,7,8-tetrahydro-2-naphthyl)-6-methoxy-3-pyridylmethylene]-2,4-thiazolidinedione 5-[(3,5,5,8,8-7Pentamethyl-5,6,7,8-tetrahydro-2-naphthyl)-6-methoxy-3-pyridylmethylene]-2,4-thiazolidinedione may be prepared as described in Example 13 using intermediate 2-methoxy-3-(3,5,5,8,8-pentamethyl-5,6,7,8-tetrahydronaphthalen-2-yl)pyridine-5-carboxaldehyde or alternatively by reducing the double bond of Example 3 (i.e., 5-(3,5,5,8,8-Pentamethyl-5,6,7,8-tetrahydro-2-naphthyl)-6-methoxy-3-pyridylidene-2,4-thiazolidinedione) by methods known in the art.

Example 24

6-[(3,5,5,8,8-Pentamethyl-5,6,7,8-tetrahydro-2-naphthyl)-5-methoxy-2-pyridylmethylene]-2,4-thiazolidinedione 6-[(3,5,5,8,8-Pentamethyl-5,6,7,8-tetrahydro-2-naphthyl)-5-methoxy-2-pyridylmethylene]-2,4- thiazolidinedione may be prepared as described in Example 13 using intermediate 6-(3,5,5,8,8-pentamethyl-5,6,7,8-tetrahydronaphthalen-2-yl)-5-methoxy-pyridine-2-carboxaldehyde or alternatively by reducing the double bond of Example 5 (i.e., 6-(3,5,5,8,8-Pentamethyl-5,6,7,8-tetrahydro-2-naphthyl)-5-methoxy-2-pyridylidene-2,4-thiazolidinedione) by methods known in the art.

Example 25

3-[(3,5,5,8,8-Pentamethyl-5,6,7,8-tetrahydro-2-naphthyl)-4-methoxybenzyl]-2-thioxo-4-thiazolidinedione 3-[(3,5,5,8,8-Pentamethyl-5,6,7,8-tetrahydro-2-naphthyl)-4-methoxybenzyl]-2-thioxo-4-thiazolidinedione may be prepared as described in Example 13 using intermediate 3-[(3,5,5,8,8-Pentamethyl-5,6,7,8-tetrahydro-2-naphthyl)-4-methoxybenzaldehyde described in Example 1 or alternatively by reducing the double bond of Example 2 (i.e., 3-(3,5,5,8,8-Pentamethyl-5,6,7,8-tetrahydro-2-naphthyl)-4-methoxybenzylidene-2-thioxo-4-thiazolidinedione) by methods known in the art.

Example 26

3-(3,5,5,8,8-Pentamethyl-5,6,7,8-tetrahydro-2-naphthyl)-4-methoxybenzylidene-2-thioxo-4-imidazolidinedione A mixture of 2-thioxo-4-imidazolidinedione (117 mg, 1.0 mmol), piperidine (0.07 mL, 0.7 mmol) and 3-(3,5,5,8,8-pentamethyl-5,6,7,8-tetrahydronaphthalen-2-yl)-4-methoxy-benzaldehyde (336 mg, 1.0 mmol) in ethanol (15 mL) was heated under reflux for 5 hours, allowed to cool to room temperature, diluted with water and extracted with ethyl acetate (2×60 mL). The organic extracts were washed with saturated aqueous $NH_4Cl$ (60 mL), saturated aqueous NaCl (60 mL), dried over $MgSO_4$ and filtered. Removal of the solvent under reduced pressure gave a yellow solid that was purified by column chromatography, using a Biotage 40S cartridge, eluting with ethyl acetate/hexane (1:9). The title compound was isolated as a bright yellow solid (310 mg, 81%).

$^1$H NMR (500 MHz, DMSO-$d_6$): δ[1.22 (s) and 1.27(s), 12 H], 1.65 (s, 4 H), 2.01 (s, 3 H), 3.78 (s, 3 H), 6.50 (s, 1 H), 7.02 (s, 1 H), 7.12 (d, J=8.7 Hz, 1 H), 7.17 (s, 1 H), 7.57 (d, J=2.0 Hz, 1 H), 7.75 (dd, $J_1$=8.7 Hz, $J_2$=2.0 Hz, 1 H), 12.19 (s, 1 H), 12.27 (s, 1H).

$^{13}$C NMR (125 MHz, DMSO-$d_6$): δ19.4, 31.7, 33.5, 33.6, 34.7, 55.5, 111.4, 112.3, 124.7, 125.9, 127.2, 127.7, 131.0, 131.8, 132.4, 133.2, 135.0, 141.3, 143.1, 157.5, 165.9, 178.6.

The intermediate 4-methoxy-3-(3,5,5,8,8-pentamethyl-5,6,7,8-tetrahydronaphthalen-2-yl)benzaldehyde was prepared as described in Example 1.

Example 27

3-(3,5,5,8,8-Pentamethyl-5,6,7,8-tetrahydro-2-naphthyl)-4-hydroxybenzylidene-2,4-thiazolidinedione Prepared in a similar manner to Example 1 in a 74% yield using 4-hydroxy-3-(3,5,5,8,8-pentamethyl-5,6,7,8-tetrahydro-naphthalen-2-yl)benzaldehyde.

$^1$H NMR (500 MHz; DMSO-$d_6$) 1.22 (s, 6 H), 1.27 (s, 6 H), 1.64 (s, 4 H), 2.07 (s, 3 H), 7.03 (s, 1H), 7.05 (d, J=8.7 Hz, 1 H), 7.17 (s, 1 H), 7.28 (d, J=2.0 Hz, 1 H), 7.45 (dd, $J_1$=8.7 Hz, $J_2$=2.0 Hz, 1 H), 7.74 (s, 1 H), 10.32 (s, 1 H), 12.46 (s, 1 H).

The intermediate 4-hydroxy-3-(3,5,5,8,8-pentamethyl-5,6,7,8-tetrahydronaphthalen-2-yl)benzaldehyde was prepared as follows:

To a solution of 4-methoxy-3-(3,5,5,8,8-pentamethyl-5,6,7,8-tetrahydro-naphthalen-2-yl)benzaldehyde (0.30 g, 0.89 mmol) in anhydrous dichloromethane (10 ml) at −78° C. under argon was added boron tribromide (0.17 mL, 1.78 mmol). The solution was slowly warmed to room temperature and stirred for 24 hrs. The solution was carefully poured onto ice water and extracted with ethyl acetate. The organic layer was further washed with water and brine, dried over anhydrous magnesium sulfate, filtered and evaporated. The residue was chromatographed on silica gel (Biotage, eluent: ethyl acetate/hexane, 1:9) to give 0.24 g of product (84%).
$^1$H NMR (500 MHz; CDCl$_3$) 1.26 (s, 6 H), 1.32 (s, 6,H), 1.71 (s, 4 H), 2.10 (s, 3 H), 5:46 (s, 1 H), 7.11 (d, J=8.3 Hz, 1 H), 7.13 (s, 1 H); 7.26 (s, 1H); 7.69 (d, J=1.8 Hz, 1 H); 7.83 (dd, $J_1$=6.8 Hz, $J_2$=1.8 Hz, 1 H), 9.89 (s, 1 H).

Example 28

3-(3,5-Di-t-butyl-4-hydroxyphenyl)-3-methoxybenzylidene-2,4-thiazolidinedione

Prepared in a manner similar to Example 1 in a 50% yield using, 3-(3,5-di-t-butyl-4-hydroxyphenyl)-3-methoxybenzaldehyde.

$^1$H NMR (500 MHz, DMSO-$d_6$) 1.41 (s, 18 H), 3.84 (s, 3 H), 7.07 (s, 1 H), 7.24 (d, J=8.0 Hz, 1 H), 7.28 (s, 1 H), 7.53 (m, 2 H), 7.83 (s, 1 H), 12.5 (s, 1 H).

The intermediate 3-(3,5-di-t-butyl-4-hydroxyphenyl)-3-methoxybenzaldehyde was prepared in a manner similar to the procedure described in Example 1b using 4-bromo-2,6-di-t-butylphenol (0.50 g, 1.75 mmol), 2-methoxy-5-formylphenyl boronic acid (0.315 g, 1.75 mmol), tetrakis (triphenylphosphine)palladium(0) (0.20 g, 0.175 mmol), $K_2CO_3$ (0.95 g, 7.0 mmol), dimethoxyethane (15 mL) and $H_2O$ (1 mL); 367 mg, 61% yield.

$^1$H NMR (500 MHz; CDCl$_3$) 1.48 (s, 18 H), 3.93 (s, 3 H), 5.30 (s, 1 H), 7.08 (d, J=8.0 Hz, 1 H), 7.36 (s, 2 H), 7.80–7.85 (m, 2 H), 9.94 (s, 1 H).

Example 29

3-(3,5,5,8,8-Pentamethyl-5,6,7,8-tetrahydro-2-naphthyl)-4-methoxybenzylidene-2,4-imidazolidinedione A mixture of 2,4-imidazolidinedione (101 mg, 1.0 mmol), pyrrolidine (0.04 mL, 0.5 mmol) and 3-(3,5,5,8,8-pentamethyl-5,6,7,8-tetrahydronaphthalen-2-yl)-4-methoxy-benzaldehyde (336 mg, 1.0 mmol) in ethanol (15 mL) was heated under reflux for 24 hours, allowed to cool to room temperature and extracted with ethyl acetate (2×100 mL). The organic extracts were washed with saturated aqueous NH4Cl (60 mL), saturated $NH_4Cl$ (70 mL), saturated aqueous NaCl (60 mL), dried over $MgSO_4$ and filtered. Removal of the solvent under reduced pressure gave a yellow solid that was purified by column chromatography, using a Biotage 40S cartridge, eluting with ethyl acetate/hexane (3:7). The title compound was isolated as a yellow solid (270 mg, 65%).

$^1$H NMR (500 MHz, DMSO-$d_6$): δ1.22 (s, 6H), 1.27 (s, 6H), 1.65 (s, 4H), 2.00 (s, 3H), 3.75 (s, 3H), 6.42 (s, 1H), 7.01 (s, 1H), 7.08 (d, J=8.7 Hz, 1H), 7.15 (s, 1H), 7.38 (d, J=2.0 Hz, 1H), 7.62 (dd, J=2.6 Hz, J=8.8 Hz, 1H), 10.52 (s, 1H), 11.13 (s, 1H).

$^{13}$C NMR (125 MHz, DMSO-d$_6$): δ19.4, 31.7; 33.5, 33.6, 34.7, 55.4, 108.8, 111.3, 125.3, 126.2, 127.1, 127.7, 130.4, 130.9, 131.8, 133.1, 135.2, 141.2, 143.0, 155.7, 156.7, 165.6.

The intermediate 4-methoxy-3-(3,5,5,8-pentamethyl-5,6,7,8-tetrahydro-naphthalen-2-yl)benzaldehyde was prepared as described in Example 1.

Example 30

3-(3,5,5,8-Pentamethyl-5,6,7,8-tetrahydro-2-naphthyl)-4-dimethylaminobenzylidene-2,4-thiazolidinedione To a solution of toluene (30 mL) containing piperidine (0.2 mL) and acetic acid (0.2 mL) were added 2,4-thiazolidinedione (2.34 g, 20 mmol) and 4-dimethylamino-3-(3,5,5,8,8-pentamethyl-5,6,7,8-tetrahydronaphtalen-2-yl) benzaldehyde (7.0 g, 20 mmol). The reaction mixture was heated at reflux for 4 hours with continuous removal of water using a Dean-Stark water separator. After cooling to room temperature, a yellow solid formed that was collected and washed with ethanol, dried under vacuum to give 5.7 g of 5-[4-dimethylamino-3-(3,5,5,8,8-pentamethyl-5,6,7,8-tetrahydronaphtalen-2-yl)benzylidene]thiazolidine-2,4-dione. The organic layers were combined and evaporated. Trituration from ethanol afforded 1.4 g more of product (78%). $^1$H NMR (300 MHz; d-DMSO): 1.21 (s, 3H); 1.24 (s, 3H); 1.27 (s, 6H); 1.65 (s, 4H); 2.05 (s, 3H); 2.55 (s, 6H); 7.06 (d, J=9 Hz, 1H); 7.13 (s, 1H); 7.20 (s, 1H); 7.21 (d, J=2.4 Hz, 1H); 7.46, (dd, J$_1$=2.1 Hz, J$_2$=8.7 Hz, 1H); 7.73 (s, 1H); 12.43 (s, 1H).

The intermediate 4-dimethylamino-3-(3,5,5,8,8-pentamethyl-5,6,7,8-tetrahydronaphtalen-2-yl) benzaldehyde was prepared as follows:

a. 3-Bromo-4-(dimethylamino)-benzaldehyde.

To a solution of 4-(dimethylamino)-benzaldehyde (10.0 g, 67.03 mmol) in dichloromethane (250 mL) was added pyridinium tribromide (21.4 g, 67.03 mmol). The reaction mixture was stirred at room temperature overnight. The solution was washed successively with water and brine, dried over anhydrous magnesium sulfate, filtered and evaporated. Choromatography on silica gel (15% EtOAc in hexane) afforded 14.06 g of 3-bromo-4-(dimethylamino)-benzaldehyde (92%).

b. 4-Dimethylamino-3-(3,5,5,8,7-pentamethyl-5,6,7,8-tetrahydronaphthalen-2-yl) benzaldehyde.

To a solution of 3-bromo-4-(dimethylamino)-benzaldehyde (5 g, 21.92 mmol), (3,5,5,8,8-pentamethyl-5,6,7,8-tetrahydronaphtalen-2-yl) boronic acid (6.5 g, 26.30 mmol) in a mixture of toluene (50 mL), ethanol (10 mL) and water (7.5.mL) was added potassium carbonate (6.0 g, 43.83 mmol). The solution was degased with argon for 30 minutes. Tetrakis(triphenylphosphine)palladium(0) (0.50 g, 0.438 mmol) was added and the mixture heated at reflux under argon overnight. The solution was cooled to room temperature, diluted with ethyl acetate and washed successively with water and brine, dried over anhydrous magnesium sulfate, filtered and evaporated. The residue was chromatographed on silica gel (8% ethyl acetate in hexane) to give 7.08 g of 4-dimethylamino-3-(3,5,5,8,7-pentamethyl-5,6,7,8-tetrahydronaphtalen-2-yl) benzaldehyde (92%). $^1$H NMR (300 MHz; DMSO) 1.22 (s, 3H); 1.28 (s, 3H); 1.29 (s, 3H); 1.31 (s, 3H); 1.69 (s, 4H); 2.07 (s, 3H); 2.64 (s, 6H); 6.93 (d, J=8.4 Hz, 1H); 7.13 (s, 1H); 7.15 (s, 1H); 7.58 (d, J=2.4 Hz, 1H); 7.75 (dd, J$_1$=8.7 Hz, J$_2$=2.1 Hz, 1H); 9.80 (s, 1H).

Example 31

3-(3,5,5,8,8-Pentamethyl-5,6,7,8-tetrahydro-2-naphthyl)-4-chlorobenzylidene-2,4-thiazolidinedione To a solution of toluene (30 mL) containing piperidine (0.26 mL, 2.64 mmol) and acetic acid (0.26 mL) were added 2,4-thiazolidinedione (1.03 g, 8.81 mmol) and 4-chloro-3-(3,5,5,8,8-pentamethyl-5,6,7,8-tetrahydronaphtalen-2-yl) benzaldehyde (3.0 g, 8.81 mmol). The reaction mixture was heated at reflux for 12 hours with continuous removal of water using a Dean-Stark water separator. After cooling to room temperature, a yellow solid formed that was collected and washed with ethanol, dried under vacuum to give 2.7 g of 5-[4-chloro-3-(3,5,5,8,8-pentamethyl-5,6,7,8-tetrahydronaphtalen-2-yl)benzylidene]thiazolidine-2,4-dione (70% yield). $^1$H NMR (300 MHz; DMSO-d$_6$): 1.19 (s, 3H); 1.20 (s, 3H); 1.25 (s, 3H); 1.26 (s, 3H); 1.63 (s, 4H); 2.01 (s, 3H); 7.07 (s, 1H); 7.26 (s, 1H); 7.52 (d, J=2.1 Hz, 1H); 7.59 (dd, J$_1$=2.1 Hz, J$_2$=8.1 Hz, 1H); 7.71 (d, J=8.1 Hz, 1H); 7.83 (s, 1H); 12.68 (s, 1H).

The intermediate 4-chloro-3-(3,5,5,8,8-pentamethyl-5,6,7,8-tetrahydronaphtalen-2-yl)benzaldehyde was prepared as follows:

a. Ethyl 3-bromo-4-chlorobenzoate.

To a solution of 3-bromo-4-chlorobenzoic acid (3.00 g, 12.74 mmol) and cesium carbonate (6.23 g, 19.11 mmol) in acetonitrile (70 mL) was added iodoethane (5.1 mL, 63.7 mmol). The reaction mixture was-heated at reflux overnight. After cooling to room temperature, the solution was extracted with ethyl acetate. The organic layer was washed successively with water and brine, dried over anhydrous magnesium sulfate, filtered and evaporated. Choromatography on silica gel (biotage, 5% EtOAc in hexane) afforded 3.5 g of ethyl 3-bromo-4-chlorobenzoate (97%). $^1$H NMR (300 MHz; CDCl$_3$) 1.40 (t, 3H); 4.37 (q, 2H); 7.52 (d, J=8.1 Hz, 1H); 7.91 (dd, J$_1$=8.4 Hz, J$_2$=1.8 Hz, 1H); 8.28 (d, J=1.8 Hz, 1H).

b. 3-Bromo-4-chloro-benzyl alcohol.

To a solution of ethyl-3-bromo-4-chlorobenzoate (3.25 g, 12.34 mmol) in toluene (70 mL) was added, at −78° C. under argon, diisobutylaluminum hydride (1.5M in toluene, 24 mL, 37.01 mmol). The reaction mixture was stirred at −78° C. for 1 hr then methanol (9 mL) and water (18 mL) was added. The solution was warmed up to room temperature and extracted with ethyl acetate. The organic layer was washed successively with water and-brine, dried over anhydrous magnesium sulfate, filtered and evaporated to give 2.73. g of 3-bromo-4-chloro-benzyl alcohol.

c. 3-Bromo-4-chloro-benzaldehyde.

To a solution of 3-bromo-4-chlorobenzyl alcohol (2.73 g, 12.34 mmol) in dichloromethane (75 mL) was added, at room temperature, pyridinium chlorochromate (2.66 g, 12.34 mmol). The reaction mixture was stirred at room temperature for 1 hr then filtered over celite. The solvent was removed under reduced pressure and the residue chromatographed on silica gel (10% ethyl acetate in hexane) to afford 2.52 g of 3-bromo-4-chloro-benzaldehyde (93% yield). $^1$H NMR (300 MHz; CDCl$_3$) $^1$H NMR (300 MHz; CDCl$_3$) 7.65 (d, J=8.1 Hz, 1H); 7.78 (dd, J$_1$=8.4 Hz, J$_2$=2.1 Hz, 1H); 8.12 (d J=2.1 Hz, 1H).

d. 4-chloro-3-(3,5,5,8,7-pentamethyl-5,6,7,8-tetrahydronaphtalen-2-yl) benzaldehyde.

To a solution of 3-bromo-4-chlorobenzaldehyde (2.5 g, 11.39 mmol), (3,5,5,8,8-pentamethyl-5,6,7,8-tetrahydronaphtalen-2-yl) boronic acid (3.1 g, 12.53 mmol) in a mixture of toluene (25 mL), ethanol (5 mL) and water (4 mL) was added potassium carbonate (3.15 g, 22.78 mmol). The solution was degased with argon for 30 minutes. Tetrakis(triphenylphosphine)palladium(0) (0.26 g, 0.23 mmol) was added and the mixture heated at reflux under argon overnight. The solution was cooled to room temperature, diluted with ethyl acetate and washed successively with water and brine, dried over anhydrous magnesium sulfate, filtered and evaporated. The residue was chromatographed on silica gel (biotage: eluant:ethyl acetate/hexane, 5:95) to give 3.0 g of 4-chloro-3-(3,5,5,8,7-pentamethyl-5,6,7,8-tetrahydronaphtalen-2-yl) benzaldehyde (77%). $^1$H NMR (300 MHz; DMSO) 1.18 (s, 3H); 1.20 (s, 3H); 1.24 (s, 3H); 1.26 (s, 3H); 1.36 (s, 4H); 1.98 (s, 3H); 7.04 (s, 1H); 7.23 (s, 1H); 7.75 (d, J=7.8 Hz, 1H); 7.80 (d, J=1.8 Hz, 1H); 7.88 (dd, $J_1$=7.8 Hz, $J_2$=1.8 Hz, 1H); 9.99 (s, 1H).

Example 32

3-(3,5,5,8,8-Pentamethyl-5,6,7,8-tetrahydro-2-naphthyl)-4-trifluoromethoxybenzylidene-2,4-thiazolidinedione, also Referred to as Compound 32 herein To a solution of toluene (50 mL) containing piperidine (0.84 mL, 8.53 mmol) and acetic acid (0.84 mL) was added 2,4-thiazolidinedione (3.3 g, 28.43 mmol) and 4-trifluoromethoxy-3-(3,5,5,8,8-pentamethyl-5,6,7,8-tetrahydronaphthalen-2-yl)benzaldehyde (11.1 g, 28.43 mmol). The reaction mixture was heated at reflux with continuous removal of water using a Dean-Stark water separator. After 12 hours at reflux 25 mL of toluene was removed by distillation and the solution was cooled to room temperature. The yellow solid was collected and taken up in ethanol (40 ml). After stirring at room temperature for 15 minutes, the pale yellow solid was collected and washed with a minimum of ethanol, dried under vacuum to give 6.6 g of 3-(3,5,5,8,8-pentamethyl-5,6,7,8-tetrahydro-2-naphthyl)4-trifluoromethoxybenzylidene-2,4-thiazolidinedione. The organic layers were combined and evaporated. Further crystallization from ethanol afforded an additional 2.0 g to give a total of 8.6 g (61%) of product. $^1$H NMR (300 MHz; DMSO-$d_6$): 1.21 (s, 6H); 1.27 (s, 6H); 1.65 (s, 4H); 2.04 (s, 3H); 7.08 (s, 1H); 7.26 (s, 1H); 7.62 (m, 2H); 7.70 (dd, $J_1$=8.0 Hz, $J_2$=1.5 Hz, 1H); 7.86 (s, 1H); 12.5 (s, 1H).

The intermediate 4-trifluoromethoxy-3-(3,5,5,8,7-pentamethyl-5,6,7,8-tetrahydronaphthalen-2-yl) benzaldehyde was prepared as follows:

a. 3-Bromo-4trifluoromethoxybenzaldehyde.

To a solution of 4-trifluoromethoxybenzaldehyde (215 g, 1.13 mol) in a mixture of TFA (300 mL), $CH_2Cl_2$ (300 mL) and $H_2SO_4$ (150 mL) was added at room temperature N-bromosuccinimide (402 g, 2.26 mol) in equal portion over 7 hours. The reaction mixture was stirred for 4 days at room temperature, poured into ice-water and extracted with $CH_2Cl_2$. The organic layer was washed with water then treated with saturated $NaHCO_3$ (1.5 L) for 2 hrs. The layers were separated and the organic layer further washed with water and brine, dried over $MgSO_4$, filtered and evaporated. The residue was triturated with hexane and filtered. After evaporation of the solvent, the residue was distilled to give 3-bromo-4-trifluoromethoxybenzaldehyde (190.2 g, 81° C., 1.0 mm/Hg, 62%).

b. 4-Trifluoromethoxy-3-(3,5,5,8,7-pentamethyl-5,6,7,8-tetrahydronaphthalen-2-yl)benzaldehyde.

To a solution of 3bromo-4-trifluoromethoxybenzaldehyde (10.0 g, 37.2 mmol), (3,5,5,8,8-pentamethyl-5,6,7,8-tetrahydronaphthalen-2-yl) boronic acid (11 g, 44.68 mmol, 1.2 eq) in a mixture of toluene (100 mL), ethanol (20 mL) and water (15 mL) was added potassium carbonate (10.28 g, 74.4 mmol, 2 eq). The solution was degassed with argon for 40 minutes. Tetrakis(triphenylphosphine)palladium(0) (0.86 g, 0.74 mmol, 0.02 eq) was added and the mixture heated at reflux under argon for 22 hours. The solution was cooled to room temperature, diluted with ethyl acetate and washed successively with water and brine, dried over. $MgSO_4$, filtered and evaporated. The residue was chromatographed on silica gel (silica: 70–230 mesh, 60A, 400 g, eluant: ethyl acetate/hexane, 5:95) to give 4-trifluoromethoxy-3-(3,5,5,8,7-pentamethyl-5,6,7,8-tetrahydronaphthalen-2-yl) benzaldehyde (11.1 g, 76%). $^1$H NMR (300 MHz; $CDCl_3$): 1.25 (s, 6H); 1.32 (s, 6H); 1.70.(s, 4H); 2.08 (s, 3H); 7.06 (s, 1H); 7.18 (s, 1H); 7.48 (dd, $J_1$=8.4 Hz, $J_2$=1.5 Hz, 1H); 7.84 (d, J=2.0 Hz, 1H); 7.88 (dd, $J_1$=2.0 Hz, $J_2$=8.5 Hz 1H), 9.91 (s, 1H).

Example 33

3T3-L1 Differentiation In Vitro Assay Without Insulin

The following protocol was used to determine differentiation activity of the present invention. Differentiation of 3T3-L1 cells was assessed in 96 well plates. Two-days after confluence, cells were treated with either a test compound, such as Compound 1, or with a control, such as rosiglitazone. Drugs were replaced every 2–3 days for a total of 7 days.

Control for fully-differentiated adipocytes: Dexamethasone/Insulin (2.5 µM; 10 µg/ml, respectively).

Working concentrations: $10^{-10}$ to $10^{-5}$ M.

Cell line used: Mouse preadipocyte 3T3-L1, from passages # 3–9 (3,000 cells/well in 96-well plates). Culture media Growth medium (GM): DME Dulbecco's modified Eagle's medium containing 4500 mg/L glucose; 4 mM L-glutamine; 10 U/ml Pen-G; 10 mcg/ml Streptomycin and 10% Bovine Calf Serum (CS). Differentiation medium (DM): DME Dulbecco's modified Eagle's medium containing 4500 mg/L glucose; 4 mM L-glutamine; 10 U/ml Pen-G; 10 mcg/ml Streptomycin and 10% Fetal Calf Serum (FCS).

Lysis procedure: Upon culmination of the treatment using a test compound cells were washed once with PBS and lysed in situ with 50 µL 10% Hecameg. The lysates were further analyzed for their lipid content using the Triglyceride-GPO Trinder reagent from Sigma.

Example 34

3T3-L1 Differentiation In Vitro Assay With Insulin

The following protocol was used to determine differentiation activity of the present invention. Differentiation of 3T3-L1 cells was assessed in 96 well plates. Two-days after confluence (day 0), cells were treated with either a test compound, such as Compound 1, or with a control, such as rosiglitazone, in the presence of insulin (1.0 µg/mL). On day 2 no additional insulin was added in the differentiation medium. Drugs were replaced every 2–3 days for a total of 7 days.

Control for fully-differentiated adipocytes: Dexamethasone/Insulin (2.5 μM; 10 μg/ml, respectively).

Working concentrations: $10^{-10}$ to $10^{-5}$ M.

Cell line used: Mouse preadipocyte 3T3-L1, from passages #3–9 (3,000 cells/well in 96-well plates). Culture media Growth medium (GM): DME Dulbecco's modified Eagle's medium containing 4500 mg/L glucose; 4 mM L-glutamine; 10 U/ml Pen-G; 10 mcg/ml Streptomycin and 10% Bovine Calf Serum (CS). Differentiation medium (DM): DME Dulbecco's modified Eagle's medium containing 4500 mg/L glucose; 4 mM L-glutamine; 10 U/ml Pen-G; 10 mcg/ml Streptomycin and 10% Fetal Calf Serum (FCS).

Lysis procedure: Upon culmination of the treatment using the test compound cells were washed once with PBS and lysed in situ with 50 μL 10% Hecameg. The lysates were further analyzed for their lipid content using the Triglyceride-GPO Trinder reagent from Sigma.

Example 35

Oral Administration of Compound 1 in the Early Intervention Treatment of Type 2 Diabetes in db/db Mutant Mice Methods Animals and Housing Five week-old female db/db mutant mice (C57BL/KsJ-db +/+ m; Jackson Labs) were housed in a fixed 12-12-hr artificial light-dark cycle, and maintained on a standard high fat diet (containing at least 11% crude fat) provided ad libitum (Teklad S-2335). Animals were allowed two days to acclimate in this experimental environment prior to the initiation of the study.

Dosage Groups and Treatment

Prior to initiation of treatment, the animals were bled from the tail vein (100–200 μL of whole blood) and serum levels of glucose and triglycerides were measured in duplicate (Trinder kits; Sigma, St. Louis, Mo.). Based on these initial measures, animals (not yet hyperglycemic) were sorted into groups with approximately the same average serum glucose levels. Once sorted, the animals were housed six per cage and provided high fat rodent diet ad libitum.

Experiment I: (Compound 1)

Treatment groups(n=6/group):

1) db/db control (sesame oil)

2) Compound 1 (0.3 mg/kg; twice daily)

3) Compound 1 (1 mg/kg; twice daily)

Experiment II: (Compound 32)

Treatment groups(n=6/group):

1) db/db control (sesame oil)

2) Compound 32 (0.3 mg/kg; once daily)

3) Compound 32 (1 mg/kg; once daily)

4) Compound 32 (3 mg/kg; once daily)

3) Rosiglitazone (1 mg/kg; only daily)

Drug is prepared by mixing Compound 1 or 32 in sesame oil, and administered to animals in a volume of 5 ml/kg/dose. Drug is administered by oral gavage daily at the beginning (Compound 1 and 32) and end of the artificial dark cycle (Compound 1; 12 hour interval).

Serum Measurements

To monitor the effect of Compound 1 or 32, animals were bled following a three-hour fast at the end of the dark cycle on days 12 of the treatment period. Fasting serum glucose and triglyceride levels were measured in duplicate. The blood is kept at room temperature to allow coagulation, after which the serum is separated and assayed for glucose and triglyceride levels. As shown in FIGS. 2A, 2B, 4A and 4B, Compound 1 and 32 prevented the onset of diabetes in both treatment groups; with doses as low as 0.3 mg/kg when administered once (Compound 32) or twice (Compound 1) a day. Both serum glucose and triglyceride levels remained well within the normal range compared to control animals, which showed the typical hyperglycemia and hypertriglyceridemia associated with the onset of type 2 diabetes.

Example 36

Oral Administration of Compound 1 in the Late Intervention Treatment of Type 2 Diabetes in ob/ob Mutant Mice Methods Animals and Housing Five week-old male ob/ob mutant mice (C57BL/6J-ob; Jackson Labs) were housed in a fixed 12-12-hr artificial light-dark cycle, and maintained on a standard diet provided ad libitum. Animals were allowed two days to acclimate in this experimental environment prior to the initiation of the study.

Dosage Groups and Treatment

Prior to initiation of treatment, the animals were bled from the tail vein (100–200 μL of whole blood) and serum levels of glucose and triglycerides were measured in duplicate (Trinder kits; Sigma, St. Louis, Mo.). Based on these initial measures, hyperglycemic animals were sorted into groups with approximately the same average serum glucose levels. Once sorted, the animals were housed six per cage and provided standard rodent diet ad libitum.

Treatment groups(n=6/group):

1) ob/ob control (sesame oil)

2) Compound 1 (5 mg/kg twice daily)

Drug is prepared by mixing Compound 1 in sesame oil, and administered to animals in a volume of 3 ml/kg/dose. Drug is administered by oral gavage twice daily at the beginning and end of the artificial dark cycle (12 hour interval).

Serum Measurements

Figure 3B:
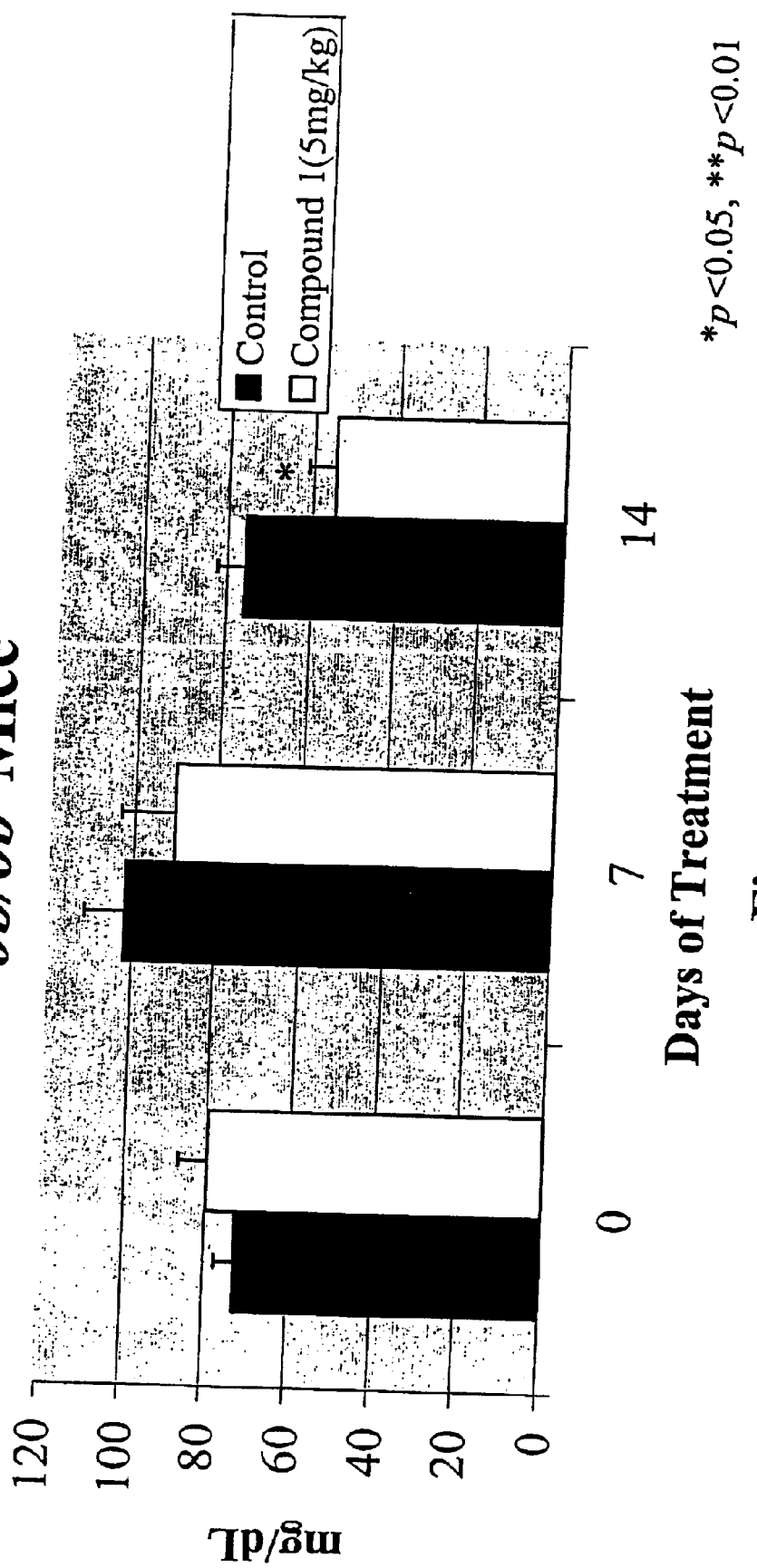
FIG. 3b shows the triglyceride lowering activity of Compound 1 in the ob/ob Mouse Model.

To monitor the effect of Compound 1, animals were bled following a three-hour fast at the end of the dark cycle on days 7 and 14 of the treatment period. Fasting serum glucose and triglyceride levels were measured in duplicate. The blood is kept at room temperature to allow coagulation, after which the serum is separated and assayed for glucose and triglyceride levels. As shown in FIGS. 3A and 3B, Compound 1 produced a significant decrease in serum glucose levels following 1 and 2 weeks of treatment (p<0.05; ANOVA and Fisher's Least Significant Difference; FIG. 3A). Similarly, treatment with Compound 1 for two weeks significantly reduced triglyceride levels compared to control (p<0.05, FIG. 3B).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:
1. A compound of the formula:

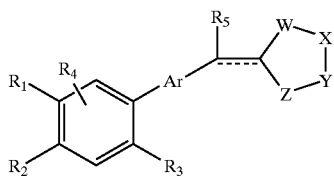

wherein:
R₁ and R₂ together with the aromatic ring bonded thereto comprise a cycloalkyl or cycloalkenyl ring having 3 to 8 carbon atoms that optionally comprises 1 or 2 heteroatoms selected from O, S, NH or N-alkyl, and wherein the cycloalkyl or cycloalkenyl ring is optionally further substituted with one or more groups independently selected from halogen, alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino;
R₃ and R₄ are independently or together hydrogen, halogen, alkyl, substituted alkyl, haloalkyl, alkoxy, substituted alkoxy, amino, mono-substituted amino, di-substituted amino or haloalkoxy;
Ar is Formula (VI), (VII) or (VIII):

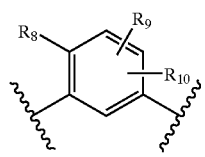 (VI)

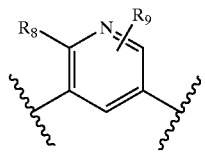 (VII)

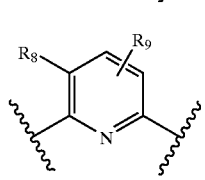 (VIII)

wherein:
R₈ is alkyl, substituted alkyl, alkenyl, haloalkyl, hydroxy, acyloxy, halogen, alkoxy, substituted alkoxy, amino, mono-substituted amino, di-substituted amino, alkylamide or haloalkoxy; and
R₉ and R₁₀ are independently or together hydrogen, halogen, alkyl, substituted alkyl, haloalkyl, alkenyl, substituted alkenyl, alkoxy, hydroxyl, amino, mono-substituted amino, di-substituted amino, alkylamide or haloalkoxy;
R₅ is hydrogen, or alkyl;
— represents a bond present or absent; and
W, X, Y and Z together form a 2,4-thiazolidinedione or a 2-thioxo-4-thiazolidinedione;
or a pharmaceutically acceptable salt thereof.

2. The compound of claim 1 wherein R₁ and R₂ together with the aromatic ring bonded thereto form a cycloalkyl ring.
3. The compound of claim 2 wherein the cycloalkyl ring is substituted with one or more alkyl groups comprising 1 to 12 carbon atoms.
4. The compound of claim 2 wherein the cycloalkyl ring is substituted with one or more methyl groups.
5. The compound of claim 1 wherein R₁ and R₂ together with the aromatic ring bonded thereto form a cyclohexyl ring.
6. The compound of claim 5 wherein the cyclohexyl ring is substituted with one or more groups independently selected from the group consisting of methyl, ethyl, n-propyl, iso-propyl, n-butyl, sec-butyl, t-butyl, amyl, t-amyl, and n-pentyl.
7. The compound of claim 1 wherein R₅ is hydrogen.
8. The compound of claim 1 wherein— represents a bond present.
9. The compound of claim 2 wherein R₅ is hydrogen, and — represents a bond present.
10. The compound of claim 2 wherein the cycloalkyl ring comprises 1 or 2 heteroatoms selected from O, NH and N-alkyl.
11. The compound of claim 10 wherein the cycloalkyl is substituted with one or more groups independently selected from the group consisting of methyl, ethyl, n-propyl, iso-propyl, n-butyl, sec-butyl, t-butyl, amyl, t-amyl, and n-pentyl.
12. The compound of claim 2 wherein R₅ is hydrogen, and — represents a bond present.
13. A compound of claim 2 wherein R₃ is hydrogen, methyl, ethyl, trifluoromethyl, methoxy or dimethylamino; and R₄ is hydrogen.
14. The compound of claim 1 wherein R₁ and R₂ together with the aromatic ring bonded thereto form a cycloalkenyl ring having 3 to 8 carbon atoms.
15. The compound of claim 14 wherein R₅ is hydrogen, and — represents a bond present.
16. The compounds of claim 2 that are equally or more potent than rosiglitazone in reducing glucose and triglyceride levels in diabetic db/db mice.
17. The compounds of claim 1 that induce the differentiation of mammalian preadipocytes into adipocytes at a concentration of $10^{-6}$ M or lower.
18. The compounds of claim 1 that are effective to decrease serum glucose levels of a mammal relative to control mammals having serum glucose levels indicative of type 2 diabetes.
19. The compounds of claim 1 that are effective to decrease serum triglyceride levels of a mammal relative to control mammals having serum triglyceride levels indicative of type 2 diabetes.
20. A pharmaceutical composition for administration in mammals comprising one or more pharmaceutically effective carriers and one or more compounds of claim 1 that is effective for modulating lipid metabolism, carbohydrate metabolism, lipid and carbohydrate metabolism, or adipocyte differentiation.
21. A pharmaceutical composition for administration in mammals comprising one or more pharmaceutically effective carriers and one or more compounds of claim 1 that is effective for treating type 2 diabetes.
22. A pharmaceutical composition for administration in mammals comprising one or more pharmaceutically effective carriers and one or more compounds of claim 1 that is effective for the treatment of a disease of uncontrolled cellular proliferation.

23. The pharmaceutical composition of claim 22, wherein the disease of uncontrolled cellular proliferation is cancer.

24. The pharmaceutical composition of claim 22, wherein the disease of uncontrolled cellular proliferation is carcinoma, lymphoma, leukemia, or sarcoma.

25. The pharmaceutical composition of claim 22, wherein the disease of uncontrolled cellular proliferation is Hodgkin's Disease, myeloid leukemia, polycystic kidney disease, bladder cancer, brain cancer, head and neck cancer, kidney cancer, lung cancer, myeloma, neuroblastoma/glioblastoma, ovarian cancer, pancreatic cancer, prostate cancer, skin cancer, liver cancer, melanoma, colon cancer, cervical carcinoma, breast cancer, epithelial cancer, and leukemia.

26. A method of modulating lipid metabolism, carbohydrate metabolism, lipid and carbohydrate metabolism, comprising administering to a mammal diagnosed as needing such modulation one or more compounds of claim 1 in an amount effective to modulate lipid metabolism, carbohydrate metabolism, or lipid and carbohydrate metabolism.

27. The method of claim 26 wherein the mammal is a human.

28. A method of treating type 2 diabetes comprising administering to a mammal diagnosed as having type 2 diabetes the compound of claim 1 in an amount effective to treat the type 2 diabetes.

29. The method of claim 28 wherein the mammal is a human.

30. A method of treatment for a disease of uncontrolled cellular proliferation comprising administering to a mammal diagnosed as having a disease of uncontrolled cellular proliferation one or more of compound of claim 1 in an amount effective to treat the disease of uncontrolled proliferation.

31. The method of claim 30 wherein the disease of uncontrolled cellular proliferation is Hodgkin's Disease, myeloid leukemia, polycystic kidney disease, bladder cancer, brain cancer, head and neck cancer, kidney cancer, lung cancer, myeloma, neuroblastoma/glioblastoma, ovarian cancer, pancreatic cancer, prostate cancer, skin cancer, liver cancer, melanoma, colon cancer, cervical carcinoma, breast cancer, epithelial cancer, and leukemia.

32. The method of claim 30 wherein the mammal is a human.

* * * * *

UNITED STATES PATENT AND TRADEMARK OFFICE
CERTIFICATE OF CORRECTION

PATENT NO. : 6,765,013 B2
DATED : July 20, 2004
INVENTOR(S) : Pfahl et al.

It is certified that error appears in the above-identified patent and that said Letters Patent is hereby corrected as shown below:

Column 88,
Line 29, please delete "claim 2" and substitute the following -- claim 11 --

Signed and Sealed this

Fourteenth Day of December, 2004

JON W. DUDAS
*Director of the United States Patent and Trademark Office*